(12) United States Patent
Hsu et al.

(10) Patent No.: US 11,717,147 B2
(45) Date of Patent: Aug. 8, 2023

(54) MEDICAL DEVICE HAVING MULTIPLE BENDING SECTIONS

(71) Applicant: Auris Health, Inc., Redwood City, CA (US)

(72) Inventors: Jason J. Hsu, Mountain View, CA (US); Ka Chun Wong, South San Francisco, CA (US)

(73) Assignee: Auris Health, Inc., Redwood City, CA (US)

( * ) Notice: Subject to any disclaimer, the term of this patent is extended or adjusted under 35 U.S.C. 154(b) by 0 days.

(21) Appl. No.: 16/994,245

(22) Filed: Aug. 14, 2020

(65) Prior Publication Data

US 2021/0045626 A1 Feb. 18, 2021

Related U.S. Application Data

(60) Provisional application No. 62/887,560, filed on Aug. 15, 2019.

(51) Int. Cl.
*A61B 1/307* (2006.01)
*A61B 1/005* (2006.01)
(Continued)

(52) U.S. Cl.
CPC ............ *A61B 1/307* (2013.01); *A61B 1/0057* (2013.01); *A61B 1/00085* (2013.01);
(Continued)

(58) Field of Classification Search
CPC . A61B 1/307; A61B 1/00071; A61B 1/00073; A61B 1/00075; A61B 1/00078;
(Continued)

(56) References Cited

U.S. PATENT DOCUMENTS

| 3,572,325 A | 3/1971 | Bazell et al. |
| 3,913,565 A | 10/1975 | Kawahara |

(Continued)

FOREIGN PATENT DOCUMENTS

| CN | 1846181 | 10/2006 |
| CN | 1857877 | 11/2006 |

(Continued)

OTHER PUBLICATIONS

International search report and written opinion dated Nov. 19, 2020 in application No. PCT/IB2020/057688.

*Primary Examiner* — Ryan N Henderson
*Assistant Examiner* — Pamela F Wu
(74) *Attorney, Agent, or Firm* — Chang & Hale LLP

(57) ABSTRACT

Certain aspects relate to systems and techniques for an endoscopic system to access, visualize, and treat pathologies in various organs via natural orifices and lumens of various organs. In one aspect, the system includes an elongate shaft configured for insertion into a urinary tract of a patient. The elongate shaft can include a proximal section, a distal section, a tip portion, and a plurality of pull wires extending along the elongate shaft and terminating at the tip portion of the elongate shaft. The plurality of pull wires may include a first and second pull wire. The first pull wire may be configured to articulate each of the proximal section and the distal section in a first direction. The second pull wire may be configured to articulate the distal section in a second direction independently of the proximal section, the second direction being transverse to the first direction.

19 Claims, 30 Drawing Sheets

(51) Int. Cl.
*A61B 1/05* (2006.01)
*A61B 1/00* (2006.01)
*A61B 34/30* (2016.01)

(52) U.S. Cl.
CPC ............ *A61B 1/00087* (2013.01); *A61B 1/05* (2013.01); *A61B 34/30* (2016.02); *A61B 2034/301* (2016.02)

(58) Field of Classification Search
CPC .................. A61B 1/005; A61B 1/0051; A61B 1/0055–0057; A61B 34/30; A61B 2034/301–303; A61B 2034/305–306; A61B 34/32; A61B 34/35; A61B 34/37; A61B 34/70–71; A61B 2034/715; A61B 1/00147; A61B 1/0016
USPC ........ 600/135, 128, 130, 136–137, 139–142, 600/144, 146, 149
See application file for complete search history.

(56) References Cited

U.S. PATENT DOCUMENTS

| | | |
|---|---|---|
| 4,294,234 A | 10/1981 | Matsuo |
| 4,392,485 A | 7/1983 | Hiltebrandt |
| 4,607,619 A | 8/1986 | Seike et al. |
| 4,690,175 A | 9/1987 | Ouchi et al. |
| 4,706,656 A | 11/1987 | Kubota |
| 4,741,326 A | 5/1988 | Sidall et al. |
| 4,745,908 A | 5/1988 | Wardle |
| 4,748,969 A | 6/1988 | Wardle |
| 4,750,475 A | 6/1988 | Yoshihashi |
| 4,771,766 A | 9/1988 | Aoshiro |
| 4,846,791 A | 7/1989 | Hattler et al. |
| 4,869,238 A | 9/1989 | Opie et al. |
| 4,906,496 A | 3/1990 | Hosono et al. |
| 4,907,168 A | 3/1990 | Boggs |
| 4,967,732 A | 11/1990 | Inoue |
| 5,050,585 A | 9/1991 | Takahashi |
| 5,083,549 A | 1/1992 | Cho et al. |
| 5,106,387 A | 4/1992 | Kittrell et al. |
| 5,108,800 A | 4/1992 | Koo |
| 5,125,909 A | 6/1992 | Heimberger |
| 5,168,864 A | 12/1992 | Shockey |
| 5,199,417 A | 4/1993 | Muller et al. |
| 5,217,002 A | 6/1993 | Katsurada |
| 5,251,611 A | 10/1993 | Zehel et al. |
| 5,257,617 A | 11/1993 | Takahashi |
| 5,261,391 A | 11/1993 | Inoue |
| 5,287,861 A | 2/1994 | Wilk |
| 5,313,934 A | 5/1994 | Wiita et al. |
| 5,381,782 A * | 1/1995 | DeLaRama .......... A61B 1/0056 138/118 |
| 5,386,818 A | 2/1995 | Schneebaum |
| 5,448,988 A | 9/1995 | Watanabe |
| 5,478,330 A | 12/1995 | Imran et al. |
| 5,482,029 A | 1/1996 | Sekiguchi |
| 5,489,270 A | 2/1996 | van Erp |
| 5,507,725 A | 4/1996 | Savage et al. |
| 5,533,985 A | 7/1996 | Wang |
| 5,580,200 A | 12/1996 | Fullerton |
| 5,669,876 A | 9/1997 | Schechter et al. |
| 5,681,296 A | 10/1997 | Ishida |
| 5,704,534 A | 1/1998 | Huitema et al. |
| 5,720,775 A | 2/1998 | Lamard |
| 5,741,429 A | 4/1998 | Donadio, III |
| 5,749,889 A | 5/1998 | Bacich et al. |
| 5,873,817 A | 2/1999 | Kokish et al. |
| 5,876,325 A | 3/1999 | Mizuno et al. |
| 5,879,287 A | 3/1999 | Yoshihashi |
| 5,882,347 A | 3/1999 | Mouris-Laan |
| 5,888,191 A | 3/1999 | Akiba |
| 5,910,129 A | 6/1999 | Koblish et al. |
| 5,938,586 A | 8/1999 | Wilk |
| 5,938,587 A | 8/1999 | Taylor et al. |
| 6,012,494 A | 1/2000 | Balazs |
| 6,143,013 A | 11/2000 | Samson et al. |
| 6,157,853 A | 12/2000 | Blume et al. |
| 6,174,280 B1 | 1/2001 | Oneda |
| 6,197,015 B1 | 3/2001 | Wilson |
| 6,198,974 B1 | 3/2001 | Webster, Jr. |
| 6,234,958 B1 | 5/2001 | Snoke et al. |
| 6,315,715 B1 | 11/2001 | Taylor et al. |
| 6,404,497 B1 | 6/2002 | Backman |
| 6,436,107 B1 | 8/2002 | Wang et al. |
| 6,464,632 B1 | 10/2002 | Taylor |
| 6,485,411 B1 | 11/2002 | Konstorum |
| 6,491,626 B1 | 12/2002 | Stone et al. |
| 6,537,205 B1 | 3/2003 | Smith |
| 6,554,793 B1 | 4/2003 | Pauker et al. |
| 6,716,178 B1 | 4/2004 | Kilpatrick et al. |
| 6,746,422 B1 | 6/2004 | Noriega |
| 6,749,560 B1 | 6/2004 | Konstorum |
| 6,790,173 B2 | 9/2004 | Saadat |
| 6,827,710 B1 | 12/2004 | Mooney |
| 6,827,712 B2 | 12/2004 | Tovey et al. |
| 6,837,846 B2 | 1/2005 | Jaffe |
| 6,837,849 B2 | 1/2005 | Ogura et al. |
| 6,908,428 B2 | 6/2005 | Aizenfeld |
| 6,921,362 B2 | 7/2005 | Ouchi |
| 6,958,035 B2 | 10/2005 | Friedman et al. |
| 7,008,401 B2 | 3/2006 | Thompson et al. |
| 7,130,700 B2 | 10/2006 | Gardeski et al. |
| 7,578,786 B2 | 8/2009 | Boulais et al. |
| 7,594,903 B2 | 9/2009 | Webler et al. |
| 7,621,940 B2 | 11/2009 | Harms et al. |
| 7,645,230 B2 | 1/2010 | Mikkaichi |
| 7,645,231 B2 | 1/2010 | Akiba |
| 7,781,724 B2 | 8/2010 | Childers et al. |
| 7,789,827 B2 | 9/2010 | Landry |
| 7,930,065 B2 | 4/2011 | Larkin et al. |
| 8,046,049 B2 | 10/2011 | Govari et al. |
| 8,052,636 B2 | 11/2011 | Moll et al. |
| 8,114,097 B2 | 2/2012 | Brock et al. |
| 8,246,536 B2 | 8/2012 | Ochi |
| 8,444,637 B2 | 5/2013 | Podmore et al. |
| 8,460,236 B2 | 6/2013 | Roelle et al. |
| 8,498,691 B2 | 7/2013 | Moll et al. |
| 8,515,215 B2 | 8/2013 | Younge et al. |
| 8,652,030 B2 | 2/2014 | Matsuura et al. |
| 8,686,747 B2 | 4/2014 | Berner |
| 8,758,231 B2 | 6/2014 | Bunch et al. |
| 8,827,947 B2 | 9/2014 | Bosman et al. |
| 9,173,713 B2 | 11/2015 | Hart et al. |
| 9,186,046 B2 | 11/2015 | Ramamurthy et al. |
| 9,259,274 B2 | 2/2016 | Prisco |
| 9,302,702 B1 | 4/2016 | Schepmann |
| 9,314,953 B2 | 4/2016 | Lauer |
| 9,427,551 B2 | 8/2016 | Leeflang et al. |
| 9,504,604 B2 | 11/2016 | Alvarez |
| 9,561,083 B2 | 2/2017 | Yu et al. |
| 9,591,990 B2 | 3/2017 | Chen et al. |
| 9,622,827 B2 | 4/2017 | Yu et al. |
| 9,636,184 B2 | 5/2017 | Lee et al. |
| 9,713,509 B2 | 7/2017 | Schuh et al. |
| 9,717,563 B2 | 8/2017 | Tognaccini |
| 9,726,476 B2 | 8/2017 | Ramamurthy et al. |
| 9,727,963 B2 | 8/2017 | Mintz et al. |
| 9,737,371 B2 | 8/2017 | Romo et al. |
| 9,737,373 B2 | 8/2017 | Schuh |
| 9,744,335 B2 | 8/2017 | Jiang |
| 9,763,741 B2 | 9/2017 | Alvarez et al. |
| 9,788,910 B2 | 10/2017 | Schuh |
| 9,839,481 B2 | 12/2017 | Blumenkranz et al. |
| 9,844,353 B2 | 12/2017 | Walker et al. |
| 9,844,412 B2 | 12/2017 | Bogusky et al. |
| 9,867,635 B2 | 1/2018 | Alvarez et al. |
| 9,918,659 B2 | 3/2018 | Chopra |
| 9,918,681 B2 | 3/2018 | Wallace et al. |
| 9,931,025 B1 | 4/2018 | Graetzel et al. |
| 9,949,749 B2 | 4/2018 | Noonan et al. |
| 9,955,986 B2 | 5/2018 | Shah |
| 9,962,228 B2 | 5/2018 | Schuh et al. |
| 9,980,785 B2 | 5/2018 | Schuh |

(56) References Cited

U.S. PATENT DOCUMENTS

| | | |
|---|---|---|
| 9,993,313 B2 | 6/2018 | Schuh et al. |
| 10,016,900 B1 | 7/2018 | Meyer et al. |
| 10,022,192 B1 | 7/2018 | Ummalaneni |
| 10,080,576 B2 | 9/2018 | Romo et al. |
| 10,130,427 B2 | 11/2018 | Tanner et al. |
| 10,136,959 B2 | 11/2018 | Mintz et al. |
| 10,145,747 B1 | 12/2018 | Lin et al. |
| 10,149,720 B2 | 12/2018 | Romo |
| 10,159,532 B1 | 12/2018 | Ummalaneni et al. |
| 10,159,533 B2 | 12/2018 | Moll et al. |
| 10,169,875 B2 | 1/2019 | Mintz et al. |
| 10,213,264 B2 | 2/2019 | Tanner et al. |
| 10,219,874 B2 | 3/2019 | Yu et al. |
| 10,231,793 B2 | 3/2019 | Romo |
| 10,231,867 B2 | 3/2019 | Alvarez et al. |
| 10,244,926 B2 | 4/2019 | Noonan et al. |
| 10,285,574 B2 | 5/2019 | Landey |
| 10,299,870 B2 | 5/2019 | Connolly et al. |
| 10,314,463 B2 | 6/2019 | Agrawal et al. |
| 10,363,103 B2 | 7/2019 | Alvarez et al. |
| 10,376,672 B2 | 8/2019 | Yu |
| 10,383,765 B2 | 8/2019 | Alvarez et al. |
| 10,398,518 B2 | 9/2019 | Yu et al. |
| 10,405,908 B2 | 9/2019 | Redmond et al. |
| 10,405,939 B2 | 9/2019 | Romo et al. |
| 10,405,940 B2 | 9/2019 | Romo |
| 10,426,559 B2 | 10/2019 | Graetzel et al. |
| 10,426,661 B2 | 10/2019 | Kintz |
| 10,434,660 B2 | 10/2019 | Meyer |
| 10,463,439 B2 | 11/2019 | Joseph et al. |
| 10,464,209 B2 | 11/2019 | Ho et al. |
| 10,470,830 B2 | 11/2019 | Hill |
| 10,482,599 B2 | 11/2019 | Mintz et al. |
| 10,493,241 B2 | 12/2019 | Jiang |
| 10,500,001 B2 | 12/2019 | Yu et al. |
| 10,517,692 B2 | 12/2019 | Eyre et al. |
| 10,524,866 B2 | 1/2020 | Srinivasan |
| 10,539,478 B2 | 1/2020 | Lin |
| 10,543,048 B2 | 1/2020 | Noonan et al. |
| 10,555,778 B2 | 2/2020 | Ummalaneni et al. |
| 10,555,780 B2 | 2/2020 | Tanner et al. |
| 10,631,949 B2 | 4/2020 | Schuh et al. |
| 10,639,108 B2 | 5/2020 | Romo et al. |
| 10,639,109 B2 | 5/2020 | Bovay et al. |
| 10,639,114 B2 | 5/2020 | Schuh |
| 10,667,720 B2 | 6/2020 | Wong et al. |
| 10,667,871 B2 | 6/2020 | Romo et al. |
| 10,667,875 B2 | 6/2020 | DeFonzo |
| 10,682,189 B2 | 6/2020 | Schuh et al. |
| 10,702,348 B2 | 7/2020 | Moll et al. |
| 10,716,461 B2 | 7/2020 | Jenkins |
| 10,743,751 B2 | 8/2020 | Landey et al. |
| 10,744,035 B2 | 8/2020 | Alvarez et al. |
| 10,751,140 B2 | 8/2020 | Wallace et al. |
| 10,765,303 B2 | 9/2020 | Graetzel et al. |
| 10,765,487 B2 | 9/2020 | Ho |
| 10,779,898 B2 | 9/2020 | Hill |
| 10,786,329 B2 | 9/2020 | Schuh et al. |
| 10,786,432 B2 | 10/2020 | Mintz et al. |
| 10,792,464 B2 | 10/2020 | Romo et al. |
| 10,792,466 B2 | 10/2020 | Landey et al. |
| 10,820,954 B2 | 11/2020 | Marsot et al. |
| 2001/0004676 A1 | 6/2001 | Ouchi |
| 2002/0128535 A1 | 9/2002 | Kikuchi |
| 2003/0036748 A1 | 2/2003 | Cooper et al. |
| 2003/0130564 A1 | 7/2003 | Martone et al. |
| 2003/0158545 A1 | 8/2003 | Hovda et al. |
| 2003/0163199 A1 | 8/2003 | Chu et al. |
| 2003/0181809 A1 | 9/2003 | Hall et al. |
| 2003/0195664 A1 | 10/2003 | Nowlin et al. |
| 2004/0015122 A1 | 1/2004 | Zhang et al. |
| 2004/0054322 A1 | 3/2004 | Vargas |
| 2004/0072066 A1 | 4/2004 | Cho et al. |
| 2004/0138525 A1 | 7/2004 | Saadat et al. |
| 2004/0193013 A1 | 9/2004 | Isakawa et al. |
| 2004/0199052 A1* | 10/2004 | Banik .................. A61B 1/0051 600/142 |
| 2004/0249246 A1 | 12/2004 | Campos |
| 2005/0004515 A1 | 1/2005 | Hart et al. |
| 2005/0065404 A1* | 3/2005 | Moriyama ............. A61B 1/018 600/146 |
| 2005/0125005 A1 | 6/2005 | Fujikura |
| 2005/0131279 A1 | 6/2005 | Boulais et al. |
| 2005/0154262 A1 | 7/2005 | Banik et al. |
| 2005/0159646 A1 | 7/2005 | Nordstrom et al. |
| 2005/0165366 A1 | 7/2005 | Brustad |
| 2005/0222581 A1 | 10/2005 | Fischer et al. |
| 2005/0234293 A1 | 10/2005 | Yamamoto |
| 2005/0256452 A1 | 11/2005 | DeMarchi |
| 2005/0272975 A1 | 12/2005 | McWeeney et al. |
| 2005/0273085 A1 | 12/2005 | Hinman et al. |
| 2005/0288549 A1 | 12/2005 | Mathis |
| 2006/0025749 A1 | 2/2006 | Moenning |
| 2006/0041188 A1 | 2/2006 | Dirusso et al. |
| 2006/0111692 A1 | 5/2006 | Hlavka et al. |
| 2006/0241368 A1 | 10/2006 | Fichtinger et al. |
| 2006/0264708 A1 | 11/2006 | Horne |
| 2006/0276827 A1 | 12/2006 | Mitelberg et al. |
| 2007/0060879 A1 | 3/2007 | Weitzner et al. |
| 2007/0112355 A1 | 5/2007 | Salahieh |
| 2007/0135733 A1 | 6/2007 | Soukup et al. |
| 2007/0135763 A1 | 6/2007 | Musbach et al. |
| 2007/0135803 A1 | 6/2007 | Belson |
| 2007/0156019 A1 | 7/2007 | Larkin et al. |
| 2007/0232856 A1 | 10/2007 | Ueno |
| 2007/0270645 A1 | 11/2007 | Ikeda |
| 2007/0270679 A1 | 11/2007 | Nguyen et al. |
| 2007/0282167 A1 | 12/2007 | Barenboym et al. |
| 2007/0287886 A1 | 12/2007 | Saadat |
| 2008/0039255 A1 | 2/2008 | Jinno |
| 2008/0046122 A1 | 2/2008 | Manzo et al. |
| 2008/0051629 A1 | 2/2008 | Sugiyama et al. |
| 2008/0065103 A1 | 3/2008 | Cooper et al. |
| 2008/0097293 A1 | 4/2008 | Chin et al. |
| 2008/0108869 A1 | 5/2008 | Sanders et al. |
| 2008/0139887 A1 | 6/2008 | Fitpatrick |
| 2008/0140087 A1 | 6/2008 | Barbagli et al. |
| 2008/0146874 A1 | 6/2008 | Miller |
| 2008/0147089 A1 | 6/2008 | Loh |
| 2008/0177285 A1 | 7/2008 | Brock et al. |
| 2008/0208001 A1 | 8/2008 | Hadani |
| 2008/0212082 A1 | 9/2008 | Froggatt et al. |
| 2008/0218770 A1 | 9/2008 | Moll et al. |
| 2009/0062611 A1 | 3/2009 | Toyama |
| 2009/0099420 A1 | 4/2009 | Woodley |
| 2009/0163851 A1 | 6/2009 | Holloway |
| 2009/0247880 A1 | 10/2009 | Naruse et al. |
| 2009/0254083 A1 | 10/2009 | Wallace et al. |
| 2009/0259099 A1 | 10/2009 | Zhou et al. |
| 2009/0275934 A1 | 11/2009 | Baxter et al. |
| 2009/0299344 A1 | 12/2009 | Lee et al. |
| 2009/0306587 A1 | 12/2009 | Milijasevic et al. |
| 2010/0030023 A1 | 2/2010 | Yoshie |
| 2010/0073150 A1 | 3/2010 | Olson et al. |
| 2010/0082041 A1 | 4/2010 | Prisco |
| 2010/0114115 A1 | 5/2010 | Schlesinger et al. |
| 2010/0130823 A1 | 5/2010 | Ando |
| 2010/0168918 A1 | 7/2010 | Zhao |
| 2010/0198170 A1 | 8/2010 | Umeda et al. |
| 2010/0204713 A1 | 8/2010 | Ruiz |
| 2010/0217184 A1 | 8/2010 | Koblish et al. |
| 2010/0228266 A1 | 9/2010 | Hourtash |
| 2010/0234831 A1 | 9/2010 | Hinman et al. |
| 2010/0249497 A1 | 9/2010 | Peine et al. |
| 2010/0249506 A1 | 9/2010 | Prisco et al. |
| 2011/0009863 A1 | 1/2011 | Stanislaw |
| 2011/0015484 A1 | 1/2011 | Alvarez et al. |
| 2011/0034772 A1* | 2/2011 | Konstorum ............ A61B 1/008 600/142 |
| 2011/0046441 A1 | 2/2011 | Wiltshire et al. |
| 2011/0077681 A1 | 3/2011 | Nagano |
| 2011/0098533 A1 | 4/2011 | Onoda |
| 2011/0130718 A1 | 6/2011 | Kidd et al. |
| 2011/0148442 A1 | 6/2011 | Berner |

(56) References Cited

U.S. PATENT DOCUMENTS

| | | |
|---|---|---|
| 2011/0152880 A1 | 6/2011 | Alvarez et al. |
| 2011/0245844 A1 | 10/2011 | Jinno et al. |
| 2011/0261183 A1 | 10/2011 | Ma et al. |
| 2011/0277775 A1* | 11/2011 | Holop .................. H01F 5/02 128/849 |
| 2011/0306836 A1 | 12/2011 | Ohline et al. |
| 2012/0071894 A1 | 3/2012 | Tanner et al. |
| 2012/0071895 A1 | 3/2012 | Stabler et al. |
| 2012/0123327 A1 | 5/2012 | Miller |
| 2012/0136419 A1 | 5/2012 | Zarembo et al. |
| 2012/0143226 A1 | 6/2012 | Belson et al. |
| 2012/0190976 A1 | 7/2012 | Kleinstreuer |
| 2012/0191107 A1 | 7/2012 | Tanner et al. |
| 2012/0221007 A1 | 8/2012 | Batten et al. |
| 2012/0239012 A1 | 9/2012 | Laurent et al. |
| 2012/0239060 A1 | 9/2012 | Orban, III |
| 2012/0259244 A1 | 10/2012 | Roberts et al. |
| 2012/0283747 A1 | 11/2012 | Popovic |
| 2012/0289777 A1 | 11/2012 | Chopra |
| 2012/0302869 A1 | 11/2012 | Koyrakh |
| 2013/0018400 A1 | 1/2013 | Milton et al. |
| 2013/0030519 A1 | 1/2013 | Tran et al. |
| 2013/0035537 A1 | 2/2013 | Wallace et al. |
| 2013/0041224 A1* | 2/2013 | Okaniwa .............. A61B 1/0056 600/142 |
| 2013/0090552 A1 | 4/2013 | Ramamurthy et al. |
| 2013/0109957 A1 | 5/2013 | Hooft et al. |
| 2013/0123580 A1 | 5/2013 | Peters |
| 2013/0144116 A1 | 6/2013 | Cooper et al. |
| 2013/0165854 A1 | 6/2013 | Sandhu et al. |
| 2013/0165908 A1 | 6/2013 | Purdy et al. |
| 2013/0204124 A1 | 8/2013 | Duindam |
| 2013/0209208 A1 | 8/2013 | Bailey |
| 2013/0218005 A1 | 8/2013 | Desai |
| 2013/0226151 A1 | 8/2013 | Suehara |
| 2013/0274783 A1 | 10/2013 | Wynberg |
| 2013/0303892 A1 | 11/2013 | Zhao |
| 2013/0304091 A1 | 11/2013 | Straehnz |
| 2013/0317276 A1 | 11/2013 | D'Andrea |
| 2013/0317519 A1 | 11/2013 | Romo et al. |
| 2013/0345519 A1 | 12/2013 | Piskun et al. |
| 2014/0001235 A1 | 1/2014 | Shelton, IV |
| 2014/0012288 A1 | 1/2014 | Darisse |
| 2014/0046313 A1 | 2/2014 | Pederson et al. |
| 2014/0142591 A1 | 5/2014 | Alvarez et al. |
| 2014/0200402 A1 | 7/2014 | Snoke et al. |
| 2014/0235943 A1 | 8/2014 | Paris |
| 2014/0257333 A1 | 9/2014 | Blumenkranz |
| 2014/0276594 A1 | 9/2014 | Tanner et al. |
| 2014/0309625 A1 | 10/2014 | Okamoto et al. |
| 2014/0316397 A1 | 10/2014 | Brown |
| 2014/0343416 A1 | 11/2014 | Panescu |
| 2014/0357984 A1 | 12/2014 | Wallace et al. |
| 2015/0031950 A1 | 1/2015 | Drontle et al. |
| 2015/0045621 A1* | 2/2015 | Masaki .................. F16D 11/00 600/152 |
| 2015/0119645 A1 | 4/2015 | Baldwin |
| 2015/0150636 A1 | 6/2015 | Hagn et al. |
| 2015/0255782 A1 | 9/2015 | Kim et al. |
| 2015/0305650 A1 | 10/2015 | Hunter |
| 2015/0311838 A1 | 10/2015 | Moule |
| 2016/0000414 A1 | 1/2016 | Brown |
| 2016/0007881 A1 | 1/2016 | Wong et al. |
| 2016/0067450 A1 | 3/2016 | Kowshik |
| 2016/0082225 A1* | 3/2016 | Kobayashi ........ A61M 25/0013 604/523 |
| 2016/0166320 A1 | 6/2016 | Ciulla |
| 2016/0183841 A1 | 6/2016 | Duindam |
| 2016/0227982 A1 | 8/2016 | Takahashi |
| 2016/0270865 A1 | 9/2016 | Landey et al. |
| 2016/0287054 A1* | 10/2016 | Fujitani .............. A61B 1/00009 |
| 2016/0287279 A1 | 10/2016 | Bovay et al. |
| 2016/0287346 A1 | 10/2016 | Hyodo et al. |
| 2016/0346049 A1 | 12/2016 | Allen et al. |
| 2016/0372743 A1 | 12/2016 | Cho et al. |
| 2016/0374541 A1 | 12/2016 | Agrawal et al. |
| 2017/0007337 A1 | 1/2017 | Dan |
| 2017/0065153 A1* | 3/2017 | Fujitani .................. A61B 1/008 |
| 2017/0106904 A1 | 4/2017 | Hanson |
| 2017/0135718 A1 | 5/2017 | Lyons |
| 2017/0209162 A1 | 6/2017 | Sperry |
| 2017/0189118 A1 | 7/2017 | Chopra |
| 2017/0202627 A1 | 7/2017 | Sramek et al. |
| 2017/0209073 A1 | 7/2017 | Sramek et al. |
| 2017/0224192 A1* | 8/2017 | Seto .................. A61B 1/00 |
| 2017/0231647 A1 | 8/2017 | Saunders |
| 2017/0245854 A1 | 8/2017 | Zemlok |
| 2017/0281218 A1 | 10/2017 | Timm |
| 2017/0290631 A1 | 10/2017 | Lee et al. |
| 2017/0326337 A1 | 11/2017 | Romascanu |
| 2018/0025666 A1 | 1/2018 | Ho et al. |
| 2018/0169671 A1 | 6/2018 | Winter |
| 2018/0214011 A1 | 8/2018 | Graetzel et al. |
| 2018/0221038 A1 | 8/2018 | Noonan et al. |
| 2018/0221039 A1 | 8/2018 | Shah |
| 2018/0279852 A1 | 10/2018 | Rafii-Tari et al. |
| 2018/0289394 A1 | 10/2018 | Shah |
| 2018/0289431 A1 | 10/2018 | Draper et al. |
| 2018/0325499 A1 | 11/2018 | Landey et al. |
| 2018/0360435 A1 | 12/2018 | Romo |
| 2019/0000559 A1 | 1/2019 | Berman et al. |
| 2019/0000560 A1 | 1/2019 | Berman et al. |
| 2019/0000576 A1 | 1/2019 | Mintz et al. |
| 2019/0110839 A1 | 4/2019 | Rafii-Tari et al. |
| 2019/0151148 A1 | 4/2019 | Alvarez et al. |
| 2019/0167366 A1 | 6/2019 | Ummalaneni |
| 2019/0175009 A1 | 6/2019 | Mintz |
| 2019/0175062 A1 | 6/2019 | Rafii-Tari et al. |
| 2019/0175799 A1 | 6/2019 | Hsu |
| 2019/0183585 A1 | 6/2019 | Rafii-Tari et al. |
| 2019/0183587 A1 | 6/2019 | Rafii-Tari et al. |
| 2019/0216548 A1 | 7/2019 | Ummalaneni |
| 2019/0216576 A1 | 7/2019 | Eyre |
| 2019/0223974 A1 | 7/2019 | Romo |
| 2019/0246877 A1* | 8/2019 | Mitsuya .............. A61B 1/0057 |
| 2019/0262086 A1 | 8/2019 | Connolly et al. |
| 2019/0269468 A1 | 9/2019 | Hsu et al. |
| 2019/0274764 A1 | 9/2019 | Romo |
| 2019/0290109 A1 | 9/2019 | Agrawal et al. |
| 2019/0298160 A1 | 10/2019 | Ummalaneni et al. |
| 2019/0298460 A1 | 10/2019 | Al-Jadda |
| 2019/0298465 A1 | 10/2019 | Chin |
| 2019/0307987 A1 | 10/2019 | Yu |
| 2019/0336238 A1 | 11/2019 | Yu |
| 2019/0365201 A1 | 12/2019 | Noonan et al. |
| 2019/0365209 A1 | 12/2019 | Ye et al. |
| 2019/0365479 A1 | 12/2019 | Rafii-Tari |
| 2019/0365486 A1 | 12/2019 | Srinivasan et al. |
| 2019/0375383 A1 | 12/2019 | Alvarez |
| 2019/0380787 A1 | 12/2019 | Ye |
| 2019/0380797 A1 | 12/2019 | Yu |
| 2020/0000533 A1 | 1/2020 | Schuh |
| 2020/0038123 A1 | 2/2020 | Graetzel |
| 2020/0038128 A1 | 2/2020 | Joseph |
| 2020/0039086 A1 | 2/2020 | Meyer |
| 2020/0046434 A1 | 2/2020 | Graetzel |
| 2020/0046942 A1 | 2/2020 | Alvarez |
| 2020/0054408 A1 | 2/2020 | Schuh et al. |
| 2020/0060516 A1 | 2/2020 | Baez |
| 2020/0085516 A1 | 3/2020 | DeFonzo |
| 2020/0093549 A1 | 3/2020 | Chin |
| 2020/0093554 A1 | 3/2020 | Schuh |
| 2020/0100845 A1 | 4/2020 | Julian |
| 2020/0100855 A1 | 4/2020 | Leparmentier |
| 2020/0101264 A1 | 4/2020 | Jiang |
| 2020/0107894 A1 | 4/2020 | Wallace |
| 2020/0121502 A1 | 4/2020 | Kintz |
| 2020/0146769 A1 | 5/2020 | Eyre |
| 2020/0170720 A1 | 6/2020 | Ummalaneni |
| 2020/0171660 A1 | 6/2020 | Ho |
| 2020/0188043 A1 | 6/2020 | Yu |
| 2020/0197112 A1 | 6/2020 | Chin |
| 2020/0206472 A1 | 7/2020 | Ma |
| 2020/0217733 A1 | 7/2020 | Lin |

(56) References Cited

U.S. PATENT DOCUMENTS

| | | | |
|---|---|---|---|
| 2020/0222134 A1 | 7/2020 | Schuh | |
| 2020/0237189 A1* | 7/2020 | Do | A61B 1/0057 |
| 2020/0237458 A1 | 7/2020 | DeFonzo | |
| 2020/0261172 A1 | 8/2020 | Romo | |
| 2020/0268459 A1 | 8/2020 | Noonan et al. | |
| 2020/0268460 A1 | 8/2020 | Tse | |
| 2020/0281787 A1 | 9/2020 | Ruiz | |
| 2020/0297437 A1 | 9/2020 | Schuh | |
| 2020/0297444 A1 | 9/2020 | Camarillo | |
| 2020/0305922 A1 | 10/2020 | Schuh | |
| 2020/0305983 A1 | 10/2020 | Yampolsky | |
| 2020/0305989 A1 | 10/2020 | Schuh | |
| 2020/0305992 A1 | 10/2020 | Schuh | |
| 2020/0315717 A1 | 10/2020 | Bovay | |
| 2020/0315723 A1 | 10/2020 | Hassan | |
| 2020/0323596 A1 | 10/2020 | Moll | |
| 2020/0330167 A1 | 10/2020 | Romo | |
| 2020/0337593 A1 | 10/2020 | Wong | |
| 2020/0345216 A1 | 11/2020 | Jenkins | |
| 2020/0352420 A1 | 11/2020 | Graetzel | |
| 2020/0360183 A1 | 11/2020 | Alvarez | |
| 2020/0367726 A1 | 11/2020 | Landey et al. | |
| 2020/0367981 A1 | 11/2020 | Ho et al. | |
| 2020/0375678 A1 | 12/2020 | Wallace | |
| 2020/0405317 A1 | 12/2020 | Wallace | |
| 2020/0405411 A1 | 12/2020 | Draper et al. | |
| 2020/0405419 A1 | 12/2020 | Mao | |
| 2020/0405420 A1 | 12/2020 | Purohit | |
| 2020/0405423 A1 | 12/2020 | Schuh | |
| 2020/0405424 A1 | 12/2020 | Schuh | |
| 2020/0405434 A1 | 12/2020 | Schuh | |
| 2020/0406002 A1 | 12/2020 | Romo | |
| 2021/0007819 A1 | 1/2021 | Schuh | |
| 2021/0008341 A1 | 1/2021 | Landey et al. | |
| 2021/0023340 A1 | 1/2021 | Jiang | |
| 2021/0030501 A1 | 2/2021 | Eyre | |

FOREIGN PATENT DOCUMENTS

| | | |
|---|---|---|
| CN | 102316817 | 1/2012 |
| CN | 102458295 | 5/2012 |
| CN | 102665590 | 9/2012 |
| CN | 102711586 | 10/2012 |
| CN | 102973317 | 3/2013 |
| CN | 103767659 | 5/2014 |
| CN | 103930063 | 7/2014 |
| EP | 0 543 539 | 5/1993 |
| EP | 0 776 739 | 6/1997 |
| EP | 1 442 720 | 8/2004 |
| EP | 0 904 796 | 11/2004 |
| EP | 2 615 992 | 7/2016 |
| JP | 2006-525087 | 11/2006 |
| JP | 2007-511247 | 5/2007 |
| JP | 2010-046384 | 3/2010 |
| JP | 2011-015992 | 1/2011 |
| JP | 2012-105793 | 6/2012 |
| KR | 10-2012-0028100 | 3/2012 |
| WO | WO 94/14494 | 7/1994 |
| WO | WO 00/67640 | 11/2000 |
| WO | WO 02/74178 | 9/2002 |
| WO | WO 04/039273 | 5/2004 |
| WO | WO 04/105849 | 12/2004 |
| WO | WO 05/032637 | 4/2005 |
| WO | WO 05/081202 | 9/2005 |
| WO | WO 09/097461 | 6/2007 |
| WO | WO 07/088208 | 8/2007 |
| WO | WO 07/146987 | 12/2007 |
| WO | WO 08/097540 | 8/2008 |
| WO | WO 09/092059 | 7/2009 |
| WO | WO 10/081187 | 7/2010 |
| WO | WO 10/127162 | 11/2010 |
| WO | WO 11/002215 | 1/2011 |
| WO | WO 11/005335 | 1/2011 |
| WO | WO 12/082719 | 6/2012 |
| WO | WO 13/107468 | 7/2013 |
| WO | WO 15/093602 | 12/2013 |
| WO | WO 16/003052 | 1/2016 |
| WO | WO 17/048194 | 3/2017 |
| WO | WO 17/053698 | 3/2017 |
| WO | WO 18/098477 | 5/2018 |
| WO | WO 19/05992 | 1/2019 |

* cited by examiner

MEDICAL DEVICE HAVING MULTIPLE BENDING SECTIONS

CROSS-REFERENCE TO RELATED APPLICATION(S)

This application claims the benefit of U.S. Provisional Application No. 62/887,560, filed Aug. 15, 2019, which is hereby incorporated by reference in its entirety.

TECHNICAL FIELD

Systems and methods disclosed herein relate to medical systems and procedures, and more particularly to a medical device having multiple bending sections.

BACKGROUND

Medical procedures, such as endoscopy, may involve accessing and visualizing the inside of a patient's anatomy for diagnostic and/or therapeutic purposes. For example, urology, or ureteroscopy may involve medical procedures that allow a physician to examine patient lumens, such as the ureter, or organs, such as the kidney. During these procedures, a thin, flexible tubular tool or instrument, known as an endoscope, is inserted into the patient through an orifice (such as a natural orifice) and advanced towards a tissue site identified for subsequent diagnosis and/or treatment. The medical instrument can be controllable and articulable to facilitate navigation through the anatomy.

BRIEF DESCRIPTION OF THE DRAWINGS

The disclosed aspects will hereinafter be described in conjunction with the appended drawings, provided to illustrate and not to limit the disclosed aspects, wherein like designations denote like elements.

DETAILED DESCRIPTION

1. Overview.

Aspects of the present disclosure may be integrated into a robotically-enabled medical system capable of performing a variety of medical procedures, including both minimally invasive, such as laparoscopy, and non-invasive, such as endoscopy, procedures. Among endoscopic procedures, the system may be capable of performing bronchoscopy, ureteroscopy, gastroscopy, etc.

In addition to performing the breadth of procedures, the system may provide additional benefits, such as enhanced imaging and guidance to assist the physician. Additionally, the system may provide the physician with the ability to perform the procedure from an ergonomic position without the need for awkward arm motions and positions. Still further, the system may provide the physician with the ability to perform the procedure with improved ease of use such that one or more of the instruments of the system can be controlled by a single user.

Various embodiments will be described below in conjunction with the drawings for purposes of illustration. It should be appreciated that many other implementations of the disclosed concepts are possible, and various advantages can be achieved with the disclosed implementations. Headings are included herein for reference and to aid in locating various sections. These headings are not intended to limit the scope of the concepts described with respect thereto. Such concepts may have applicability throughout the entire specification.

A. Robotic System—Cart.

Figure 1:
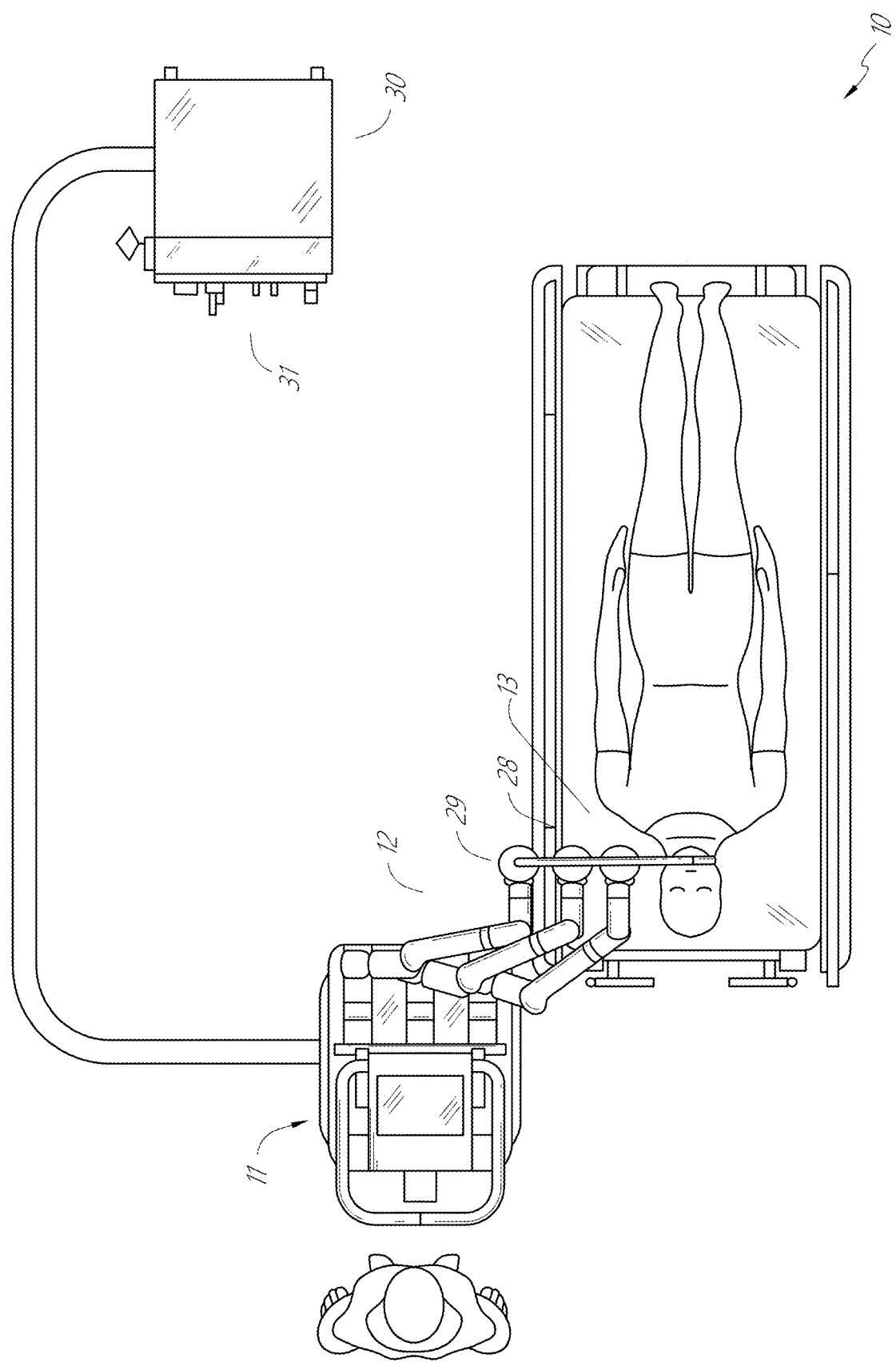
FIG. 1 illustrates an embodiment of a cart-based robotic system arranged for diagnostic and/or therapeutic bronchoscopy.
Figure 2:
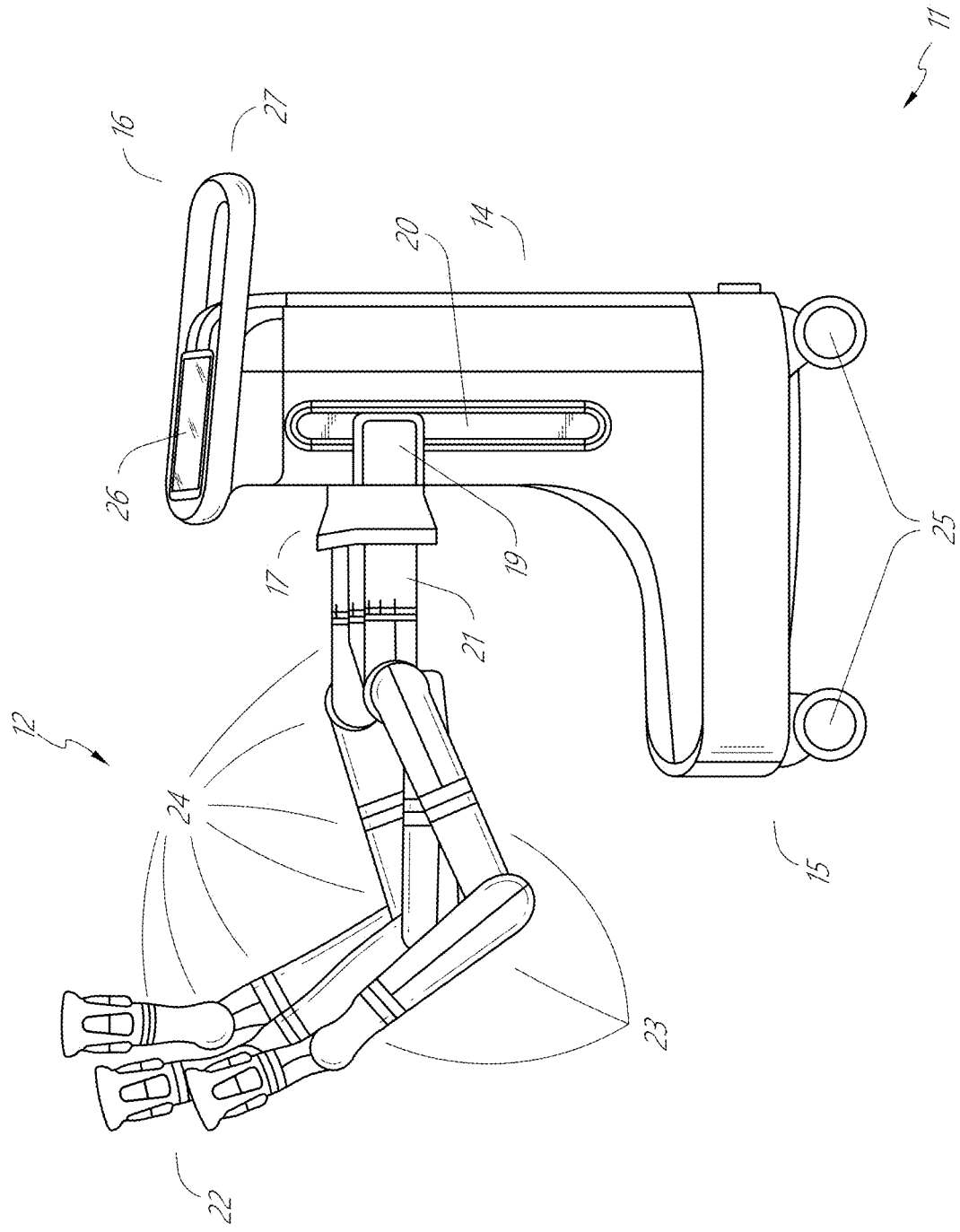
FIG. 2 depicts further aspects of the robotic system of FIG. 1.

The robotically-enabled medical system may be configured in a variety of ways depending on the particular procedure. FIG. 1 illustrates an embodiment of a cart-based robotically-enabled system 10 arranged for a diagnostic and/or therapeutic bronchoscopy. During a bronchoscopy, the system 10 may comprise a cart 11 having one or more robotic arms 12 to deliver a medical instrument, such as a steerable endoscope 13, which may be a procedure-specific bronchoscope for bronchoscopy, to a natural orifice access point (i.e., the mouth of the patient positioned on a table in the present example) to deliver diagnostic and/or therapeutic tools. As shown, the cart 11 may be positioned proximate to the patient's upper torso in order to provide access to the access point. Similarly, the robotic arms 12 may be actuated to position the bronchoscope relative to the access point. The arrangement in FIG. 1 may also be utilized when performing a gastro-intestinal (GI) procedure with a gastroscope, a specialized endoscope for GI procedures. FIG. 2 depicts an example embodiment of the cart in greater detail.

With continued reference to FIG. 1, once the cart 11 is properly positioned, the robotic arms 12 may insert the steerable endoscope 13 into the patient robotically, manually, or a combination thereof. As shown, the steerable endoscope 13 may comprise at least two telescoping parts, such as an inner leader portion and an outer sheath portion, each portion coupled to a separate instrument driver from the set of instrument drivers 28, each instrument driver coupled to the distal end of an individual robotic arm. This linear arrangement of the instrument drivers 28, which facilitates coaxially aligning the leader portion with the sheath portion, creates a "virtual rail" 29 that may be repositioned in space by manipulating the one or more robotic arms 12 into different angles and/or positions. The virtual rails described herein are depicted in the Figures using dashed lines, and accordingly the dashed lines do not depict any physical structure of the system. Translation of the instrument drivers 28 along the virtual rail 29 telescopes the inner leader portion relative to the outer sheath portion or advances or retracts the endoscope 13 from the patient. The angle of the virtual rail 29 may be adjusted, translated, and pivoted based on clinical application or physician preference. For example, in bronchoscopy, the angle and position of the virtual rail 29 as shown represents a compromise between providing physician access to the endoscope 13 while minimizing friction that results from bending the endoscope 13 into the patient's mouth.

The endoscope 13 may be directed down the patient's trachea and lungs after insertion using precise commands from the robotic system until reaching the target destination or operative site. In order to enhance navigation through the patient's lung network and/or reach the desired target, the endoscope 13 may be manipulated to telescopically extend the inner leader portion from the outer sheath portion to obtain enhanced articulation and greater bend radius. The use of separate instrument drivers 28 also allows the leader portion and sheath portion to be driven independently of each other.

For example, the endoscope 13 may be directed to deliver a biopsy needle to a target, such as, for example, a lesion or nodule within the lungs of a patient. The needle may be deployed down a working channel that runs the length of the endoscope to obtain a tissue sample to be analyzed by a pathologist. Depending on the pathology results, additional tools may be deployed down the working channel of the endoscope for additional biopsies. After identifying a nodule to be malignant, the endoscope 13 may endoscopically deliver tools to resect the potentially cancerous tissue. In some instances, diagnostic and therapeutic treatments can be delivered in separate procedures. In those circumstances, the endoscope 13 may also be used to deliver a fiducial to "mark" the location of the target nodule as well. In other instances, diagnostic and therapeutic treatments may be delivered during the same procedure.

The system 10 may also include a movable tower 30, which may be connected via support cables to the cart 11 to provide support for controls, electronics, fluidics, optics, sensors, and/or power to the cart 11. Placing such functionality in the tower 30 allows for a smaller form factor cart 11 that may be more easily adjusted and/or re-positioned by an operating physician and his/her staff. Additionally, the division of functionality between the cart/table and the support tower 30 reduces operating room clutter and facilitates improving clinical workflow. While the cart 11 may be positioned close to the patient, the tower 30 may be stowed in a remote location to stay out of the way during a procedure.

In support of the robotic systems described above, the tower 30 may include component(s) of a computer-based control system that stores computer program instructions, for example, within a non-transitory computer-readable storage medium such as a persistent magnetic storage drive, solid state drive, etc. The execution of those instructions, whether the execution occurs in the tower 30 or the cart 11, may control the entire system or sub-system(s) thereof. For example, when executed by a processor of the computer system, the instructions may cause the components of the robotics system to actuate the relevant carriages and arm mounts, actuate the robotics arms, and control the medical instruments. For example, in response to receiving the control signal, the motors in the joints of the robotics arms may position the arms into a certain posture.

The tower 30 may also include a pump, flow meter, valve control, and/or fluid access in order to provide controlled irrigation and aspiration capabilities to the system that may be deployed through the endoscope 13. These components may also be controlled using the computer system of the tower 30. In some embodiments, irrigation and aspiration capabilities may be delivered directly to the endoscope 13 through separate cable(s).

The tower 30 may include a voltage and surge protector designed to provide filtered and protected electrical power to the cart 11, thereby avoiding placement of a power transformer and other auxiliary power components in the cart 11, resulting in a smaller, more moveable cart 11.

The tower 30 may also include support equipment for the sensors deployed throughout the robotic system 10. For example, the tower 30 may include optoelectronics equipment for detecting, receiving, and processing data received from the optical sensors or cameras throughout the robotic system 10. In combination with the control system, such optoelectronics equipment may be used to generate real-time images for display in any number of consoles deployed throughout the system, including in the tower 30. Similarly, the tower 30 may also include an electronic subsystem for receiving and processing signals received from deployed electromagnetic (EM) sensors. The tower 30 may also be used to house and position an EM field generator for detection by EM sensors in or on the medical instrument.

The tower 30 may also include a console 31 in addition to other consoles available in the rest of the system, e.g., console mounted on top of the cart. The console 31 may include a user interface and a display screen, such as a touchscreen, for the physician operator. Consoles in the system 10 are generally designed to provide both robotic controls as well as preoperative and real-time information of the procedure, such as navigational and localization information of the endoscope 13. When the console 31 is not the only console available to the physician, it may be used by a second operator, such as a nurse, to monitor the health or vitals of the patient and the operation of the system 10, as well as to provide procedure-specific data, such as navigational and localization information. In other embodiments, the console 30 is housed in a body that is separate from the tower 30.

The tower 30 may be coupled to the cart 11 and endoscope 13 through one or more cables or connections (not shown). In some embodiments, the support functionality from the tower 30 may be provided through a single cable to the cart 11, simplifying and de-cluttering the operating room. In other embodiments, specific functionality may be coupled in separate cabling and connections. For example, while power may be provided through a single power cable to the cart 11, the support for controls, optics, fluidics, and/or navigation may be provided through a separate cable.

FIG. 2 provides a detailed illustration of an embodiment of the cart 11 from the cart-based robotically-enabled system shown in FIG. 1. The cart 11 generally includes an elongated support structure 14 (often referred to as a "column"), a cart base 15, and a console 16 at the top of the column 14. The column 14 may include one or more carriages, such as a carriage 17 (alternatively "arm support") for supporting the deployment of one or more robotic arms 12 (three shown in FIG. 2). The carriage 17 may include individually configurable arm mounts that rotate along a perpendicular axis to adjust the base of the robotic arms 12 for better positioning relative to the patient. The carriage 17 also includes a carriage interface 19 that allows the carriage 17 to vertically translate along the column 14.

The carriage interface 19 is connected to the column 14 through slots, such as slot 20, that are positioned on opposite sides of the column 14 to guide the vertical translation of the carriage 17. The slot 20 contains a vertical translation interface to position and hold the carriage 17 at various vertical heights relative to the cart base 15. Vertical translation of the carriage 17 allows the cart 11 to adjust the reach of the robotic arms 12 to meet a variety of table heights, patient sizes, and physician preferences. Similarly, the individually configurable arm mounts on the carriage 17 allow the robotic arm base 21 of the robotic arms 12 to be angled in a variety of configurations.

In some embodiments, the slot 20 may be supplemented with slot covers that are flush and parallel to the slot surface to prevent dirt and fluid ingress into the internal chambers of the column 14 and the vertical translation interface as the carriage 17 vertically translates. The slot covers may be deployed through pairs of spring spools positioned near the vertical top and bottom of the slot 20. The covers are coiled within the spools until deployed to extend and retract from their coiled state as the carriage 17 vertically translates up and down. The spring-loading of the spools provides force to retract the cover into a spool when the carriage 17 translates towards the spool, while also maintaining a tight seal when the carriage 17 translates away from the spool. The covers may be connected to the carriage 17 using, for example, brackets in the carriage interface 19 to ensure proper extension and retraction of the cover as the carriage 17 translates.

The column 14 may internally comprise mechanisms, such as gears and motors, that are designed to use a vertically aligned lead screw to translate the carriage 17 in a mechanized fashion in response to control signals generated in response to user inputs, e.g., inputs from the console 16.

The robotic arms 12 may generally comprise robotic arm bases 21 and end effectors 22, separated by a series of linkages 23 that are connected by a series of joints 24, each joint comprising an independent actuator, each actuator comprising an independently controllable motor. Each independently controllable joint represents an independent degree of freedom available to the robotic arm 12. Each of the robotic arms 12 may have seven joints, and thus provide seven degrees of freedom. A multitude of joints result in a multitude of degrees of freedom, allowing for "redundant" degrees of freedom. Having redundant degrees of freedom allows the robotic arms 12 to position their respective end effectors 22 at a specific position, orientation, and trajectory in space using different linkage positions and joint angles. This allows for the system to position and direct a medical instrument from a desired point in space while allowing the physician to move the arm joints into a clinically advantageous position away from the patient to create greater access, while avoiding arm collisions.

The cart base 15 balances the weight of the column 14, carriage 17, and robotic arms 12 over the floor. Accordingly, the cart base 15 houses heavier components, such as electronics, motors, power supply, as well as components that either enable movement and/or immobilize the cart 11. For example, the cart base 15 includes rollable wheel-shaped casters 25 that allow for the cart 11 to easily move around the room prior to a procedure. After reaching the appropriate position, the casters 25 may be immobilized using wheel locks to hold the cart 11 in place during the procedure.

Positioned at the vertical end of the column 14, the console 16 allows for both a user interface for receiving user input and a display screen (or a dual-purpose device such as, for example, a touchscreen 26) to provide the physician user with both preoperative and intraoperative data. Potential preoperative data on the touchscreen 26 may include preoperative plans, navigation and mapping data derived from preoperative computerized tomography (CT) scans, and/or notes from preoperative patient interviews. Intraoperative data on display may include optical information provided from the tool, sensor and coordinate information from sensors, as well as vital patient statistics, such as respiration, heart rate, and/or pulse. The console 16 may be positioned and tilted to allow a physician to access the console 16 from the side of the column 14 opposite the carriage 17. From this position, the physician may view the console 16, robotic arms 12, and patient while operating the console 16 from behind the cart 11. As shown, the console 16 also includes a handle 27 to assist with maneuvering and stabilizing the cart 11.

Figure 3:
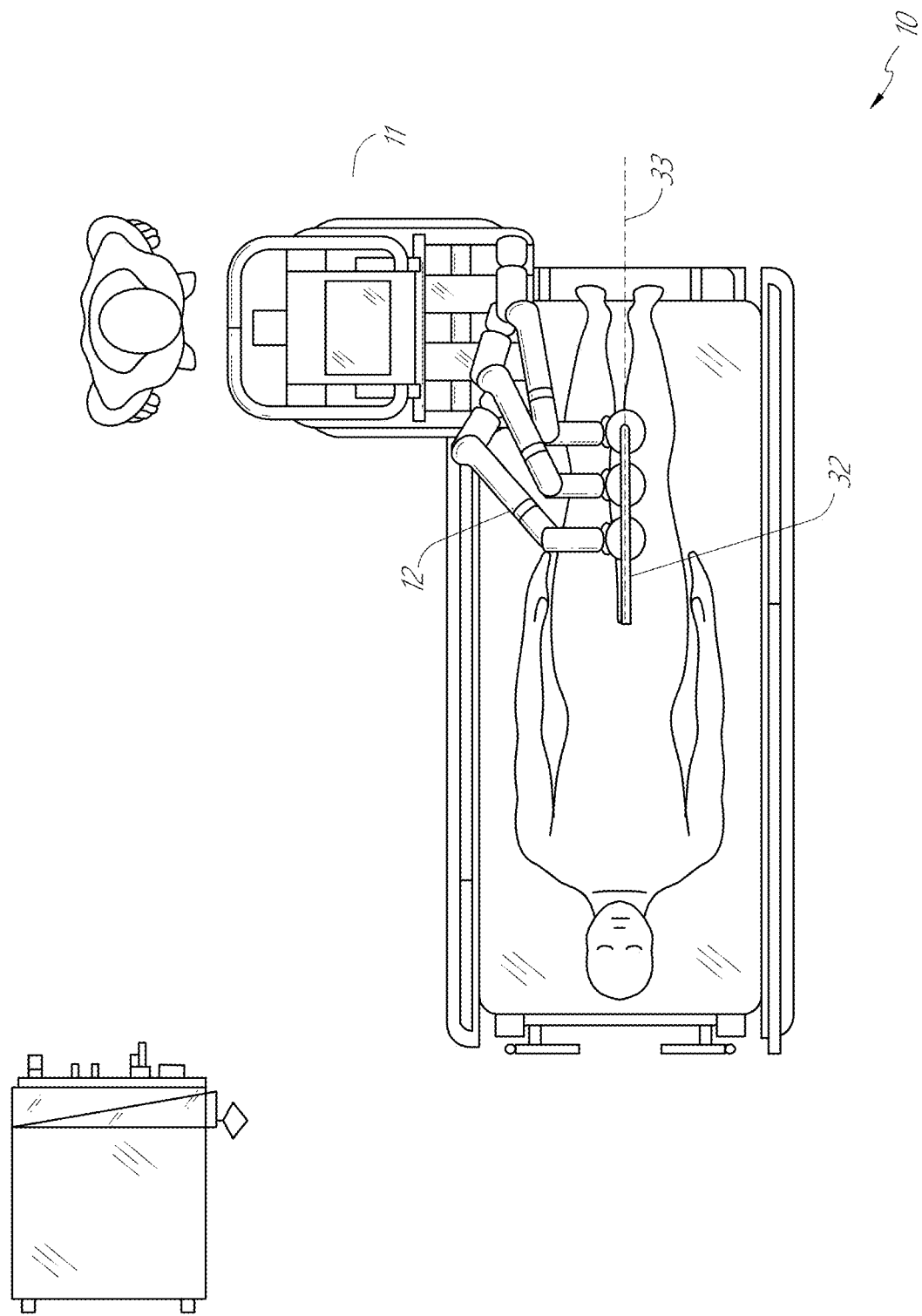
FIG. 3 illustrates an embodiment of the robotic system of FIG. 1 arranged for ureteroscopy.

FIG. 3 illustrates an embodiment of a robotically-enabled system 10 arranged for ureteroscopy. In a ureteroscopic procedure, the cart 11 may be positioned to deliver a ureteroscope 32, a procedure-specific endoscope designed to traverse a patient's urethra and ureter, to the lower abdominal area of the patient. In a ureteroscopy, it may be desirable for the ureteroscope 32 to be directly aligned with the patient's urethra to reduce friction and forces on the sensitive anatomy in the area. As shown, the cart 11 may be aligned at the foot of the table to allow the robotic arms 12 to position the ureteroscope 32 for direct linear access to the patient's urethra. From the foot of the table, the robotic arms 12 may insert the ureteroscope 32 along the virtual rail 33 directly into the patient's lower abdomen through the urethra.

After insertion into the urethra, using similar control techniques as in bronchoscopy, the ureteroscope 32 may be navigated into the bladder, ureters, and/or kidneys for diagnostic and/or therapeutic applications. For example, the ureteroscope 32 may be directed into the ureter and kidneys to break up kidney stone build up using a laser or ultrasonic lithotripsy device deployed down the working channel of the ureteroscope 32. After lithotripsy is complete, the resulting stone fragments may be removed using baskets deployed down the ureteroscope 32.

Figure 4:
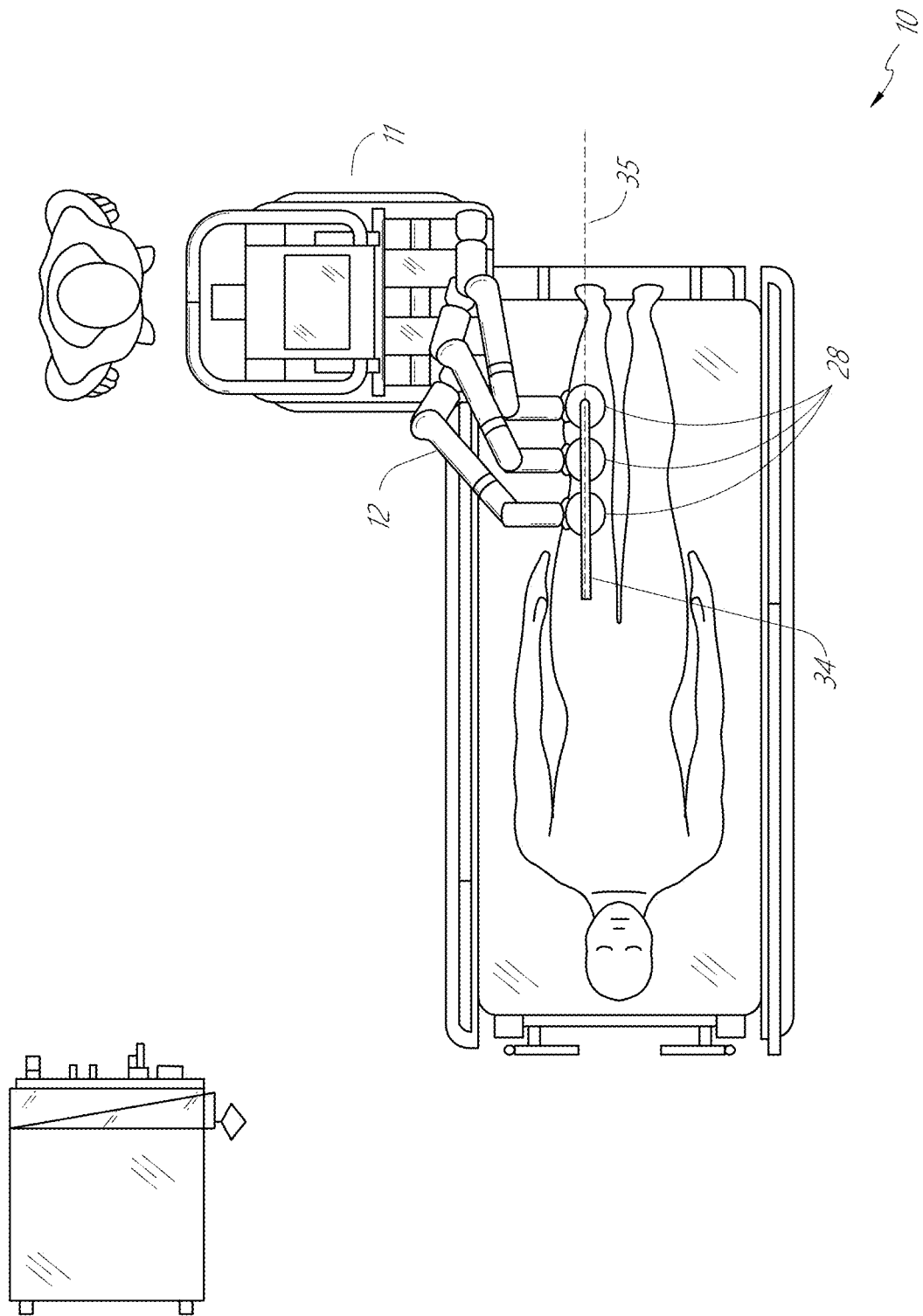
FIG. 4 illustrates an embodiment of the robotic system of FIG. 1 arranged for a vascular procedure.

FIG. 4 illustrates an embodiment of a robotically-enabled system 10 similarly arranged for a vascular procedure. In a vascular procedure, the system 10 may be configured such that the cart 11 may deliver a medical instrument 34, such as a steerable catheter, to an access point in the femoral artery in the patient's leg. The femoral artery presents both a larger diameter for navigation as well as a relatively less circuitous and tortuous path to the patient's heart, which simplifies navigation. As in a ureteroscopic procedure, the cart 11 may be positioned towards the patient's legs and lower abdomen to allow the robotic arms 12 to provide a virtual rail 35 with direct linear access to the femoral artery access point in the patient's thigh/hip region. After insertion into the artery, the medical instrument 34 may be directed and inserted by translating the instrument drivers 28. Alternatively, the cart may be positioned around the patient's upper abdomen in order to reach alternative vascular access points, such as, for example, the carotid and brachial arteries near the shoulder and wrist.

B. Robotic System—Table.

Figure 5:
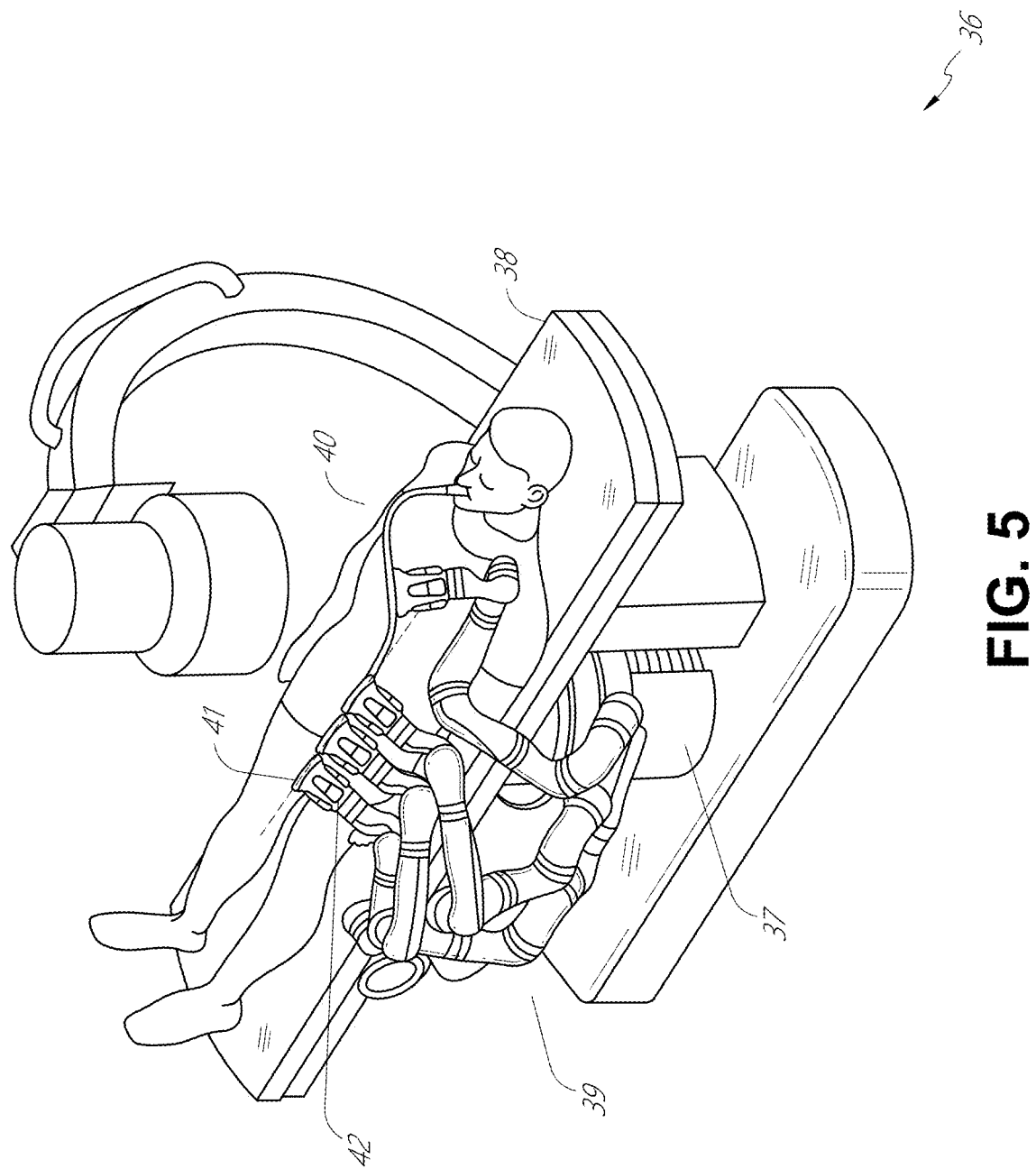
FIG. 5 illustrates an embodiment of a table-based robotic system arranged for a bronchoscopic procedure.

Embodiments of the robotically-enabled medical system may also incorporate the patient's table. Incorporation of the table reduces the amount of capital equipment within the operating room by removing the cart, which allows greater access to the patient. FIG. 5 illustrates an embodiment of such a robotically-enabled system arranged for a bronchoscopic procedure. System 36 includes a support structure or column 37 for supporting platform 38 (shown as a "table" or "bed") over the floor. Much like in the cart-based systems, the end effectors of the robotic arms 39 of the system 36 comprise instrument drivers 42 that are designed to manipulate an elongated medical instrument, such as a bronchoscope 40 in FIG. 5, through or along a virtual rail 41 formed from the linear alignment of the instrument drivers 42. In practice, a C-arm for providing fluoroscopic imaging may be positioned over the patient's upper abdominal area by placing the emitter and detector around the table 38.

Figure 6:
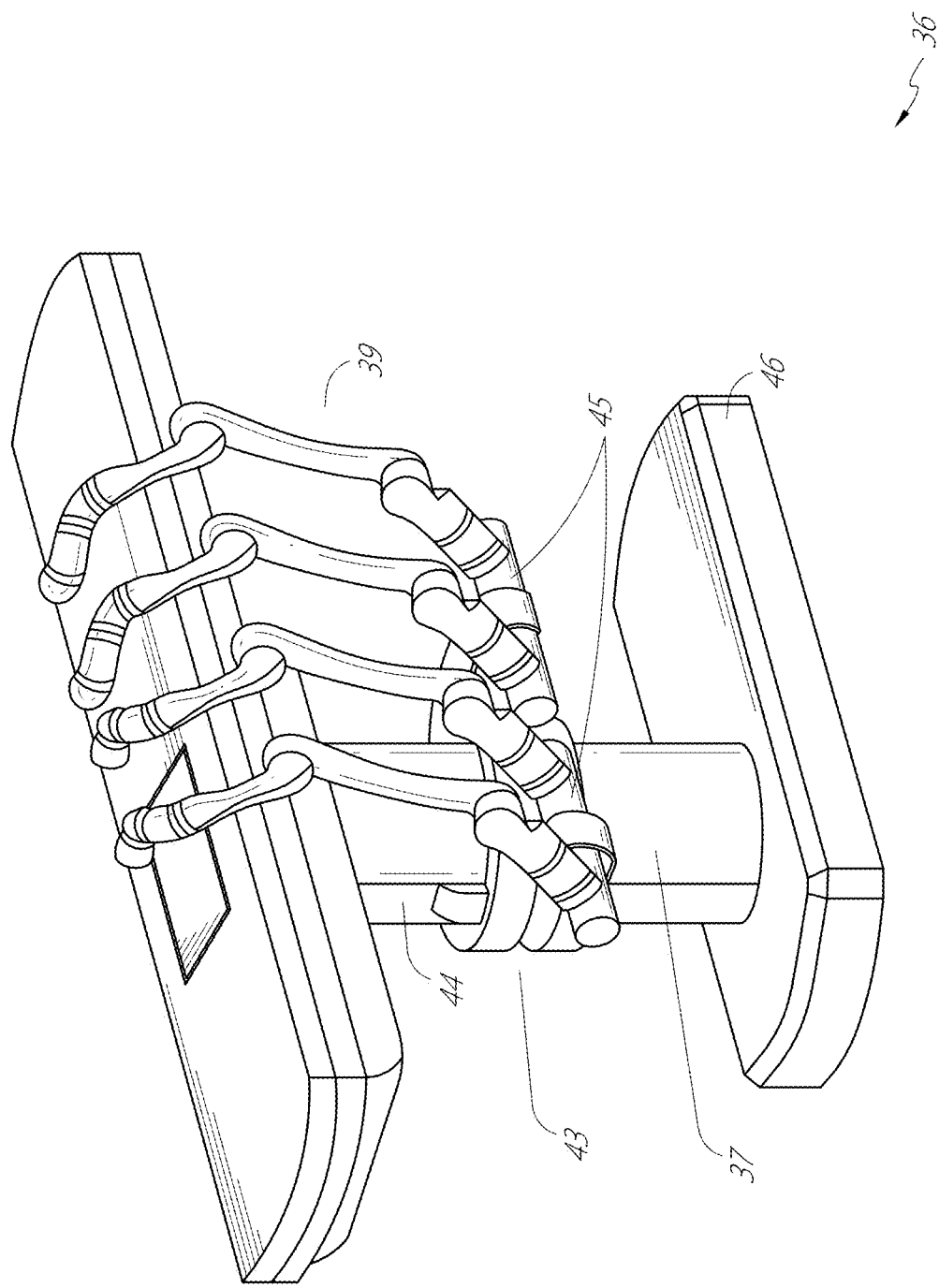
FIG. 6 provides an alternative view of the robotic system of FIG. 5.

FIG. 6 provides an alternative view of the system 36 without the patient and medical instrument for discussion purposes. As shown, the column 37 may include one or more carriages 43 shown as ring-shaped in the system 36, from which the one or more robotic arms 39 may be based. The carriages 43 may translate along a vertical column interface 44 that runs the length of the column 37 to provide different vantage points from which the robotic arms 39 may be positioned to reach the patient. The carriage(s) 43 may rotate around the column 37 using a mechanical motor positioned within the column 37 to allow the robotic arms 39 to have access to multiples sides of the table 38, such as, for example, both sides of the patient. In embodiments with multiple carriages, the carriages may be individually positioned on the column and may translate and/or rotate independently of the other carriages. While the carriages 43 need not surround the column 37 or even be circular, the ring-shape as shown facilitates rotation of the carriages 43 around the column 37 while maintaining structural balance. Rotation and translation of the carriages 43 allows the system 36 to align the medical instruments, such as endoscopes and laparoscopes, into different access points on the patient. In other embodiments (not shown), the system 36 can include a patient table or bed with adjustable arm supports in the form of bars or rails extending alongside it. One or more robotic arms 39 (e.g., via a shoulder with an elbow joint) can be attached to the adjustable arm supports, which can be vertically adjusted. By providing vertical adjustment, the robotic arms 39 are advantageously capable of being stowed compactly beneath the patient table or bed, and subsequently raised during a procedure.

Figure 9:
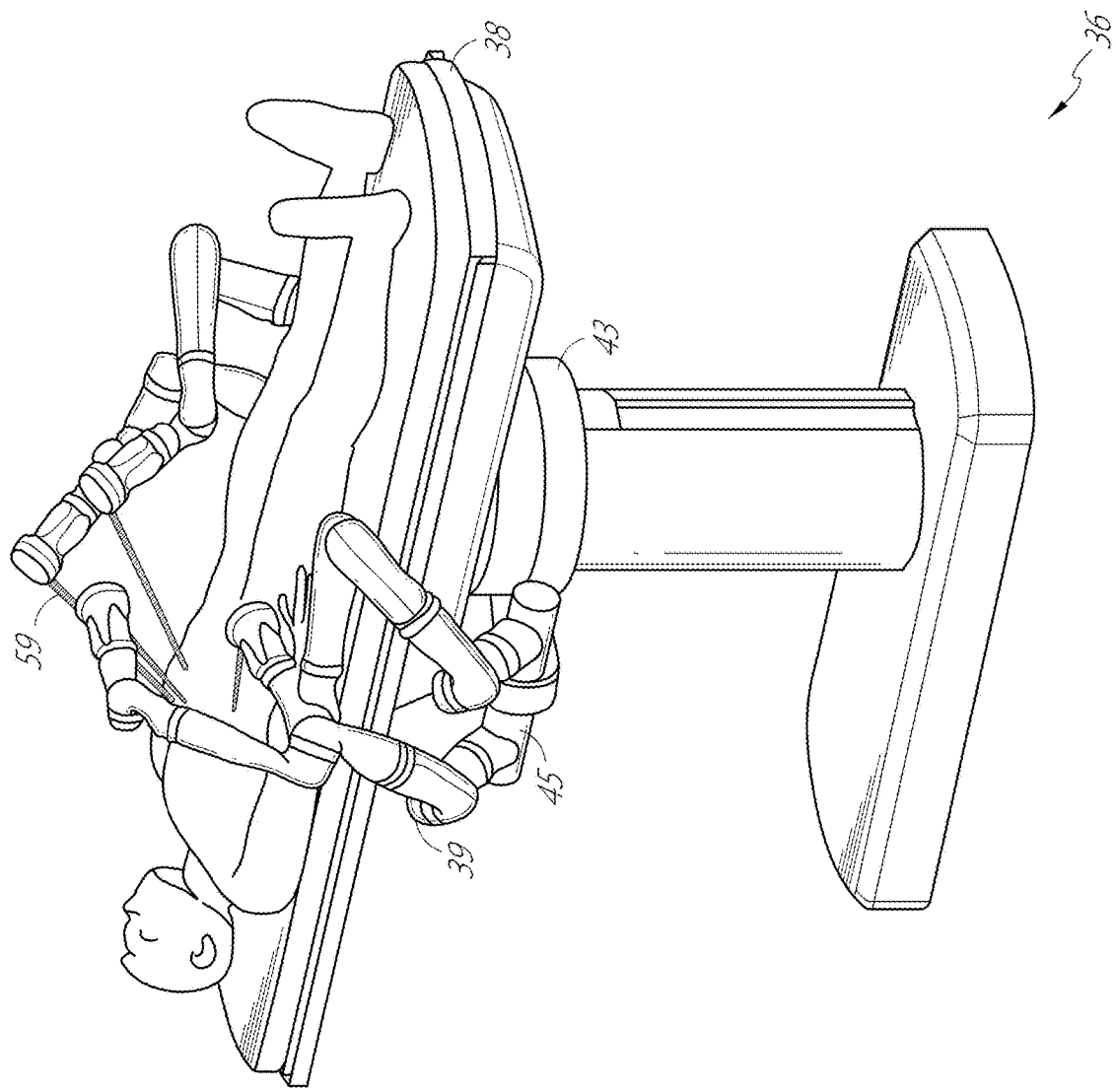
FIG. 9 illustrates an embodiment of a table-based robotic system configured for a laparoscopic procedure.

The robotic arms 39 may be mounted on the carriages 43 through a set of arm mounts 45 comprising a series of joints that may individually rotate and/or telescopically extend to provide additional configurability to the robotic arms 39. Additionally, the arm mounts 45 may be positioned on the carriages 43 such that, when the carriages 43 are appropriately rotated, the arm mounts 45 may be positioned on either the same side of the table 38 (as shown in FIG. 6), on opposite sides of the table 38 (as shown in FIG. 9), or on adjacent sides of the table 38 (not shown).

The column 37 structurally provides support for the table 38, and a path for vertical translation of the carriages 43. Internally, the column 37 may be equipped with lead screws for guiding vertical translation of the carriages, and motors to mechanize the translation of the carriages 43 based the lead screws. The column 37 may also convey power and control signals to the carriages 43 and the robotic arms 39 mounted thereon.

The table base 46 serves a similar function as the cart base 15 in the cart 11 shown in FIG. 2, housing heavier components to balance the table/bed 38, the column 37, the carriages 43, and the robotic arms 39. The table base 46 may also incorporate rigid casters to provide stability during procedures. Deployed from the bottom of the table base 46, the casters may extend in opposite directions on both sides of the base 46 and retract when the system 36 needs to be moved.

With continued reference to FIG. 6, the system 36 may also include a tower (not shown) that divides the functionality of the system 36 between the table and the tower to reduce the form factor and bulk of the table. As in earlier disclosed embodiments, the tower may provide a variety of support functionalities to the table, such as processing, computing, and control capabilities, power, fluidics, and/or optical and sensor processing. The tower may also be movable to be positioned away from the patient to improve physician access and de-clutter the operating room. Additionally, placing components in the tower allows for more storage space in the table base 46 for potential stowage of the robotic arms 39. The tower may also include a master controller or console that provides both a user interface for user input, such as keyboard and/or pendant, as well as a display screen (or touchscreen) for preoperative and intraoperative information, such as real-time imaging, navigation, and tracking information. In some embodiments, the tower may also contain holders for gas tanks to be used for insufflation.

Figure 7:
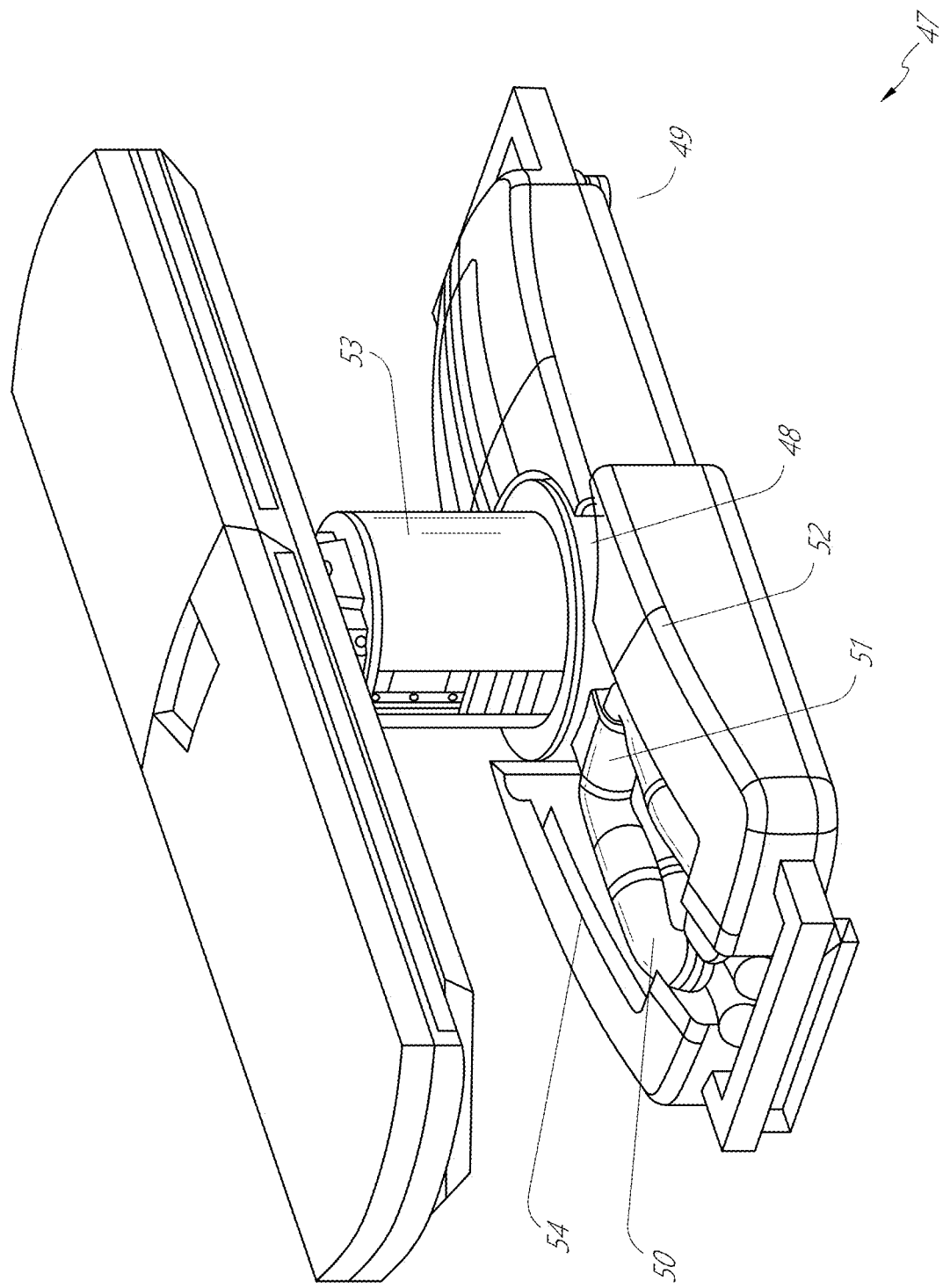
FIG. 7 illustrates an example system configured to stow robotic arm(s).

In some embodiments, a table base may stow and store the robotic arms when not in use. FIG. 7 illustrates a system 47 that stows robotic arms in an embodiment of the table-based system. In the system 47, carriages 48 may be vertically translated into base 49 to stow robotic arms 50, arm mounts 51, and the carriages 48 within the base 49. Base covers 52 may be translated and retracted open to deploy the carriages 48, arm mounts 51, and robotic arms 50 around column 53, and closed to stow to protect them when not in use. The base covers 52 may be sealed with a membrane 54 along the edges of its opening to prevent dirt and fluid ingress when closed.

Figure 8:
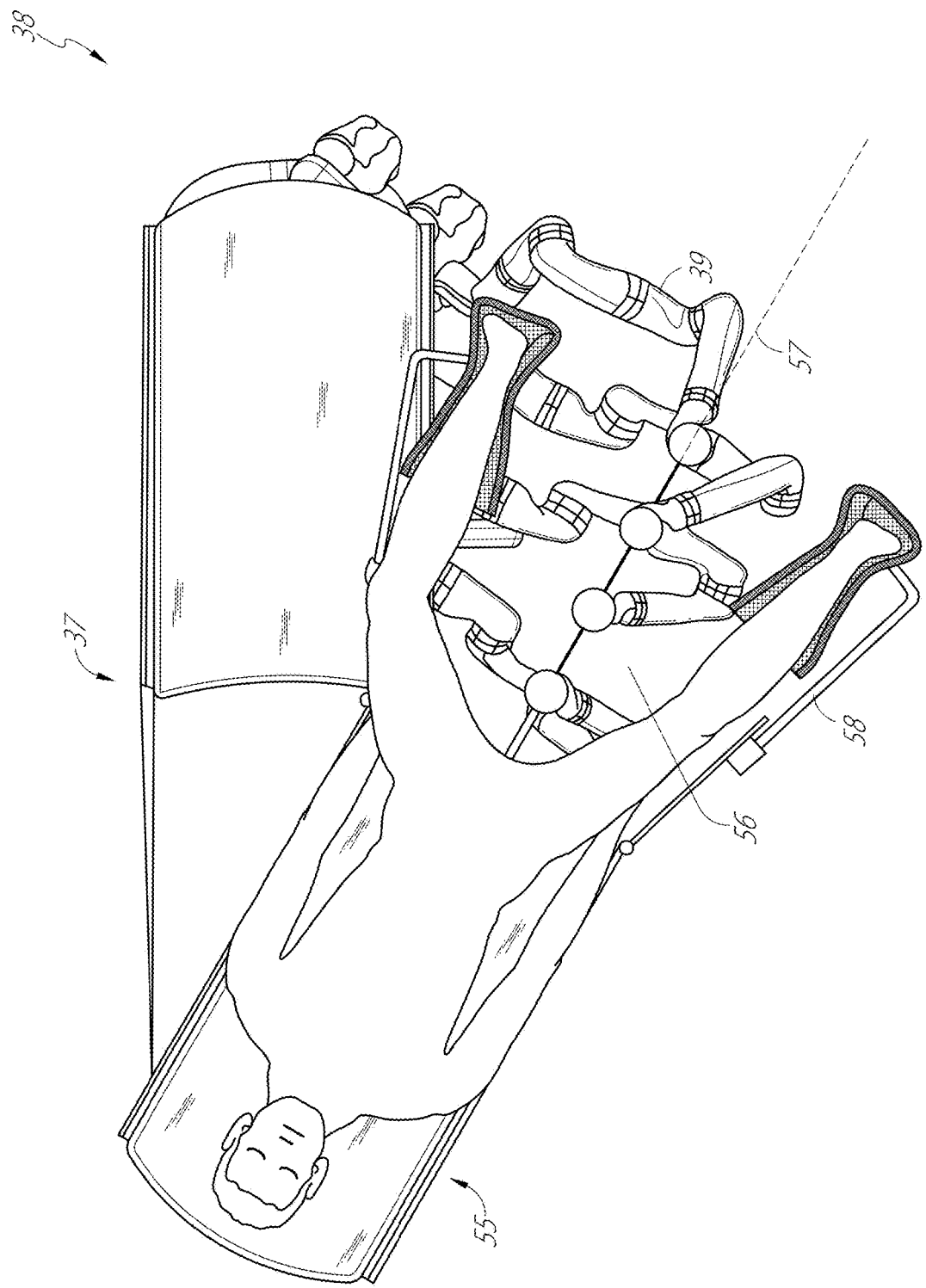
FIG. 8 illustrates an embodiment of a table-based robotic system configured for a ureteroscopic procedure.

FIG. 8 illustrates an embodiment of a robotically-enabled table-based system configured for a ureteroscopic procedure. In a ureteroscopy, the table 38 may include a swivel portion 55 for positioning a patient off-angle from the column 37 and table base 46. The swivel portion 55 may rotate or pivot around a pivot point (e.g., located below the patient's head) in order to position the bottom portion of the swivel portion 55 away from the column 37. For example, the pivoting of the swivel portion 55 allows a C-arm (not shown) to be positioned over the patient's lower abdomen without competing for space with the column (not shown) below table 38. By rotating the carriage 35 (not shown) around the column 37, the robotic arms 39 may directly insert a ureteroscope 56 along a virtual rail 57 into the patient's groin area to reach the urethra. In a ureteroscopy, stirrups 58 may also be fixed to the swivel portion 55 of the table 38 to support the position of the patient's legs during the procedure and allow clear access to the patient's groin area.

In a laparoscopic procedure, through small incision(s) in the patient's abdominal wall, minimally invasive instruments may be inserted into the patient's anatomy. In some embodiments, the minimally invasive instruments comprise an elongated rigid member, such as a shaft, which is used to access anatomy within the patient. After inflation of the patient's abdominal cavity, the instruments may be directed to perform surgical or medical tasks, such as grasping, cutting, ablating, suturing, etc. In some embodiments, the instruments can comprise a scope, such as a laparoscope. FIG. 9 illustrates an embodiment of a robotically-enabled table-based system configured for a laparoscopic procedure. As shown in FIG. 9, the carriages 43 of the system 36 may be rotated and vertically adjusted to position pairs of the robotic arms 39 on opposite sides of the table 38, such that instrument 59 may be positioned using the arm mounts 45 to be passed through minimal incisions on both sides of the patient to reach his/her abdominal cavity.

Figure 10:
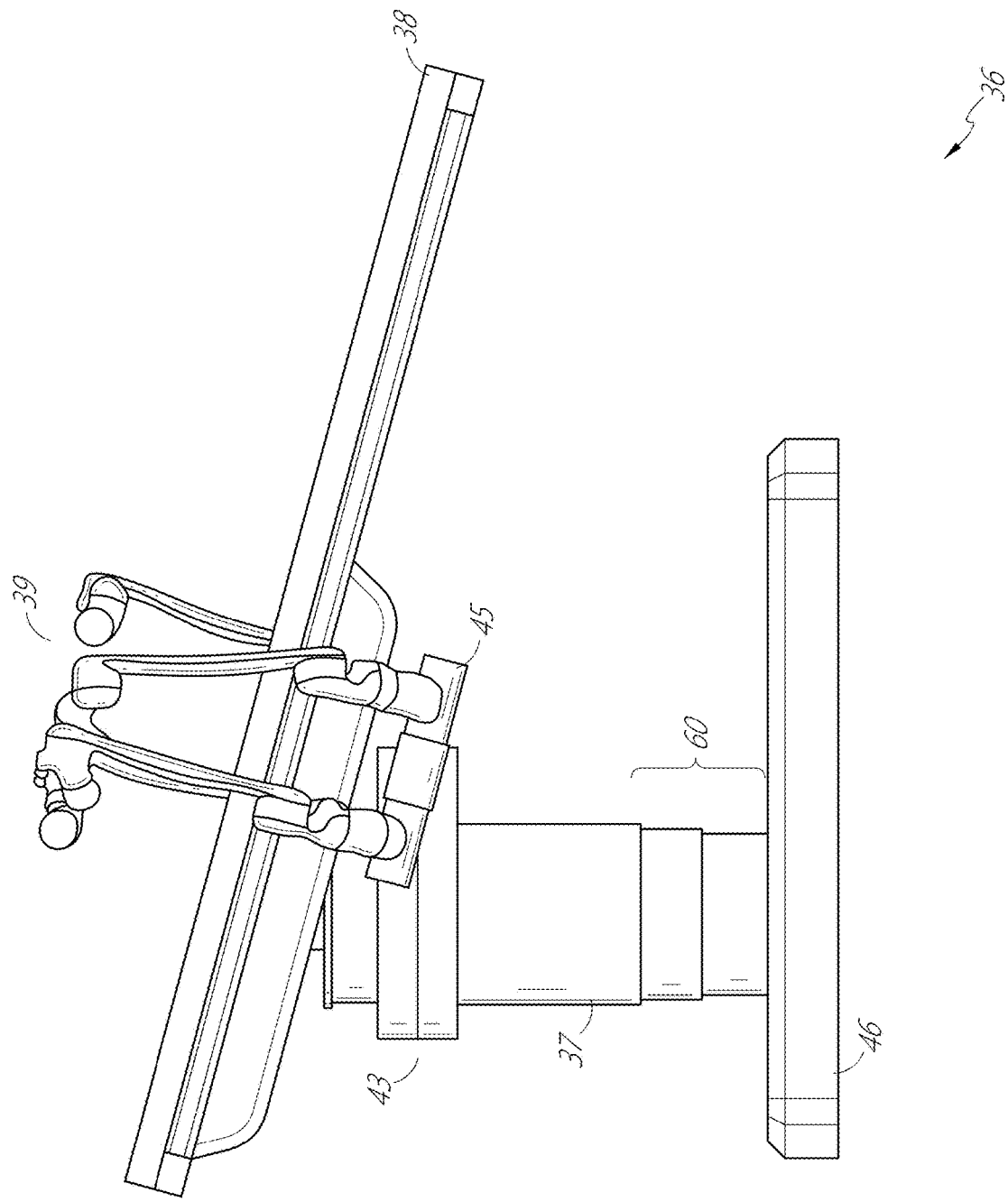
FIG. 10 illustrates an embodiment of the table-based robotic system of FIGS. 5-9 with pitch or tilt adjustment.

To accommodate laparoscopic procedures, the robotically-enabled table system may also tilt the platform to a desired angle. FIG. 10 illustrates an embodiment of the robotically-enabled medical system with pitch or tilt adjustment. As shown in FIG. 10, the system 36 may accommodate tilt of the table 38 to position one portion of the table at a greater distance from the floor than the other. Additionally, the arm mounts 45 may rotate to match the tilt such that the robotic arms 39 maintain the same planar relationship with the table 38. To accommodate steeper angles, the column 37 may also include telescoping portions 60 that allow vertical extension of the column 37 to keep the table 38 from touching the floor or colliding with the table base 46.

Figure 11:
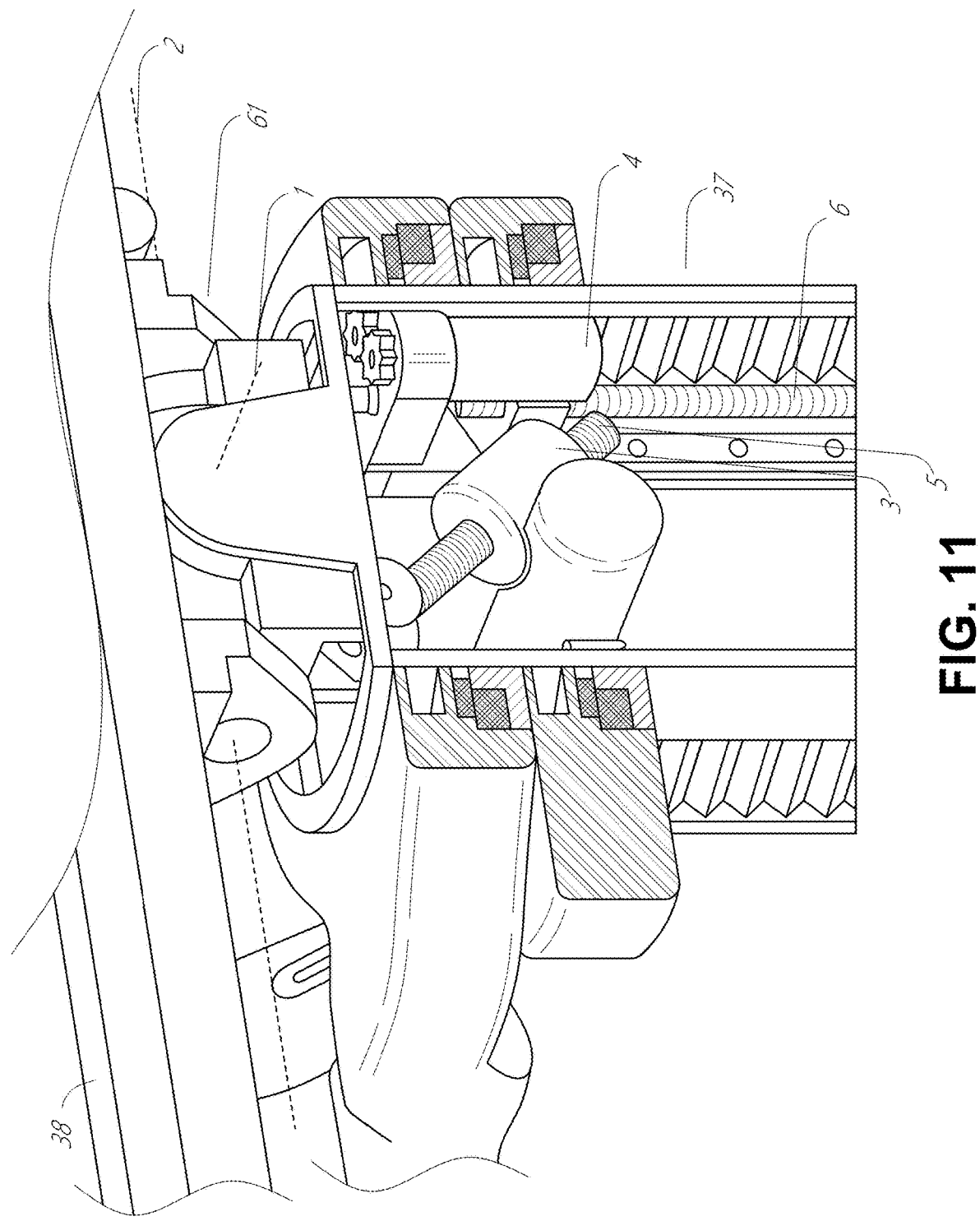
FIG. 11 provides a detailed illustration of the interface between the table and the column of the table-based robotic system of FIGS. 5-10.

FIG. 11 provides a detailed illustration of the interface between the table 38 and the column 37. Pitch rotation mechanism 61 may be configured to alter the pitch angle of the table 38 relative to the column 37 in multiple degrees of freedom. The pitch rotation mechanism 61 may be enabled by the positioning of orthogonal axes 1, 2 at the column-table interface, each axis actuated by a separate motor 3, 4 responsive to an electrical pitch angle command. Rotation along one screw 5 would enable tilt adjustments in one axis 1, while rotation along the other screw 6 would enable tilt adjustments along the other axis 2. In some embodiments, a ball joint can be used to alter the pitch angle of the table 38 relative to the column 37 in multiple degrees of freedom.

For example, pitch adjustments are particularly useful when trying to position the table in a Trendelenburg position, i.e., position the patient's lower abdomen at a higher position from the floor than the patient's upper abdomen, for lower abdominal surgery. The Trendelenburg position causes the patient's internal organs to slide towards his/her upper abdomen through the force of gravity, clearing out the abdominal cavity for minimally invasive tools to enter and perform lower abdominal surgical or medical procedures, such as laparoscopic prostatectomy.

Figure 12:
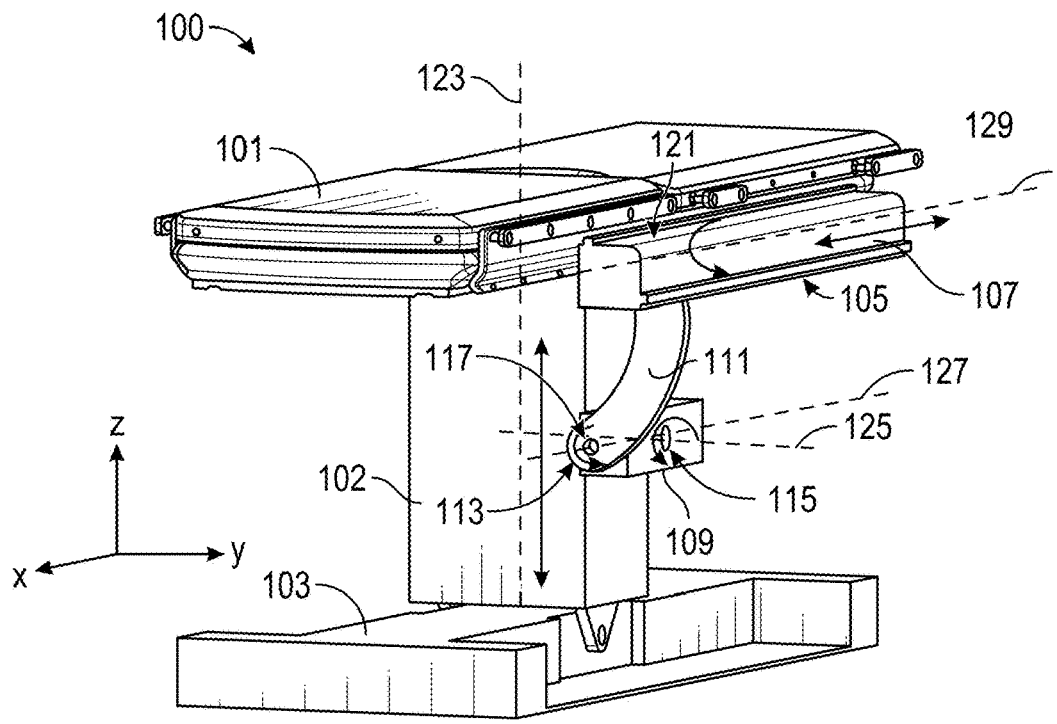
FIG. 12 illustrates an alternative embodiment of a table-based robotic system.
Figure 13:
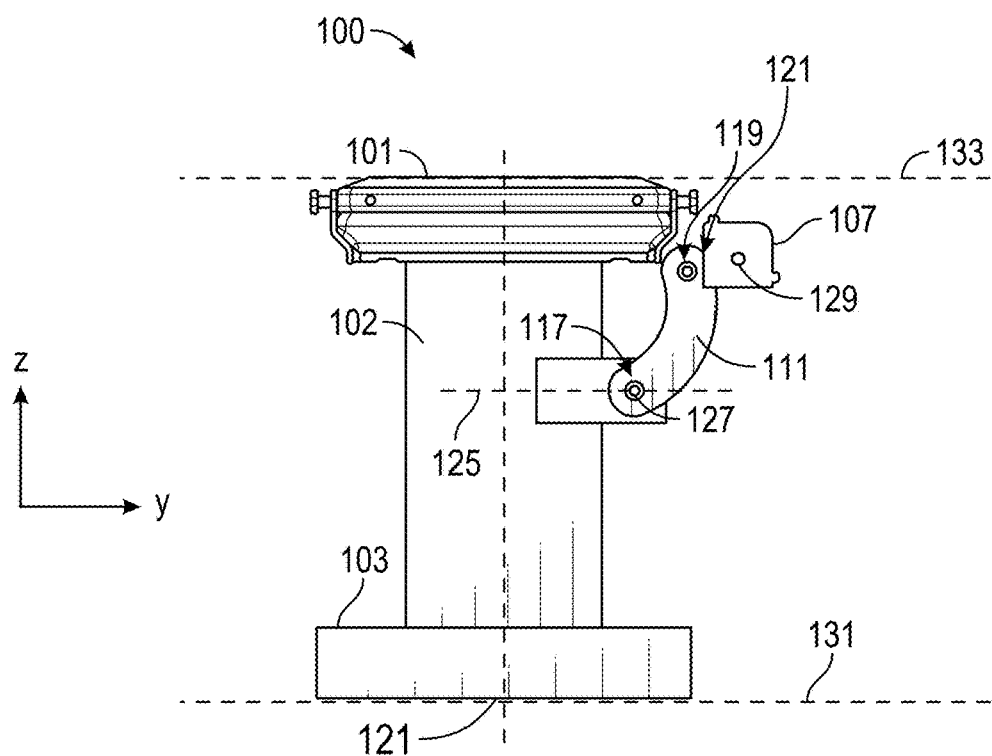
FIG. 13 illustrates an end view of the table-based robotic system of FIG. 12.

FIGS. 12 and 13 illustrate isometric and end views of an alternative embodiment of a table-based surgical robotics system 100. The surgical robotics system 100 includes one or more adjustable arm supports 105 that can be configured to support one or more robotic arms (see, for example, FIG. 14) relative to a table 101. In the illustrated embodiment, a single adjustable arm support 105 is shown, though an additional arm support can be provided on an opposite side of the table 101. The adjustable arm support 105 can be configured so that it can move relative to the table 101 to adjust and/or vary the position of the adjustable arm support 105 and/or any robotic arms mounted thereto relative to the table 101. For example, the adjustable arm support 105 may be adjusted one or more degrees of freedom relative to the table 101. The adjustable arm support 105 provides high versatility to the system 100, including the ability to easily stow the one or more adjustable arm supports 105 and any robotics arms attached thereto beneath the table 101. The adjustable arm support 105 can be elevated from the stowed position to a position below an upper surface of the table 101. In other embodiments, the adjustable arm support 105 can be elevated from the stowed position to a position above an upper surface of the table 101.

The adjustable arm support 105 can provide several degrees of freedom, including lift, lateral translation, tilt, etc. In the illustrated embodiment of FIGS. 12 and 13, the arm support 105 is configured with four degrees of freedom, which are illustrated with arrows in FIG. 12. A first degree of freedom allows for adjustment of the adjustable arm support 105 in the z-direction ("Z-lift"). For example, the adjustable arm support 105 can include a carriage 109 configured to move up or down along or relative to a column 102 supporting the table 101. A second degree of freedom can allow the adjustable arm support 105 to tilt. For example, the adjustable arm support 105 can include a rotary joint, which can allow the adjustable arm support 105 to be aligned with the bed in a Trendelenburg position. A third degree of freedom can allow the adjustable arm support 105 to "pivot up," which can be used to adjust a distance between a side of the table 101 and the adjustable arm support 105. A fourth degree of freedom can permit translation of the adjustable arm support 105 along a longitudinal length of the table.

The surgical robotics system 100 in FIGS. 12 and 13 can comprise a table supported by a column 102 that is mounted to a base 103. The base 103 and the column 102 support the table 101 relative to a support surface. A floor axis 131 and a support axis 133 are shown in FIG. 13.

The adjustable arm support 105 can be mounted to the column 102. In other embodiments, the arm support 105 can be mounted to the table 101 or base 103. The adjustable arm support 105 can include a carriage 109, a bar or rail connector 111 and a bar or rail 107. In some embodiments, one or more robotic arms mounted to the rail 107 can translate and move relative to one another.

The carriage 109 can be attached to the column 102 by a first joint 113, which allows the carriage 109 to move relative to the column 102 (e.g., such as up and down a first or vertical axis 123). The first joint 113 can provide the first degree of freedom ("Z-lift") to the adjustable arm support 105. The adjustable arm support 105 can include a second joint 115, which provides the second degree of freedom (tilt) for the adjustable arm support 105. The adjustable arm support 105 can include a third joint 117, which can provide the third degree of freedom ("pivot up") for the adjustable arm support 105. An additional joint 119 (shown in FIG. 13) can be provided that mechanically constrains the third joint 117 to maintain an orientation of the rail 107 as the rail connector 111 is rotated about a third axis 127. The adjustable arm support 105 can include a fourth joint 121, which can provide a fourth degree of freedom (translation) for the adjustable arm support 105 along a fourth axis 129.

Figure 14:
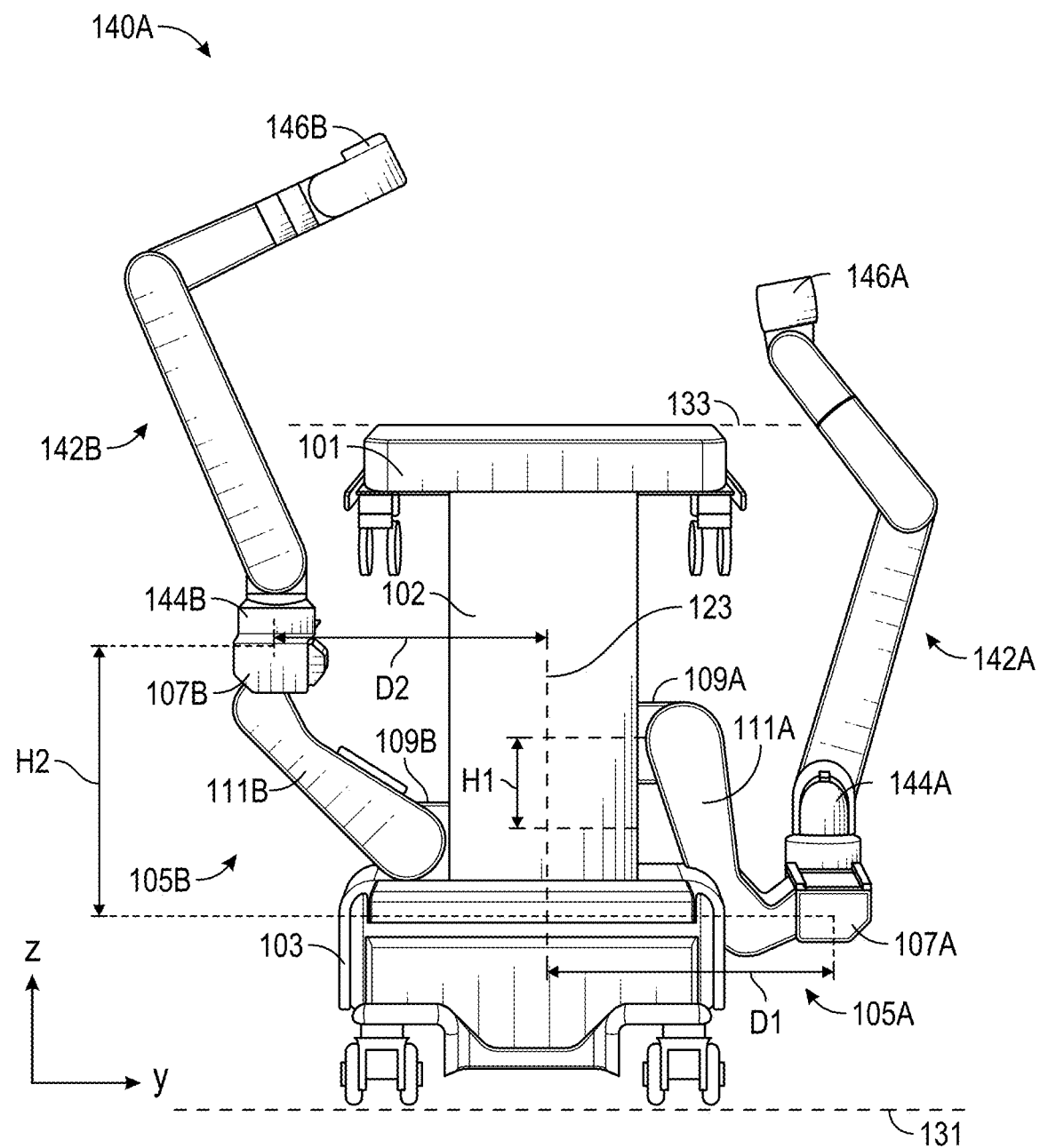
FIG. 14 illustrates an end view of a table-based robotic system with robotic arms attached thereto.

FIG. 14 illustrates an end view of the surgical robotics system 140A with two adjustable arm supports 105A, 105B mounted on opposite sides of a table 101. A first robotic arm 142A is attached to the bar or rail 107A of the first adjustable arm support 105B. The first robotic arm 142A includes a base 144A attached to the rail 107A. The distal end of the first robotic arm 142A includes an instrument drive mechanism 146A that can attach to one or more robotic medical instruments or tools. Similarly, the second robotic arm 142B includes a base 144B attached to the rail 107B. The distal end of the second robotic arm 142B includes an instrument drive mechanism 146B. The instrument drive mechanism 146B can be configured to attach to one or more robotic medical instruments or tools.

In some embodiments, one or more of the robotic arms 142A, 142B comprises an arm with seven or more degrees of freedom. In some embodiments, one or more of the robotic arms 142A, 142B can include eight degrees of freedom, including an insertion axis (1-degree of freedom including insertion), a wrist (3-degrees of freedom including wrist pitch, yaw and roll), an elbow (1-degree of freedom including elbow pitch), a shoulder (2-degrees of freedom including shoulder pitch and yaw), and base 144A, 144B (1-degree of freedom including translation). In some embodiments, the insertion degree of freedom can be provided by the robotic arm 142A, 142B, while in other embodiments, the instrument itself provides insertion via an instrument-based insertion architecture.

C. Instrument Driver & Interface.

The end effectors of the system's robotic arms may comprise (i) an instrument driver (alternatively referred to as "instrument drive mechanism" or "instrument device manipulator") that incorporates electro-mechanical means for actuating the medical instrument and (ii) a removable or detachable medical instrument, which may be devoid of any electro-mechanical components, such as motors. This dichotomy may be driven by the need to sterilize medical instruments used in medical procedures, and the inability to adequately sterilize expensive capital equipment due to their intricate mechanical assemblies and sensitive electronics. Accordingly, the medical instruments may be designed to be detached, removed, and interchanged from the instrument driver (and thus the system) for individual sterilization or disposal by the physician or the physician's staff. In contrast, the instrument drivers need not be changed or sterilized, and may be draped for protection.

Figure 15:
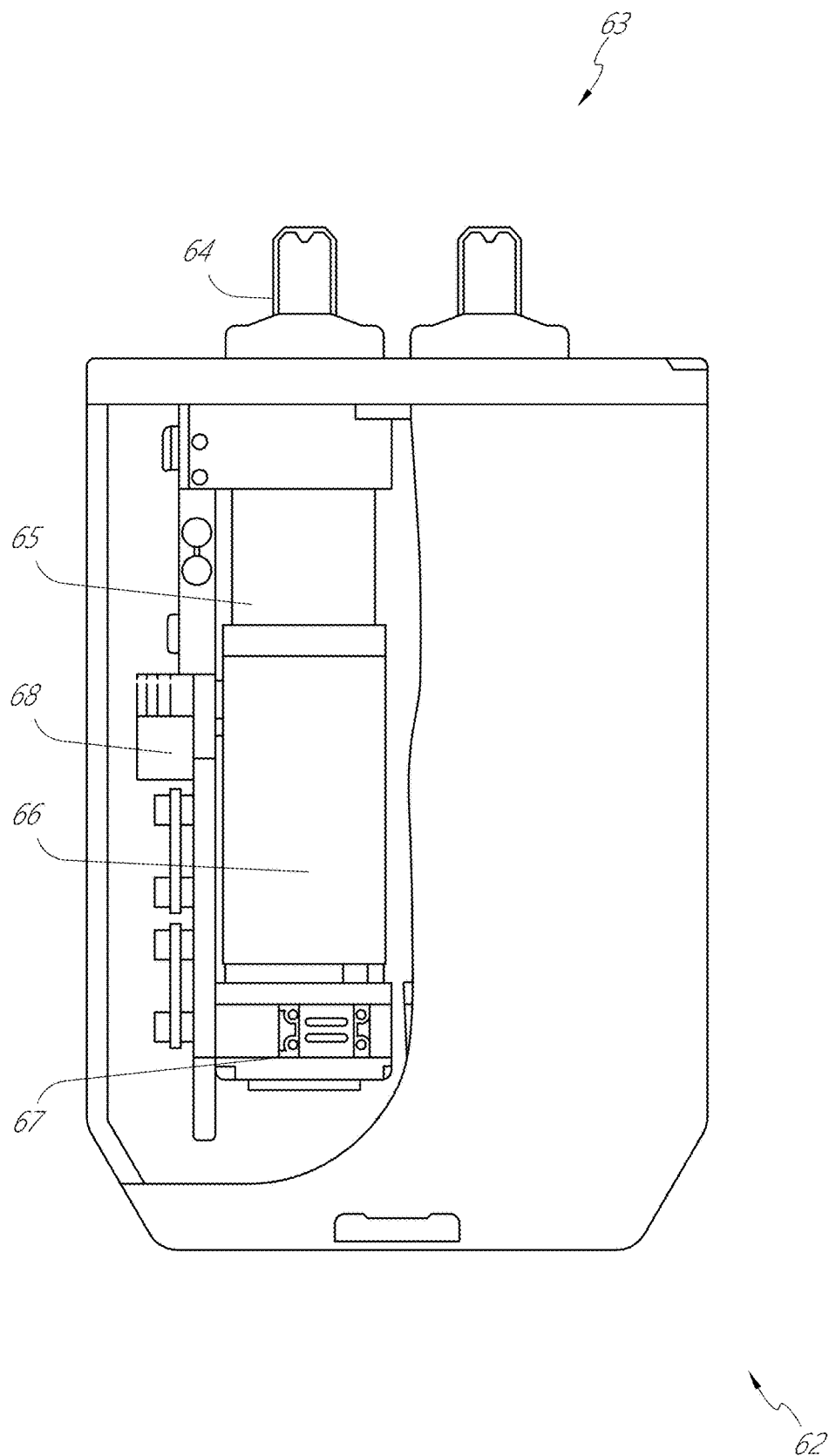
FIG. 15 illustrates an exemplary instrument driver.

FIG. 15 illustrates an example instrument driver. Positioned at the distal end of a robotic arm, instrument driver 62 comprises one or more drive units 63 arranged with parallel axes to provide controlled torque to a medical instrument via drive shafts 64. Each drive unit 63 comprises an individual drive shaft 64 for interacting with the instrument, a gear head 65 for converting the motor shaft rotation to a desired torque, a motor 66 for generating the drive torque, an encoder 67 to measure the speed of the motor shaft and provide feedback to the control circuitry, and control circuitry 68 for receiving control signals and actuating the drive unit. Each drive unit 63 being independently controlled and motorized, the instrument driver 62 may provide multiple (e.g., four as shown in FIG. 15) independent drive outputs to the medical instrument. In operation, the control circuitry 68 would receive a control signal, transmit a motor signal to the motor 66, compare the resulting motor speed as measured by the encoder 67 with the desired speed, and modulate the motor signal to generate the desired torque.

For procedures that require a sterile environment, the robotic system may incorporate a drive interface, such as a sterile adapter connected to a sterile drape, that sits between the instrument driver and the medical instrument. The chief purpose of the sterile adapter is to transfer angular motion from the drive shafts of the instrument driver to the drive inputs of the instrument while maintaining physical separation, and thus sterility, between the drive shafts and drive inputs. Accordingly, an example sterile adapter may comprise a series of rotational inputs and outputs intended to be mated with the drive shafts of the instrument driver and drive inputs on the instrument. Connected to the sterile adapter, the sterile drape, comprised of a thin, flexible material such as transparent or translucent plastic, is designed to cover the capital equipment, such as the instrument driver, robotic arm, and cart (in a cart-based system) or table (in a table-based system). Use of the drape would allow the capital equipment to be positioned proximate to the patient while still being located in an area not requiring sterilization (i.e., non-sterile field). On the other side of the sterile drape, the medical instrument may interface with the patient in an area requiring sterilization (i.e., sterile field).

D. Medical Instrument.

Figure 16:
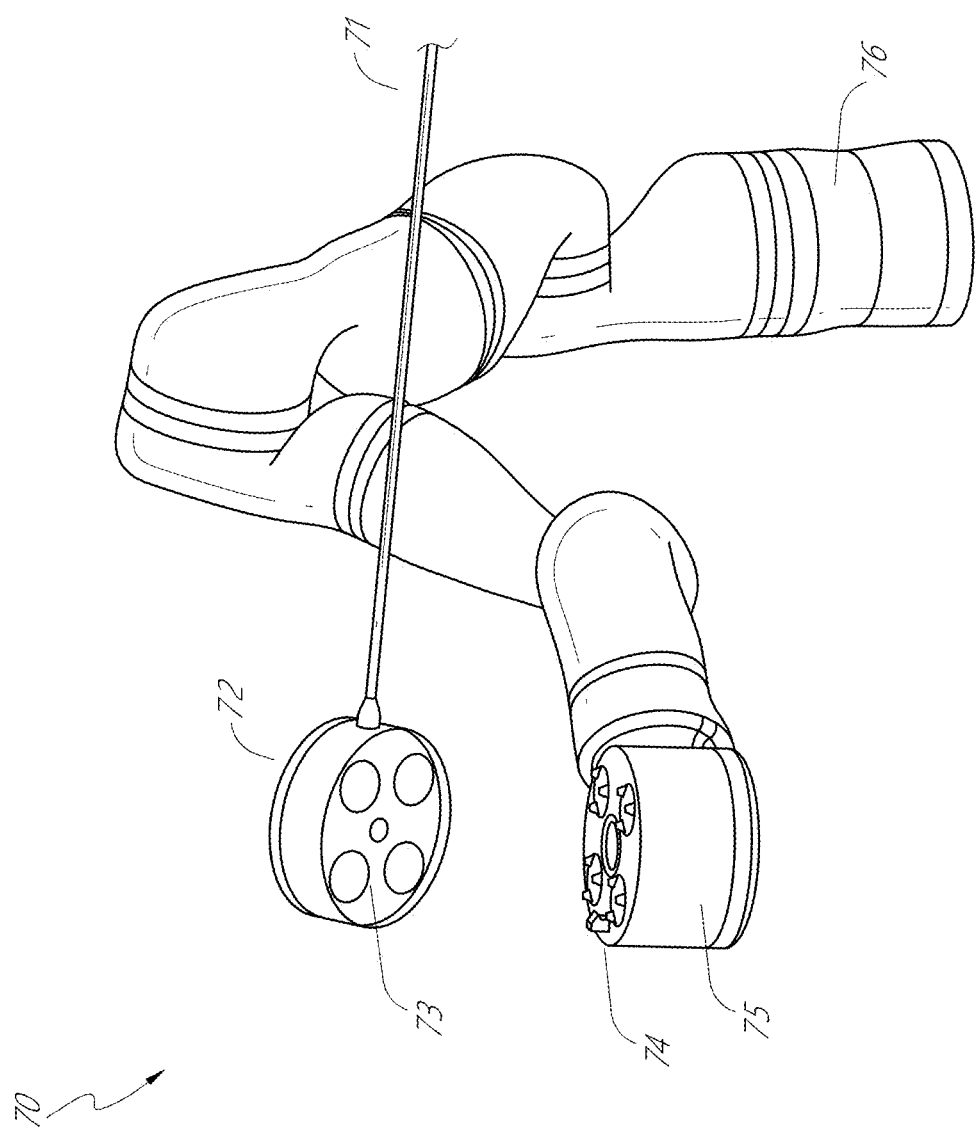
FIG. 16 illustrates an exemplary medical instrument with a paired instrument driver.

FIG. 16 illustrates an example medical instrument with a paired instrument driver. Like other instruments designed for use with a robotic system, medical instrument 70 comprises an elongated shaft 71 (or elongate body) and an instrument base 72. The instrument base 72, also referred to as an "instrument handle" due to its intended design for manual interaction by the physician, may generally comprise rotatable drive inputs 73, e.g., receptacles, pulleys or spools, that are designed to be mated with drive outputs 74 that extend through a drive interface on instrument driver 75 at the distal end of robotic arm 76. When physically connected, latched, and/or coupled, the mated drive inputs 73 of the instrument base 72 may share axes of rotation with the drive outputs 74 in the instrument driver 75 to allow the transfer of torque from the drive outputs 74 to the drive inputs 73. In some embodiments, the drive outputs 74 may comprise splines that are designed to mate with receptacles on the drive inputs 73.

The elongated shaft 71 is designed to be delivered through either an anatomical opening or lumen, e.g., as in endoscopy, or a minimally invasive incision, e.g., as in laparoscopy. The elongated shaft 71 may be either flexible (e.g., having properties similar to an endoscope) or rigid (e.g., having properties similar to a laparoscope) or contain a customized combination of both flexible and rigid portions. When designed for laparoscopy, the distal end of a rigid elongated shaft may be connected to an end effector extending from a jointed wrist formed from a clevis with at least one degree of freedom and a surgical tool or medical instrument, such as, for example, a grasper or scissors, that may be actuated based on force from the tendons as the drive inputs rotate in response to torque received from the drive outputs 74 of the instrument driver 75. When designed for endoscopy, the distal end of a flexible elongated shaft may include a steerable or controllable bending section that may be articulated and bent based on torque received from the drive outputs 74 of the instrument driver 75.

Torque from the instrument driver 75 is transmitted down the elongated shaft 71 using tendons along the elongated shaft 71. These individual tendons, such as pull wires, may be individually anchored to individual drive inputs 73 within the instrument handle 72. From the handle 72, the tendons are directed down one or more pull lumens along the elongated shaft 71 and anchored at the distal portion of the elongated shaft 71, or in the wrist at the distal portion of the elongated shaft. During a surgical procedure, such as a laparoscopic, endoscopic or hybrid procedure, these tendons may be coupled to a distally mounted end effector, such as a wrist, grasper, or scissor. Under such an arrangement, torque exerted on drive inputs 73 would transfer tension to the tendon, thereby causing the end effector to actuate in some way. In some embodiments, during a surgical procedure, the tendon may cause a joint to rotate about an axis, thereby causing the end effector to move in one direction or another. Alternatively, the tendon may be connected to one or more jaws of a grasper at the distal end of the elongated shaft 71, where tension from the tendon causes the grasper to close.

In endoscopy, the tendons may be coupled to a bending or articulating section positioned along the elongated shaft 71 (e.g., at the distal end) via adhesive, control ring, or other mechanical fixation. When fixedly attached to the distal end of a bending section, torque exerted on the drive inputs 73 would be transmitted down the tendons, causing the softer, bending section (sometimes referred to as the articulable section or region) to bend or articulate. Along the non-bending sections, it may be advantageous to spiral or helix the individual pull lumens that direct the individual tendons along (or inside) the walls of the endoscope shaft to balance the radial forces that result from tension in the pull wires. The angle of the spiraling and/or spacing therebetween may be altered or engineered for specific purposes, wherein tighter spiraling exhibits lesser shaft compression under load forces, while lower amounts of spiraling results in greater shaft compression under load forces, but limits bending. On the other end of the spectrum, the pull lumens may be directed parallel to the longitudinal axis of the elongated shaft 71 to allow for controlled articulation in the desired bending or articulable sections.

In endoscopy, the elongated shaft 71 houses a number of components to assist with the robotic procedure. The shaft 71 may comprise a working channel for deploying surgical tools (or medical instruments), irrigation, and/or aspiration to the operative region at the distal end of the shaft 71. The shaft 71 may also accommodate wires and/or optical fibers to transfer signals to/from an optical assembly at the distal tip, which may include an optical camera. The shaft 71 may also accommodate optical fibers to carry light from proximally-located light sources, such as light emitting diodes, to the distal end of the shaft 71.

At the distal end of the instrument 70, the distal tip may also comprise the opening of a working channel for delivering tools for diagnostic and/or therapy, irrigation, and aspiration to an operative site. The distal tip may also include a port for a camera, such as a fiberscope or a digital camera, to capture images of an internal anatomical space. Relatedly, the distal tip may also include ports for light sources for illuminating the anatomical space when using the camera.

In the example of FIG. 16, the drive shaft axes, and thus the drive input axes, are orthogonal to the axis of the elongated shaft 71. This arrangement, however, complicates roll capabilities for the elongated shaft 71. Rolling the elongated shaft 71 along its axis while keeping the drive inputs 73 static results in undesirable tangling of the tendons as they extend off the drive inputs 73 and enter pull lumens within the elongated shaft 71. The resulting entanglement of such tendons may disrupt any control algorithms intended to predict movement of the flexible elongated shaft 71 during an endoscopic procedure.

Figure 17:
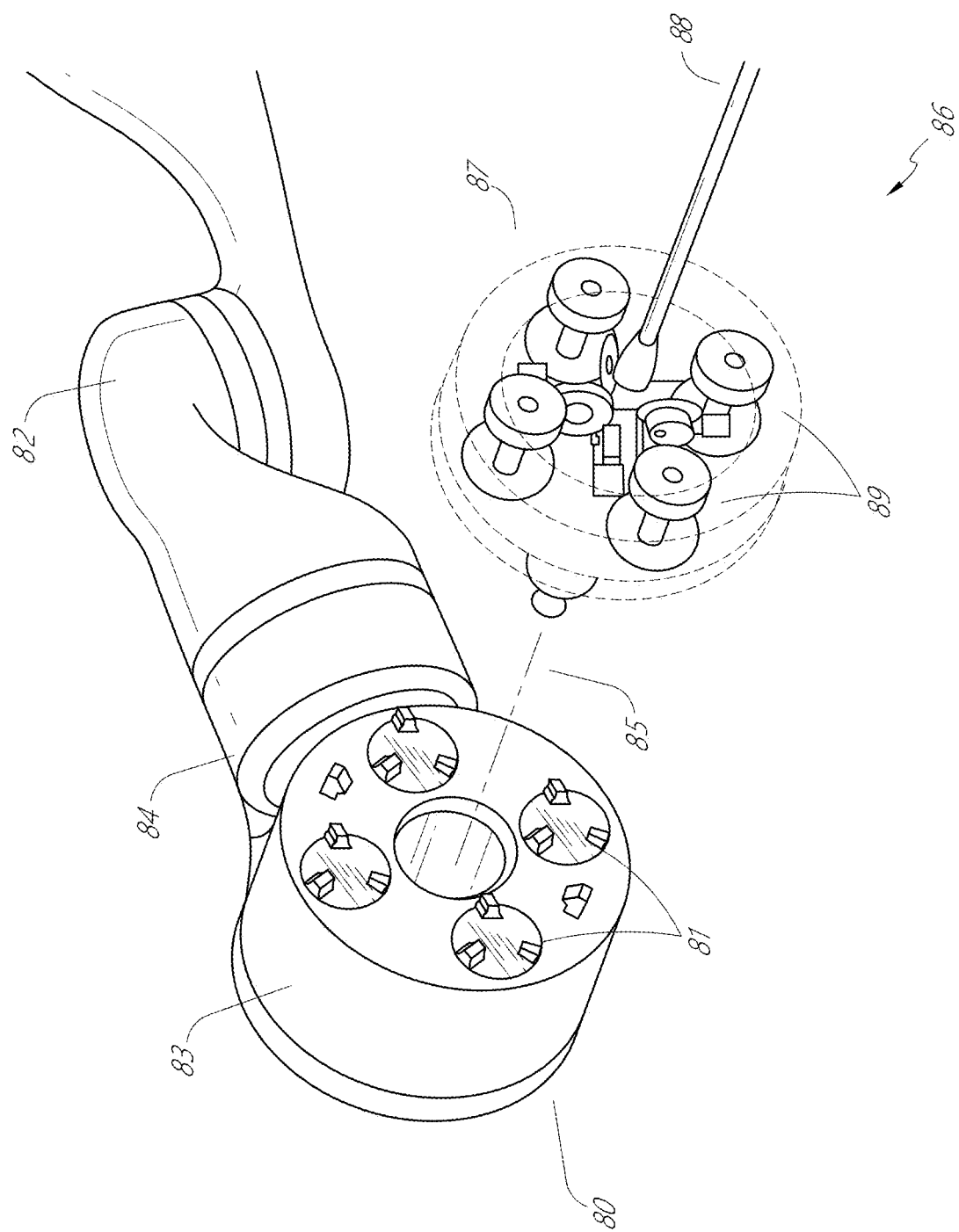
FIG. 17 illustrates an alternative design for an instrument driver and instrument where the axes of the drive units are parallel to the axis of the elongated shaft of the instrument.

FIG. 17 illustrates an alternative design for an instrument driver and instrument where the axes of the drive units are parallel to the axis of the elongated shaft of the instrument. As shown, a circular instrument driver 80 comprises four drive units with their drive outputs 81 aligned in parallel at the end of a robotic arm 82. The drive units, and their respective drive outputs 81, are housed in a rotational assembly 83 of the instrument driver 80 that is driven by one of the drive units within the assembly 83. In response to torque provided by the rotational drive unit, the rotational assembly 83 rotates along a circular bearing that connects the rotational assembly 83 to the non-rotational portion 84 of the instrument driver 80. Power and controls signals may be communicated from the non-rotational portion 84 of the instrument driver 80 to the rotational assembly 83 through electrical contacts that may be maintained through rotation by a brushed slip ring connection (not shown). In other embodiments, the rotational assembly 83 may be responsive to a separate drive unit that is integrated into the non-rotatable portion 84, and thus not in parallel to the other drive units. The rotational mechanism 83 allows the instrument driver 80 to rotate the drive units, and their respective drive outputs 81, as a single unit around an instrument driver axis 85.

Like earlier disclosed embodiments, an instrument 86 may comprise an elongated shaft portion 88 and an instrument base 87 (shown with a transparent external skin for discussion purposes) comprising a plurality of drive inputs 89 (such as receptacles, pulleys, and spools) that are configured to receive the drive outputs 81 in the instrument driver 80. Unlike prior disclosed embodiments, the instrument shaft 88 extends from the center of the instrument base 87 with an axis substantially parallel to the axes of the drive inputs 89, rather than orthogonal as in the design of FIG. 16.

When coupled to the rotational assembly 83 of the instrument driver 80, the medical instrument 86, comprising instrument base 87 and instrument shaft 88, rotates in combination with the rotational assembly 83 about the instrument driver axis 85. Since the instrument shaft 88 is positioned at the center of instrument base 87, the instrument shaft 88 is coaxial with instrument driver axis 85 when attached. Thus, rotation of the rotational assembly 83 causes the instrument shaft 88 to rotate about its own longitudinal axis. Moreover, as the instrument base 87 rotates with the instrument shaft 88, any tendons connected to the drive inputs 89 in the instrument base 87 are not tangled during rotation. Accordingly, the parallelism of the axes of the drive outputs 81, drive inputs 89, and instrument shaft 88 allows for the shaft rotation without tangling any control tendons.

Figure 18:
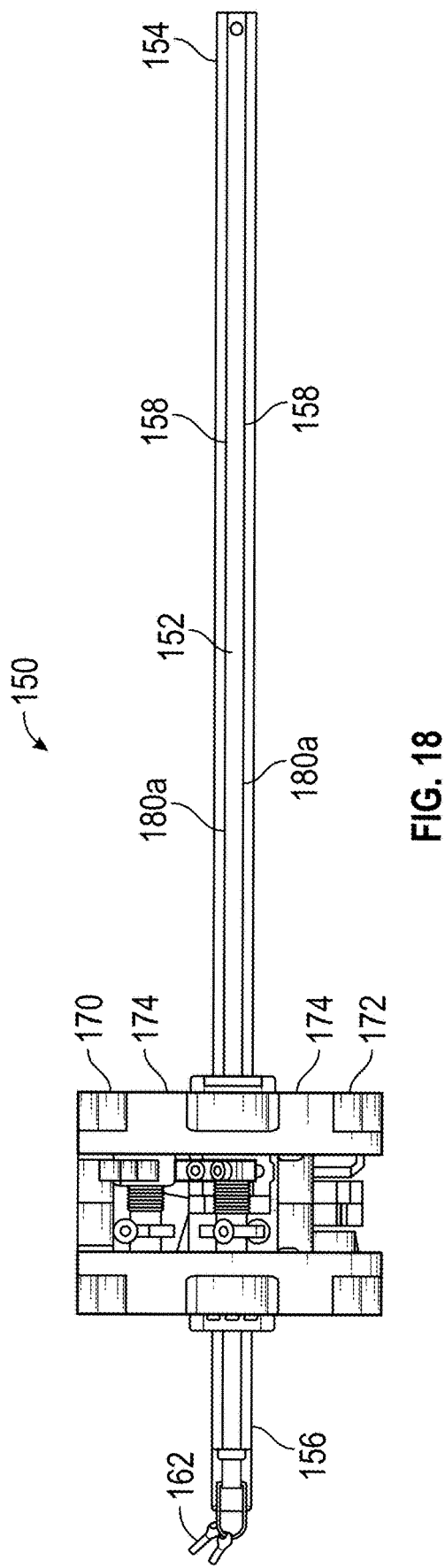
FIG. 18 illustrates an instrument having an instrument-based insertion architecture.

FIG. 18 illustrates an instrument having an instrument based insertion architecture in accordance with some embodiments. The instrument 150 can be coupled to any of the instrument drivers discussed above. The instrument 150 comprises an elongated shaft 152, an end effector 162 connected to the shaft 152, and a handle 170 coupled to the shaft 152. The elongated shaft 152 comprises a tubular member having a proximal portion 154 and a distal portion 156. The elongated shaft 152 comprises one or more channels or grooves 158 along its outer surface. The grooves 158 are configured to receive one or more wires or cables 180 therethrough. One or more cables 180 thus run along an outer surface of the elongated shaft 152. In other embodiments, cables 180 can also run through the elongated shaft 152. Manipulation of the one or more cables 180 (e.g., via an instrument driver) results in actuation of the end effector 162.

The instrument handle 170, which may also be referred to as an instrument base, may generally comprise an attachment interface 172 having one or more mechanical inputs 174, e.g., receptacles, pulleys or spools, that are designed to be reciprocally mated with one or more torque couplers on an attachment surface of an instrument driver.

In some embodiments, the instrument 150 comprises a series of pulleys or cables that enable the elongated shaft 152 to translate relative to the handle 170. In other words, the instrument 150 itself comprises an instrument-based insertion architecture that accommodates insertion of the instrument, thereby minimizing the reliance on a robot arm to provide insertion of the instrument 150. In other embodiments, a robotic arm can be largely responsible for instrument insertion.

E. Controller.

Any of the robotic systems described herein can include an input device or controller for manipulating an instrument attached to a robotic arm. In some embodiments, the controller can be coupled (e.g., communicatively, electronically, electrically, wirelessly and/or mechanically) with an instrument such that manipulation of the controller causes a corresponding manipulation of the instrument e.g., via master slave control.

Figure 19:
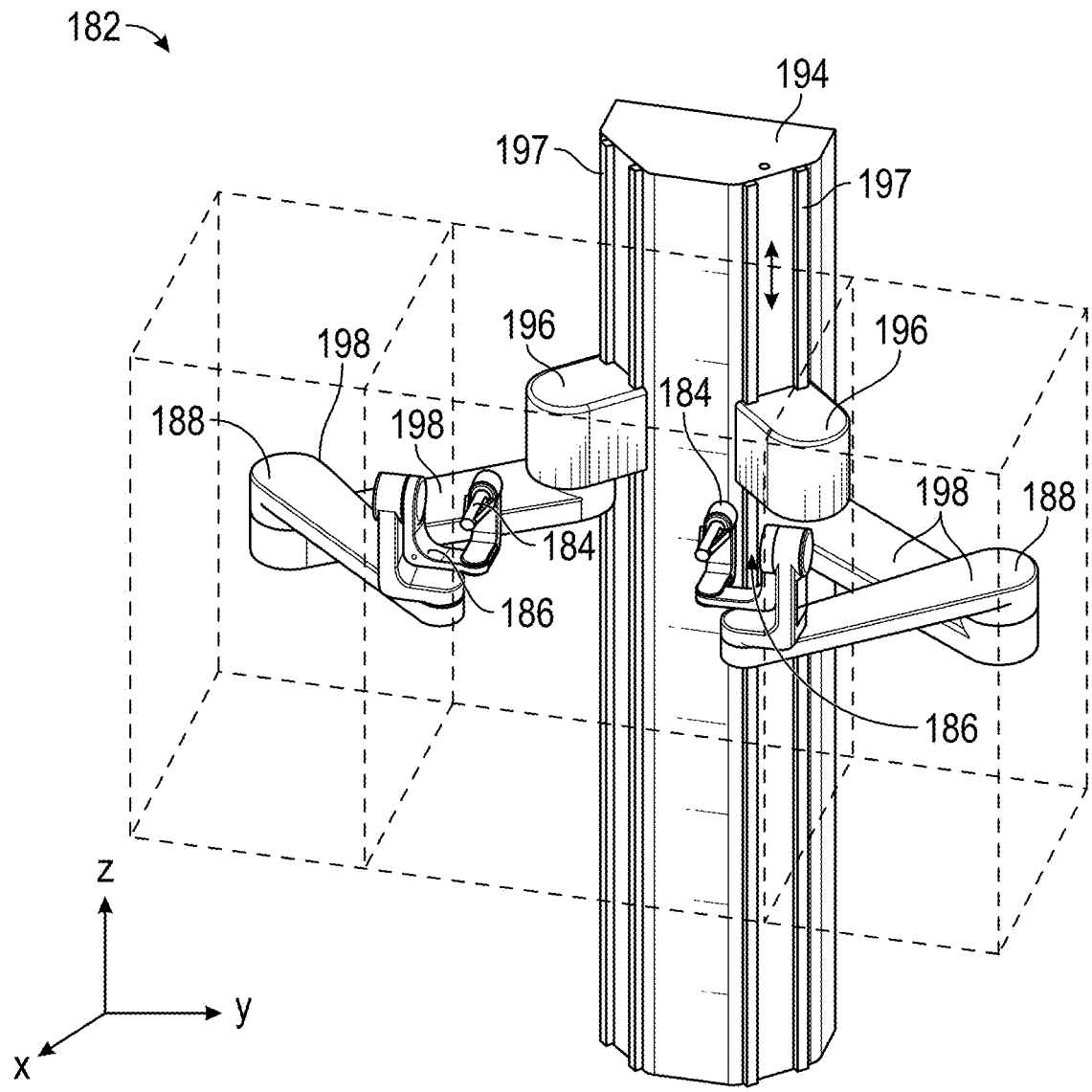
FIG. 19 illustrates an exemplary controller.

FIG. 19 is a perspective view of an embodiment of a controller 182. In the present embodiment, the controller 182 comprises a hybrid controller that can have both impedance and admittance control. In other embodiments, the controller 182 can utilize just impedance or passive control. In other embodiments, the controller 182 can utilize just admittance control. By being a hybrid controller, the controller 182 advantageously can have a lower perceived inertia while in use.

In the illustrated embodiment, the controller 182 is configured to allow manipulation of two medical instruments, and includes two handles 184. Each of the handles 184 is connected to a gimbal 186. Each gimbal 186 is connected to a positioning platform 188.

As shown in FIG. 19, each positioning platform 188 includes a SCARA arm (selective compliance assembly robot arm) 198 coupled to a column 194 by a prismatic joint 196. The prismatic joints 196 are configured to translate along the column 194 (e.g., along rails 197) to allow each of the handles 184 to be translated in the z-direction, providing a first degree of freedom. The SCARA arm 198 is configured to allow motion of the handle 184 in an x-y plane, providing two additional degrees of freedom.

In some embodiments, one or more load cells are positioned in the controller. For example, in some embodiments, a load cell (not shown) is positioned in the body of each of the gimbals 186. By providing a load cell, portions of the controller 182 are capable of operating under admittance control, thereby advantageously reducing the perceived inertia of the controller while in use. In some embodiments, the positioning platform 188 is configured for admittance control, while the gimbal 186 is configured for impedance control. In other embodiments, the gimbal 186 is configured for admittance control, while the positioning platform 188 is configured for impedance control. Accordingly, for some embodiments, the translational or positional degrees of freedom of the positioning platform 188 can rely on admittance control, while the rotational degrees of freedom of the gimbal 186 rely on impedance control.

F. Navigation and Control.

Traditional endoscopy may involve the use of fluoroscopy (e.g., as may be delivered through a C-arm) and other forms of radiation-based imaging modalities to provide endoluminal guidance to an operator physician. In contrast, the robotic systems contemplated by this disclosure can provide for non-radiation-based navigational and localization means to reduce physician exposure to radiation and reduce the amount of equipment within the operating room. As used herein, the term "localization" may refer to determining and/or monitoring the position of objects in a reference coordinate system. Technologies such as preoperative mapping, computer vision, real-time EM tracking, and robot command data may be used individually or in combination to achieve a radiation-free operating environment. In other cases, where radiation-based imaging modalities are still used, the preoperative mapping, computer vision, real-time EM tracking, and robot command data may be used individually or in combination to improve upon the information obtained solely through radiation-based imaging modalities.

Figure 20:
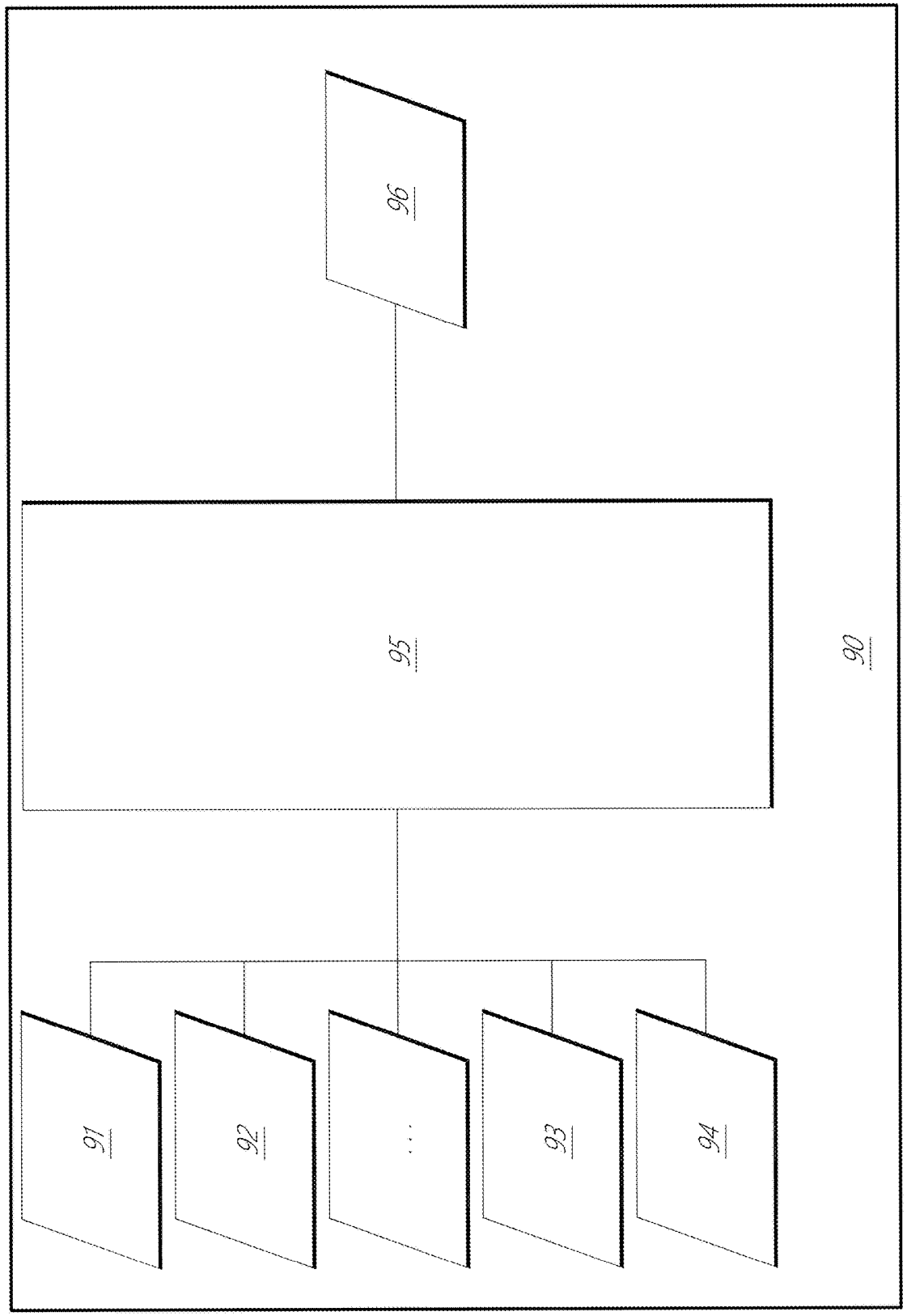
FIG. 20 depicts a block diagram illustrating a localization system that estimates a location of one or more elements of the robotic systems of FIGS. 1-10, such as the location of the instrument of FIGS. 16-18, in accordance to an example embodiment.

FIG. 20 is a block diagram illustrating a localization system 90 that estimates a location of one or more elements of the robotic system, such as the location of the instrument, in accordance to an example embodiment. The localization system 90 may be a set of one or more computer devices configured to execute one or more instructions. The computer devices may be embodied by a processor (or processors) and computer-readable memory in one or more components discussed above. By way of example and not limitation, the computer devices may be in the tower 30 shown in FIG. 1, the cart 11 shown in FIGS. 1-4, the beds shown in FIGS. 5-14, etc.

As shown in FIG. 20, the localization system 90 may include a localization module 95 that processes input data 91-94 to generate location data 96 for the distal tip of a medical instrument. The location data 96 may be data or logic that represents a location and/or orientation of the distal end of the instrument relative to a frame of reference. The frame of reference can be a frame of reference relative to the anatomy of the patient or to a known object, such as an EM field generator (see discussion below for the EM field generator).

The various input data 91-94 are now described in greater detail. Preoperative mapping may be accomplished through the use of the collection of low dose CT scans. Preoperative CT scans are reconstructed into three-dimensional images, which are visualized, e.g. as "slices" of a cutaway view of the patient's internal anatomy. When analyzed in the aggregate, image-based models for anatomical cavities, spaces and structures of the patient's anatomy, such as a patient lung network, may be generated. Techniques such as centerline geometry may be determined and approximated from the CT images to develop a three-dimensional volume of the patient's anatomy, referred to as model data 91 (also referred to as "preoperative model data" when generated using only preoperative CT scans). The use of center-line geometry is discussed in U.S. patent application Ser. No. 14/523,760, the contents of which are herein incorporated in its entirety. Network topological models may also be derived from the CT-images, and are particularly appropriate for bronchoscopy.

In some embodiments, the instrument may be equipped with a camera to provide vision data (or image data) 92. The localization module 95 may process the vision data 92 to enable one or more vision-based (or image-based) location tracking modules or features. For example, the preoperative model data 91 may be used in conjunction with the vision data 92 to enable computer vision-based tracking of the medical instrument (e.g., an endoscope or an instrument advance through a working channel of the endoscope). For example, using the preoperative model data 91, the robotic system may generate a library of expected endoscopic images from the model based on the expected path of travel of the endoscope, each image linked to a location within the model. Intraoperatively, this library may be referenced by the robotic system in order to compare real-time images captured at the camera (e.g., a camera at a distal end of the endoscope) to those in the image library to assist localization.

Other computer vision-based tracking techniques use feature tracking to determine motion of the camera, and thus the endoscope. Some features of the localization module 95 may identify circular geometries in the preoperative model data 91 that correspond to anatomical lumens and track the change of those geometries to determine which anatomical lumen was selected, as well as the relative rotational and/or translational motion of the camera. Use of a topological map may further enhance vision-based algorithms or techniques.

Optical flow, another computer vision-based technique, may analyze the displacement and translation of image pixels in a video sequence in the vision data 92 to infer camera movement. Examples of optical flow techniques may include motion detection, object segmentation calculations, luminance, motion compensated encoding, stereo disparity measurement, etc. Through the comparison of multiple frames over multiple iterations, movement and location of the camera (and thus the endoscope) may be determined.

The localization module 95 may use real-time EM tracking to generate a real-time location of the endoscope in a global coordinate system that may be registered to the patient's anatomy, represented by the preoperative model. In EM tracking, an EM sensor (or tracker) comprising one or more sensor coils embedded in one or more locations and orientations in a medical instrument (e.g., an endoscopic tool) measures the variation in the EM field created by one or more static EM field generators positioned at a known location. The location information detected by the EM sensors is stored as EM data 93. The EM field generator (or transmitter), may be placed close to the patient to create a low intensity magnetic field that the embedded sensor may detect. The magnetic field induces small currents in the sensor coils of the EM sensor, which may be analyzed to determine the distance and angle between the EM sensor and the EM field generator. These distances and orientations may be intraoperatively "registered" to the patient anatomy (e.g., the preoperative model) in order to determine the geometric transformation that aligns a single location in the coordinate system with a position in the preoperative model of the patient's anatomy. Once registered, an embedded EM tracker in one or more positions of the medical instrument (e.g., the distal tip of an endoscope) may provide real-time indications of the progression of the medical instrument through the patient's anatomy.

Robotic command and kinematics data 94 may also be used by the localization module 95 to provide localization data 96 for the robotic system. Device pitch and yaw resulting from articulation commands may be determined during preoperative calibration. Intraoperatively, these calibration measurements may be used in combination with known insertion depth information to estimate the position of the instrument. Alternatively, these calculations may be analyzed in combination with EM, vision, and/or topological modeling to estimate the position of the medical instrument within the network.

As FIG. 20 shows, a number of other input data can be used by the localization module 95. For example, although not shown in FIG. 20, an instrument utilizing shape-sensing fiber can provide shape data that the localization module 95 can use to determine the location and shape of the instrument.

The localization module 95 may use the input data 91-94 in combination(s). In some cases, such a combination may use a probabilistic approach where the localization module 95 assigns a confidence weight to the location determined from each of the input data 91-94. Thus, where the EM data may not be reliable (as may be the case where there is EM interference) the confidence of the location determined by the EM data 93 can be decrease and the localization module 95 may rely more heavily on the vision data 92 and/or the robotic command and kinematics data 94.

As discussed above, the robotic systems discussed herein may be designed to incorporate a combination of one or more of the technologies above. The robotic system's computer-based control system, based in the tower, bed and/or cart, may store computer program instructions, for example, within a non-transitory computer-readable storage medium such as a persistent magnetic storage drive, solid state drive, or the like, that, upon execution, cause the system to receive and analyze sensor data and user commands, generate control signals throughout the system, and display the navigational and localization data, such as the position of the instrument within the global coordinate system, anatomical map, etc.

2. Deflectable Endoscope.

Embodiments of the disclosure relate to systems and techniques for a flexible endoscope to access, visualize, diagnose, and/or treat pathologies in various organs via orifices and lumens of various organs, such as a kidney for ureteroscopy. Because the target location is often internal, it can be difficult to accurately guide the medical instrument to the target location. For example, ureteroscopy is a medical procedure used for the treatment of kidney stones. During the procedure, a thin, flexible tubular tool or medical instrument, such as a ureteroscope or endoscope, can be inserted into the urethra, through the bladder and ureter, into the renal pelvis of the kidney, and into the desired calyx of the kidney.

To navigate through the orifices and lumens of various organs, such as a kidney, the endoscope or ureteroscope should be flexible and deflectable in one or more directions. The ureteroscope should be narrow enough such that it is appropriately sized to fit through narrow natural orifices and lumens (e.g., the urethra or the ureter), flexible enough to appropriately navigate the twists and turns of natural lumens or to reach the desired region within the organ, and stable enough to maintain the desired shape and deflection without structure of the organ providing support. The ureteroscope may be configured to travel through various parts of an anatomy of differing diameter, shape, and configuration. The diameter of the ureteroscope should be small enough to travel through the various parts of the anatomy, while large enough to maintain the stability and control of the ureteroscope. The ureteroscope can be configured to perform various amounts of articulation while navigating anatomical constraints.

One of the challenges with ureteroscopy may be the inability to provide precise control near the distal tip or end of the ureteroscope, particularly after the ureteroscope has already been significantly bent or deflected to reach the desired target within the kidney (such as, e.g., within a specific calyx). For example, when there is a significant deflection or bend radius to reach the mid or lower polar region of the kidney, it can be challenging to articulate the ureteroscope to then select a specific calyx, such as, e.g., an anteriorly or posteriorly pointing calyx.

It can be difficult to finely and accurately articulate the distal section or end of the ureteroscope, in particular when the proximal section is already significantly deflected. It can also be difficult to properly control the distal end without causing unpredictable behavior of the proximal or middle region of the flexible ureteroscope.

The ureteroscope can be deflectable in one or two directions within a first plane. The ureteroscope can also be deflectable in one or two directions in each of two planes. For example, the ureteroscope can be deflected in two directions in a first plane, and can also be deflected in two directions in a second plane, such that ureteroscope (or at least a section thereof) is deflectable in four directions. Additionally, it can be desirable for the at least the distal section to be deflectable in more than one plane to reach the desired area, such as the specific anteriorly or posteriorly pointing calyx.

Figure 21:
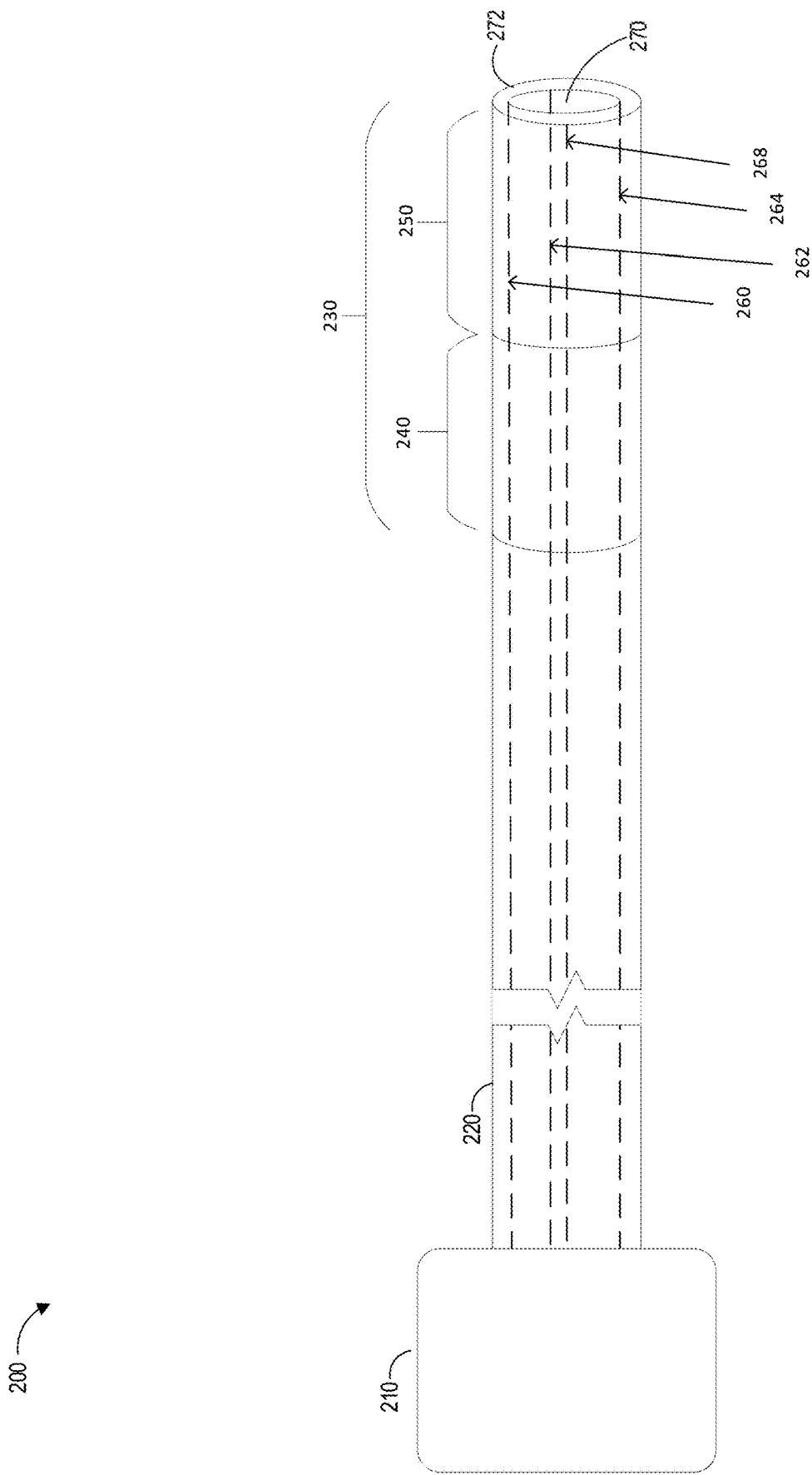
FIG. 21 illustrates an example embodiment of an ureteroscope.

FIG. 21 illustrates an example embodiment of a medical instrument or ureteroscope 200 in accordance with aspects of this disclosure. In the embodiment illustrated in FIG. 21, the ureteroscope 200 can be a robotically-controlled instrument that can include an instrument base or handle 210, an elongate shaft 220, and an articulation section 230. The elongate shaft 220 can extend from the instrument base or handle 210. The articulation section 230 can include a proximal section 240 and a distal section 250. The distal end or tip of the distal section 250 can include a tip portion 272. The proximal section 240 can also be called a first or proximal articulating section, articulation section, bending section, or deflecting section, as well as a two-way deflection section. The distal section 250 can also be called a distal or second articulating section, articulation section, bending section, or deflecting section, as well as a four-way deflection section. The articulation section 230 can also be considered a distal end of the shaft 220 and can also be called an articulating section, bending section, or deflecting section.

One or more cables, pull wires, or pull wire segments can run along the outer surface of the shaft 220 and articulation section 230. Additionally, the one or more cables can run along a central lumen of the shaft 220. The one or more pull wires segments can include one, two, three, four, five, six or more pull wires or segments.

Manipulation of the one or more cables results in actuation or deflection of the articulation section 230. Manipulation of the one or more cables can be controlled via one or more instrument drivers positioned within or connected to the instrument base or handle 210. The instrument base or handle 210 can generally include an attachment interface having one or more mechanical inputs, e.g., receptacles, pulleys, or spools, that are designed to be reciprocally mated with one or more torque couplers on an attachment surface of an instrument driver. The instrument base 210 can include a plurality of drive inputs. The plurality of control cables can be coupled to the plurality of drive inputs and extend along the flexible shaft 220. The plurality of drive inputs are configured to control or apply tension to the plurality of pull wires or control cables in response to drive outputs from the medical robotic system, such as those described in FIGS. 1-20. Furthermore, a robotic arm of a medical robotic system can be configured to carry the ureteroscope. The robotic arm can be configured to apply tension to the plurality of control cables to bend the articulation section 230.

In the embodiment illustrated in FIG. 21, the ureteroscope 200 includes four pull wires or pull wire segments 260, 262, 264, 266. The plurality of pull wires or pull wire segments 260, 262, 264, 266 can extend along the elongate shaft 220 and terminate at the tip portion 272 of the elongate shaft 220. In some embodiments, the instrument 200 comprises a series of pulleys to which the one or more cables 260, 262, 264, 266 can be operatively coupled that enable the shaft 220 to translate relative to the handle 210. Depending on the implementation of the particular instrument 200, the instrument 200 can include an end effector (not illustrated), which can be embodied to perform one or more different medical and/or surgical tasks, which can be effectuated via tensioning the one or more pull wires or cables 260, 262, 264, 266. The end effector can be positioned at a distal end of the instrument 200. The end effector can include one or more tools, such as, e.g., a basket or an energy emitting tool. In some examples, the instrument 200 can include a working channel 270 extending through the elongate shaft 220 permitting at least one tool (not illustrated), such as a basket or laser tool, to be inserted therethrough to interact with a target area, such as within the urinary tract of a patient. The laser tool can be configured to deliver energy configured to be applied to a kidney stone positioned within the urinary tract of the patient, such as to reduce the size of the kidney stone. The basket tool can be configured to capture a kidney stone or portions thereof located within the urinary tract of the patient.

Figure 22A:
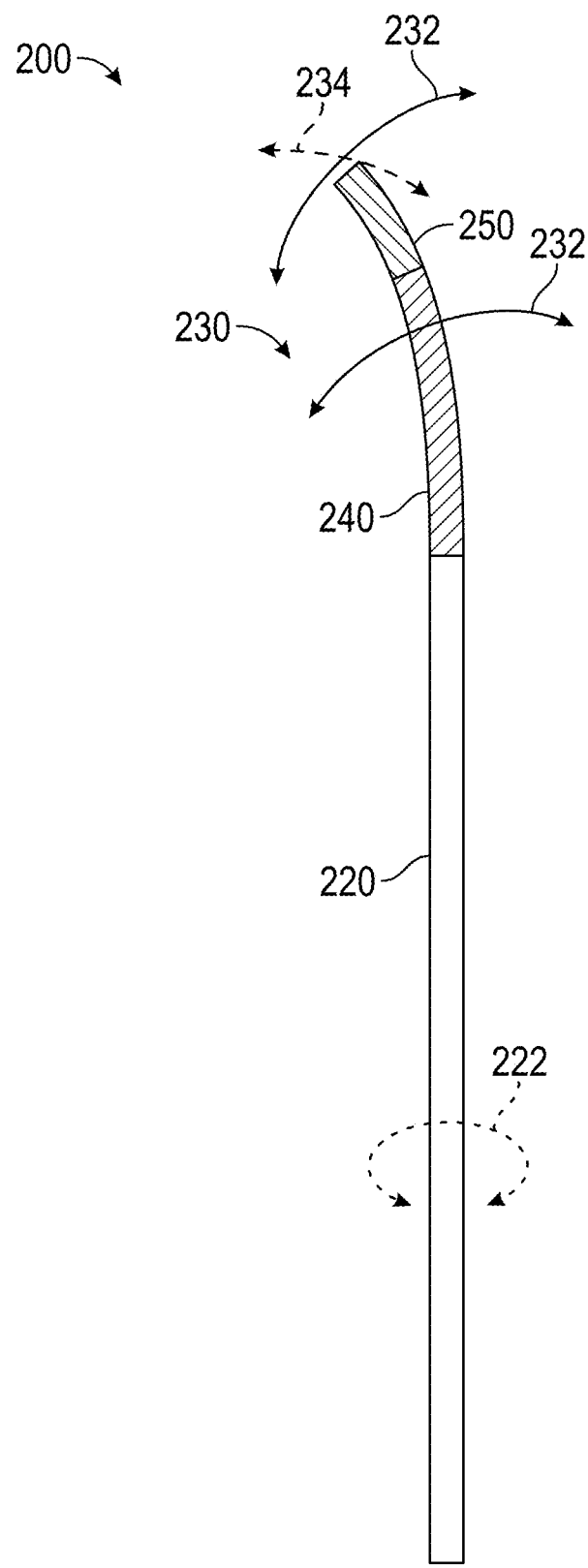
FIG. 22A illustrates another example embodiment of an ureteroscope.

FIG. 22A illustrates an example embodiment of a medical instrument or ureteroscope 200 illustrating the directions of deflection of the various portions of the ureteroscope 200, including the elongate shaft 220 and the articulation section 230, which can include both the proximal section 240 and distal section 250. These various deflection directions as illustrated in FIG. 22A can be controlled or actuated by the plurality of pull wires 260, 262, 264, 266 shown and described in FIG. 21. In order to navigate the ureteroscope 200 through the anatomy, both the proximal section 240 and the distal section 250 can be deflectable in two directions along a curved axis 232 within a first plane, e.g., a first direction and a third direction, wherein the first and third directions are opposite to one another along the curved axis 232 (e.g. left/right or inferior/posterior). The distal section 250 can be further be deflectable in two directions along a curved axis 234 within a second plane, e.g., a second direction and a fourth direction in the second plane, wherein the second and fourth directions are opposite to one another along a curved axis 234 (e.g. up/down or anterior/posterior). The first plane can be orthogonal or transverse to the second plane. The first direction can be orthogonal or transverse to the second direction. The third direction can be orthogonal or transverse to the fourth direction. Therefore, the distal section 250 can be deflectable in two planes and four directions (e.g., left/right and up/down).

The four pull wires 260, 262, 264, 266 illustrated in FIG. 21 can be configured to deflect the articulation section 230 in various directions (e.g. up, down, left, right). The first pull wire 260 as shown FIG. 21 can be configured to deflect the articulation section 230 in a first direction in a first plane. The second pull wire 262 can be configured to deflect the articulation section 230 in a second direction in a second plane, the second plane being transverse or orthogonal to the first plane. The third pull wire 264 can be configured to articulate the articulation section 230 in a third direction, opposite from the first direction within the first plane. The fourth pull wire 266 can be configured to articulate the articulation section 230 in a fourth direction, opposite from the second direction within the second plane.

In some embodiments, the ureteroscope 200 can include an image sensor or camera 650 (FIG. 26B) in the tip portion 272. The first pull wire 260 can articulate the articulation section 230 in the first direction within a first plane along a horizontal axis with respect to a frame of reference of the camera. The second pull wire 262 can articulate the articulation section 230 in a second direction within the second plane along a vertical axis with respect to the frame of reference of the camera. In some embodiments, the tip portion 272 can include an illuminator 750 (FIG. 26B), such as one or more light sources (e.g., light-emitting diodes) or optical fibers configured to convey light from a remote light source (e.g., in a tower). The illuminator 750 can be configure to illuminate a target anatomy to facilitate visualization via images obtained with the camera.

In some embodiments, the first pull wire 260 is configured to deflect both the proximal section 240 and the distal section 250 in a first direction along a first curved axis 232 in a first plane. In some embodiments, the second pull wire 262 is configured to deflect both the proximal section 240 and the distal section 250 in a second direction along a second curved axis 234 within a second plane. In some embodiments, the second pull wire 262 is configured to articulate the distal section 250 in the second direction independently of the proximal section 240, the second direction along the second curved axis 234 being, e.g., transverse to the first direction along the first curved axis 232.

Furthermore, the proximal section 240 and distal section 250 can each have a different bend radius. In some embodiments, upon application of a tensile force to the first pull wire 260, a distal portion of the distal section 250 is configured to bend in the first direction within the first plane at a smaller bend radius than a proximal portion of the proximal section 240. In some embodiments, upon application of the tensile force to the first pull wire 260, a proximal portion of the distal section 250 is configured to bend in the first direction at a same or approximately same bend radius as a distal portion of the proximal section 240. In some embodiments, the proximal section 240 permits bending thereof in the first direction within the first plane and resists bending thereof in the second direction within the second plane. In some embodiments, the distal section 250 permits bending thereof in the first and second directions (e.g., along the respective first and second curved axes 232, 234).

As shown in FIG. 21, an instrument base 210 can be coupled to the elongate shaft 220. The elongate shaft 220 can define a longitudinal axis. The elongate shaft 220 can be configured to rotate relative to the instrument base 210 about the longitudinal axis of the elongate shaft 220. Also illustrated in FIG. 22A, the elongate shaft 220 can rotate or roll in a direction 222 about the longitudinal axis of the elongate shaft 220. The rotation of the elongate shaft 220 relative to the instrument base 210 can be operable to align both the first direction within a first plane, which may be an inferior-superior plane of the patient, and the second direction within the second plane, which may be an anterior-posterior plane of the patient. The roll direction 222 of the elongate shaft 220 can be configured to direct or align the first direction of the articulation section 230 in a desired first direction. For example, as the ureteroscope 200 is directed to make right and left turns from the perspective of the tip portion 272, the elongate shaft 220 can be rolled in a direction 222 about the longitudinal axis to direct the deflection in a different direction, such as up and down.

Figure 22B:
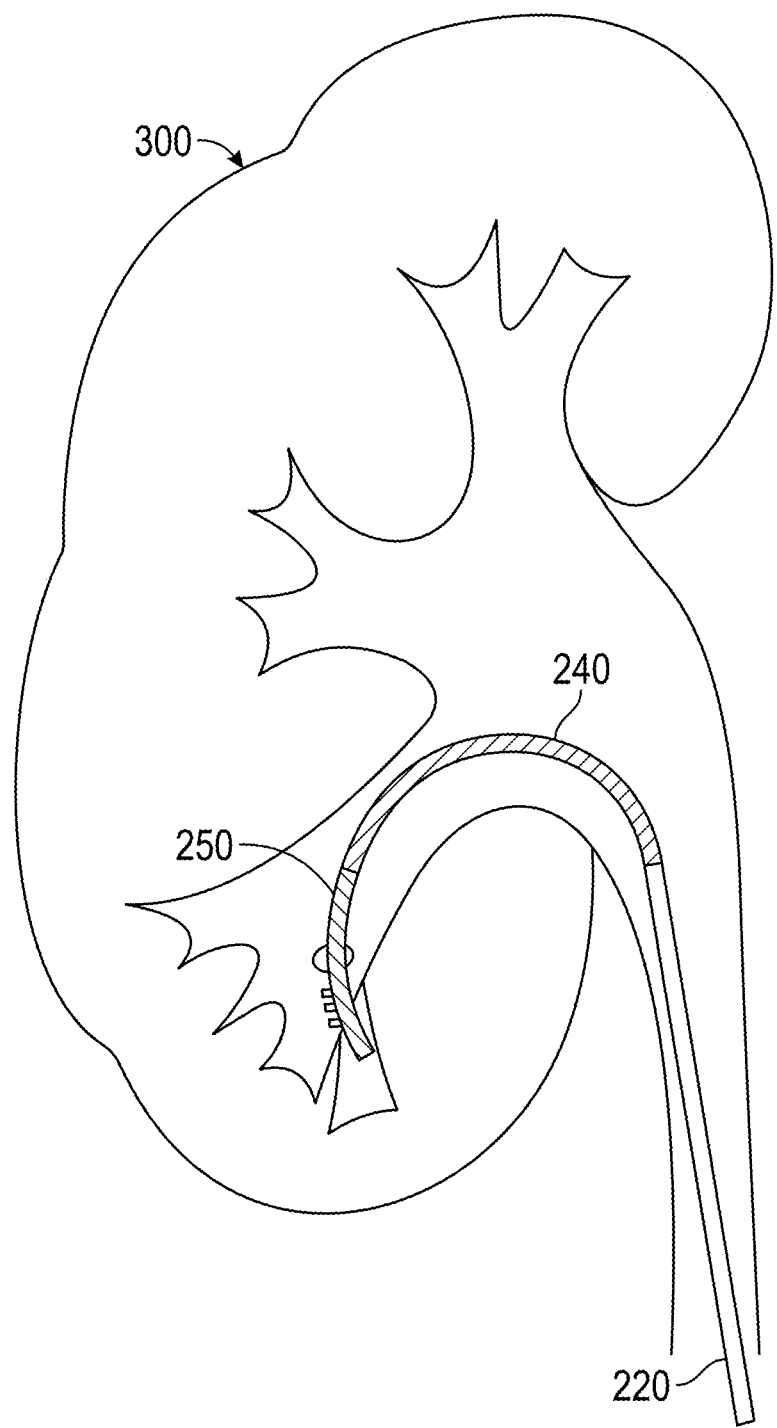
FIG. 22B illustrates the ureteroscope navigated through the natural lumen of a kidney.

FIG. 22B illustrates an example embodiment of a ureteroscope navigated through the natural lumen of a kidney 300. Although the kidney 300 is widely variable in shape, size, and configuration, it is roughly generalizable as planar structure with an upper, middle, and lower pole. From each of these poles stem a series of calyces that point anteriorly or posteriorly. The ureteroscope 200 can be configured for insertion into a urinary tract of a patient. The ureteroscope 200 can be rotated whereby the elongate shaft 220 is rolled about the elongate shaft 220 to point or align the articulation section 230 in the correct direction.

A combined deflection of the ureteroscope 200 where the entire length of the articulation section 230, including both the proximal section 240 and the distal section 250, can function as a 2-way deflecting endoscope. The articulation section 230 can bend as one unit in a first direction within a first plane (e.g., left and/or right) to steer the ureteroscope 200 as it travels through the urethra, into the bladder, and into the renal pelvis. The 2-way deflecting section can be configured to transverse a ureter of a patient. The 2-way deflecting section of the articulation section 230 can be configured to deflect in the first direction to access the various poles of the kidney 300. The deflecting section can be configured to deflect in the first direction along a first curved axis 232 within the first plane to access the specific pole of the kidney 300, which can be considered a primary deflection or a coarse deflection of the ureteroscope 200, as the deflection section 230 can be significantly bent. In some embodiments, both 2-way and 4-way articulation can be used to navigate to various poles of the kidney.

After accessing the desired pole, the 4-way bending section or four direction deflection of the distal section 250 can be configured to sub-select anteriorly and posteriorly pointing calyces. In order to navigate the distal end of the ureteroscope 200 through the anatomy, such as sub-selecting the desired calyx, the distal section 250 can be deflected in a second direction transverse to the first direction. The deflection of the 4-way bending section can be considered a smaller or precise bend. The proximal section 240 can include a primary or coarse deflection of the flexible elongate shaft. The distal bending section can include a secondary or fine articulation of the flexible elongate shaft. The precise second direction may be along a second curved axis 234 within the second plane, and may allow the ureteroscope 200 to sub-select anteriorly and posteriorly pointing calyces, while maintaining the primary deflection curve of the articulation section 230. After reaching the infundibulum of the calyces, the distal section 250 of the articulation section 230 can be directed in the second direction along the second curved axis 234 to select the desired anterior pointing or posterior pointing calyx.

The length of the elongate shaft 220, distal section 250 or the proximal section 240 are variable, such that the lengths could be tuned to enable the ureteroscope 200 to reach the majority of calyces or the various poles of the kidney.

Figure 23:
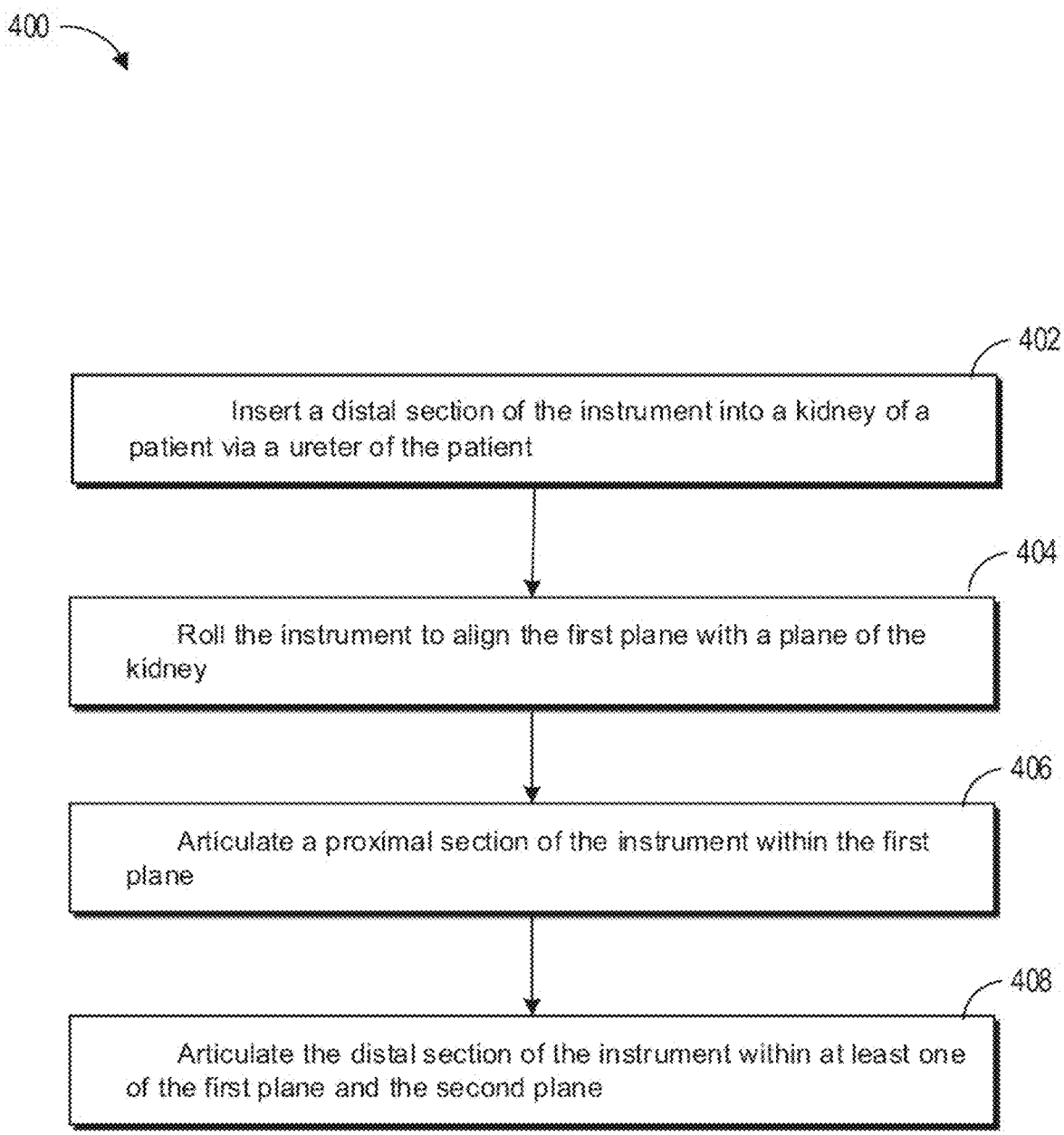
FIG. 23 is a flowchart illustrating an example technique for articulating an ureteroscope for a ureteroscopic procedure.

FIG. 23 is a flow chart illustrating an embodiment of a method 400 for performing a medical procedure that includes deflecting a medical instrument or ureteroscope for a procedure. The method 400 begins at block 402, at which a distal section of the instrument is inserted into a kidney or a patient via a ureter of the patient. As described herein, the instrument can include a distal section and a proximal section. The instrument can include a bending section articulable in a first plane and a second plane, the second plane orthogonal to the first plane. The proximal section of the instrument can include a bending section constrained to articulate in the first plane. The instrument can be robotically controlled, for example, using the robotically-enabled medical systems described above with reference to FIGS. 1-22. The instrument can be manually controlled. In some embodiments, initial access is gained percutaneously or inserted through a natural patient orifice, such as through the urethra.

Next, the method 400 moves to block 404, at which the instrument is rolled to align the first plane of the bending section with a plane of the kidney. In some embodiments, the plane of the kidney can be a primary plane of the kidney or the coronal plane of the kidney.

The method 400 then moves to block 406, at which the articulation section of the instrument is articulated within the first plane. In some embodiments, the proximal section can be limited or constrained to articulate only within the first plane.

Finally, the method 400 moves to block 408, at which the distal section of the instrument is articulated within at least one of the first plane and the second plane. In some embodiments, the distal section of the instrument can be the only portion of the bending section that can be articulated or deflected within the second plane. In some embodiments, the second plane is orthogonal or transverse to the first plane. In some embodiments, the first plane can be the inferior-superior plane. In some embodiments, the second plane can be the anterior-posterior plane.

In some embodiments, the method 400 can be configured to navigate the instrument through a bladder, a ureter, a renal pelvis and an infundibulum of a desired calyx. For example, in some embodiments, at block 406, articulating the proximal portion of the articulation section can be configured to achieve a primary deflection curve. Furthermore, at block 408, the instrument can be configured to articulate the distal portion while maintaining the primary deflection curve of the proximal portion. Additionally, in some embodiments, at block 408, articulating the distal portion can be configured to navigate through the distal portion through the infundibulum and to the desired calyx to reach a target area.

Figure 24A:
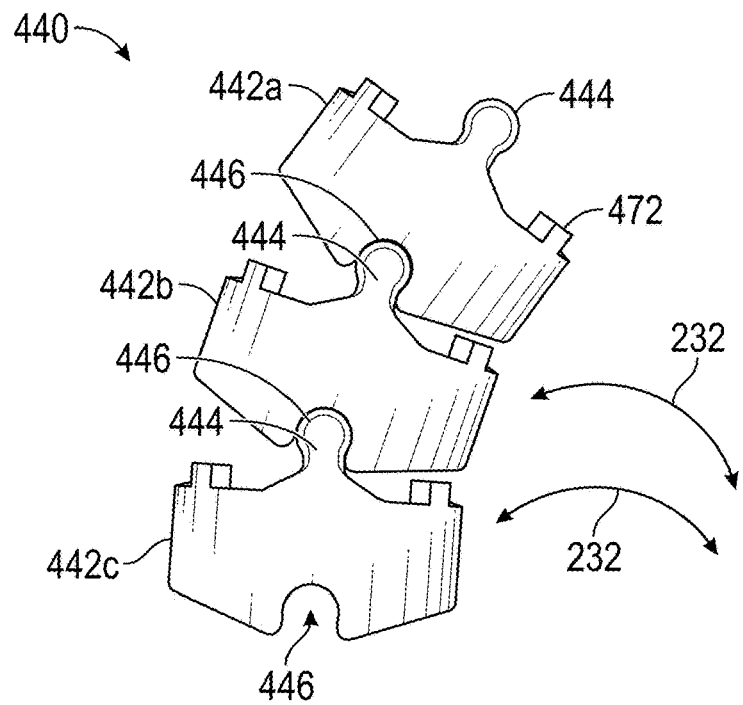
FIG. 24A illustrates an example embodiment of a portion of the ureteroscope deflectable within one plane.

FIG. 24A illustrates an example embodiment of a portion of the ureteroscope deflectable within a single plane. This portion can be the first bending section 450 in a ureteroscope that is deflectable along one or more axes 232 within a first plane. The first bending section 440 can include a series of links 442a-c connected via a series of aligned hinges. As described previously, the first bending section 440 can be a proximal portion of the ureteroscope. The first bending section 440 can include a series of links 442 connected via a series of aligned hinges. The first bending section 440 can include a plurality of links 442, in which each link 442 of the first bending section 440 includes a first hinge member to connect the link 442b to a proximal link 442c and a second hinge member to connect the link 442b to a distal link 442a. The first bending section 440 can include any variable number of plurality of links.

Each link 442 can include a curved surface, recess or opening 446 providing a female hinge member on a proximal side or bottom surface of each link 442. Each link 442 can include a protrusion 444 that provides a male hinge member on a distal side or top surface of the link 442. The protrusion 444 can extend distally from the distal side or top surface of the link 442. The recess 446 can be configured to receive or engage with the protrusion 444 of an adjacent link 442. The recess 446 can be cup-shaped or u-shaped. A hinge can be formed between adjacent links 442 (such as 442a and 442b). The hinge can be formed by the recess 446 of a first link 442b receiving a protrusion 444 of an adjacent link 442a or 442c. The corresponding shapes of the recess 446 and protrusion 444 can allow the rotation of one link 442b relative to another link 442a or 442c in a first direction along the first curved axis 232 within the first plane. Each of the aligned hinges of the proximal section 440 can rotatably connect a pair of adjacent links 442 about a pivot axis parallel to an adjacent hinge. Each link 442 can be aligned such that the hinges are aligned, where the protrusions 444 and recesses 446 are radially aligned with one other on each link 442. For each of the links 442 in the first bending section 440, the first hinge member and second hinge member are aligned.

Figure 24B:
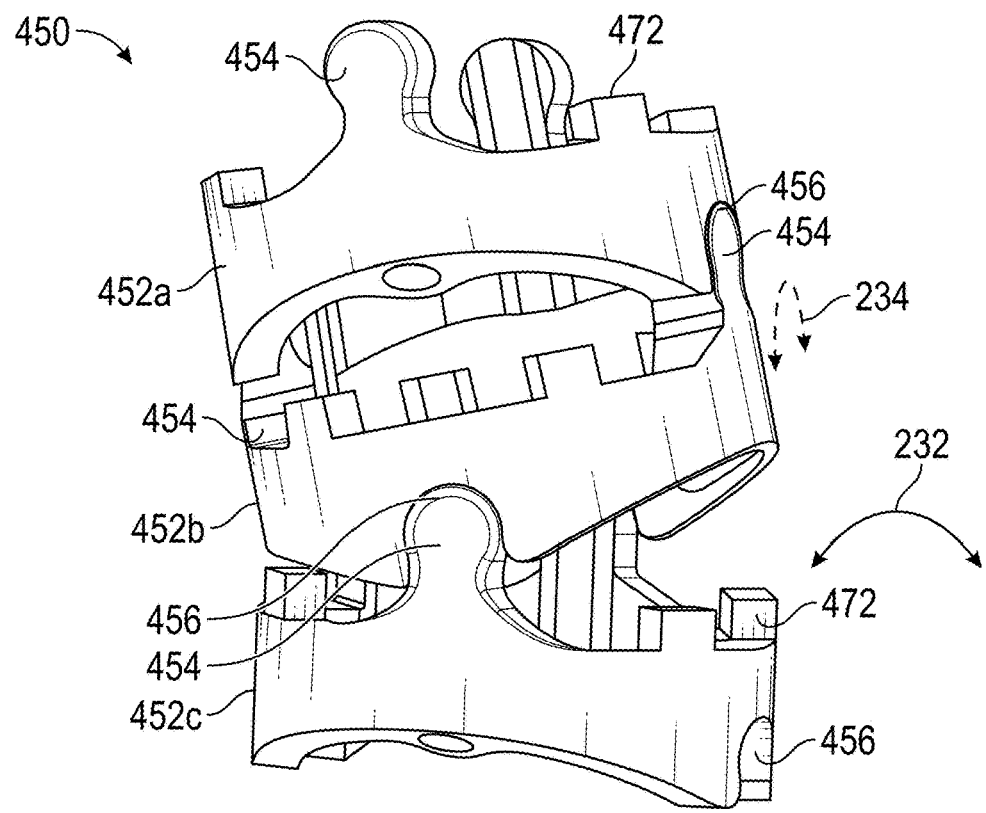
FIG. 24B illustrates an example embodiment of a portion of the ureteroscope deflectable within two planes.

FIG. 24B illustrates an example embodiment of a portion of the ureteroscope deflectable within two different planes. This portion deflectable within the two planes (e.g., along curved axes 232, 234) can be a second bending section 450 of an ureteroscope. The second bending section 450 can include a series of links 452 connected via a series of staggered hinges. As described previously, the second bending section 450 can be a distal portion of the ureteroscope. The second bending section 450 includes a plurality of links 452, in which each link 452 includes a first hinge member configured to connect the link 452 to an adjacent proximally located link (e.g., connecting link 452b to a proximal link 452c) and a second hinge member configured to connect the link to an adjacent distally located link (e.g. connecting link 452b to a distal link 452a). In related aspects, the second hinge member may be rotationally offset from the first hinge member, e.g., by about 90 degrees. The second bending section 450 can include any variable number of plurality of links.

Similar to the links 442 of the proximal section 440, each link 452 of the second bending section 450 can include a curved surface, recess or opening 456 on a proximal side or bottom surface of each link 452. Each link 452 can include a protrusion 454 on a distal side or top surface of the link 452. The recess 456 of one link 452b can be configured to receive or engage with the protrusion 454 of a neighboring or adjacent link 452a or 452c. A hinge can be formed between adjacent links 452 (such as 452a and 452b). The hinge can be formed by the recess 456 of a first link 452b receiving a protrusion 454 of an adjacent link 452a or 452c. It will be appreciated that, in various embodiments, the positioning of the male and female hinge members can be reversed or modified. For example, the male hinge members can be positioned on the proximal side of each link, and the female hinge members can be positioned on the distal side of each link.

In the second bending section 450, the hinges that connect each pair of adjacent links 452 are staggered. This staggering of the hinges can allow the distal section 450 to articulate both in a first plane (e.g., along the first curved axis 232) as well as a second plane (e.g., along the second curved axes 234). Each of the staggered hinges of the distal section 450 can rotatably connect a pair of adjacent links 452 about a pivot axis perpendicular to an adjacent hinge. For each of the links 452a-c in the second bending section 450, every other hinge member can be positioned 90 degrees offset from each other. The first hinge member and second hinge member can be positioned 90 degrees offset from each other.

Figure 25:
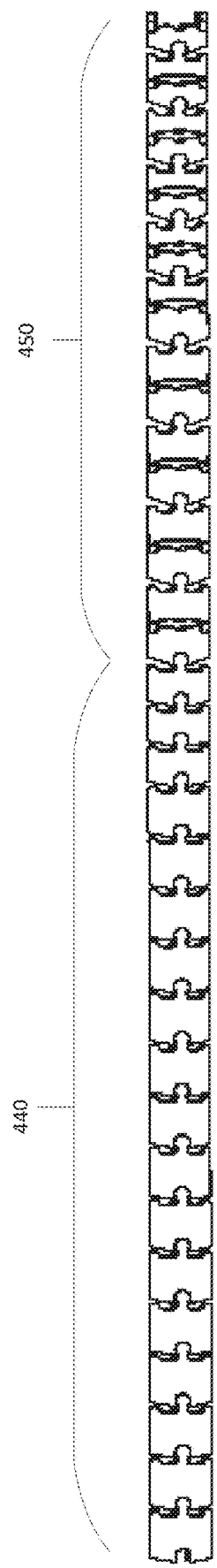
FIG. 25 illustrates an example embodiment of an articulation section of an ureteroscope.

Although the staggered arrangement of the link hinges in the second/distal section 450 are shown in FIGS. 24B and 25 where every other hinge member are offset from each other, the staggering of the hinge members can be every third, fourth, or fifth hinge member, or any other pattern or number. For example, the second bending section 450 can be such that a first pair (A-A) is aligned with each other, a second pair (B-B) is aligned with each other and positioned 90 degrees offset from the first pair (A-A), and a third pair (A-A) is aligned with each other and positioned 90 degrees offset from the second pair (B-B). The third pair (AA) would be aligned with the first pair (A-A). This alternating pair can be called an A-A-B-B hinge pattern. In some embodiments, this repeating pattern can be, instead of pairs, alternating groups of three, four, five, or any number of hinges.

The alternating patterns can have equal ratios of hinge numbers or vary in ratios of hinge members. For example, a first hinge member (A) can be 90 degrees offset from a second hinge member (B). The third hinge member (B) can be aligned with the second hinge member (B). The pattern would then repeat, where the fourth hinge (A) member can be aligned with the first hinge member (A), and so on. This could be called an A-B-B pattern.

The pattern of aligned and staggered hinges can be consistent throughout the second bending section 450. The pattern of aligned and staggered hinges can also vary through the second bending section 450. For example, the proximal portion of the second bending section 450 can have the two aligned alternating hinges previously described and the distal portion of the second bending section 450 can have the every other staggered hinge as described previously (as illustrated in FIG. 24B).

Although the staggered hinge members in the second bending section 450 are illustrated such that the hinge members are 90 degrees offset from each other, the hinge members can be offset from each other in any number of degrees, such as between 45 to 90 degrees, 50 to 75 degrees, 60 to 80 degrees, 80 to 90 degrees.

There are various patterns that could be created in staggering patterns, ranges, or lengths of the hinges in this second bending section 450. This allows the second bending section 250 to have a specific bend radius or bending profile, which is customizable depending on the desired control and specific patient's anatomy to be navigated. Similarly, the different variations of lengths (with the number of links in each section or the length of individual link) can alter the specific bend radius or bending profile, and therefore can alter the shape of the first curved axis 232 and/or the second curved axis along which the second bending portion may move along.

The links 442 of the first bending section 440 and the links 452 of the second bending section may include a series of posts 472 that extend distally from the distal surface of each link 442, 452. The series of posts 472 may be shorter in length than the protrusions 444 and positioned around the radius of each link 442, 452. The posts 472 may be configured to contact and engage with a bottom or proximal surface of a distal adjacent link. These posts 472 may provide support as the links are deflected in the desired direction.

FIG. 25 illustrates an example embodiment of an articulation section 430 of an ureteroscope in an undeflected state. The ureteroscope can include a proximal section 440 as described in FIG. 24A and a distal section 450 as described in FIG. 24B.

The length of the proximal section 440 and the length of the distal section 450 can vary. In some embodiments, the length of the proximal section 440 and the length of the distal section 450 can be equal. In other embodiments, the length of the proximal section 440 can be longer than the length of the distal section 450. In some embodiments, a ratio of the length of the proximal section 440 to the length of the distal section 550 can be 75:25, 70:30, 60:40, 50:50, 40:60, 30:70, 25:75, or any other suitable ratio.

The lengths of the individual links 442 of the first bending section 440 can vary. For example, the series of links 442 can have a gradient length that shortens in a distal direction (wherein the distal links 442 are shorter in length than the proximal links 442 in the first bending section 440). In another example, the proximal portion of the first bending section 440 can have links 442 which have a longer length than the links 442 of the distal portion of the first bending section 440. Similarly, the lengths of the individual links 452 of the second bending section 450 can vary in a similar manner. Additionally or alternatively, the angle that adjacent links can be bent relative to each other can be tuned to determine the bend radius. For example, the hinge members or stops between adjacent links can be used to constrain the minimum bend radius for a bending section.

Figure 26A:
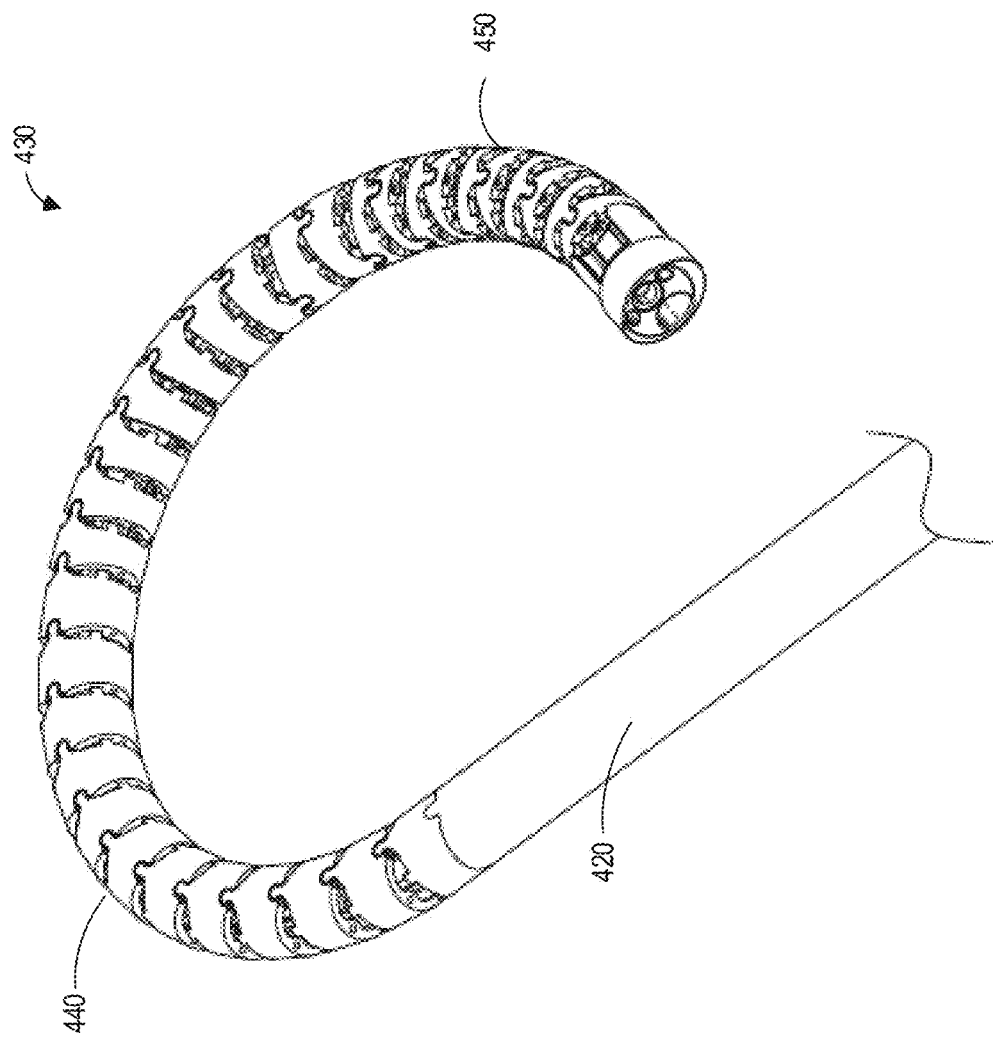
FIG. 26A illustrates the ureteroscope of FIG. 25 deflected within one plane.

FIG. 26A illustrates the articulation section 430 of FIG. 25 articulated within a single plane. Both the first bending section 440 and the second bending section 450 are bent within the same plane. As illustrated in FIG. 26A, the lengths of the links 452 in the second bending section 450 are shorter than the lengths of the links 442 in the first bending section 440, which creates a smaller bend radius of the second bending section 450 as compared to the bend radius of the first bending section 440.

Figure 26B:
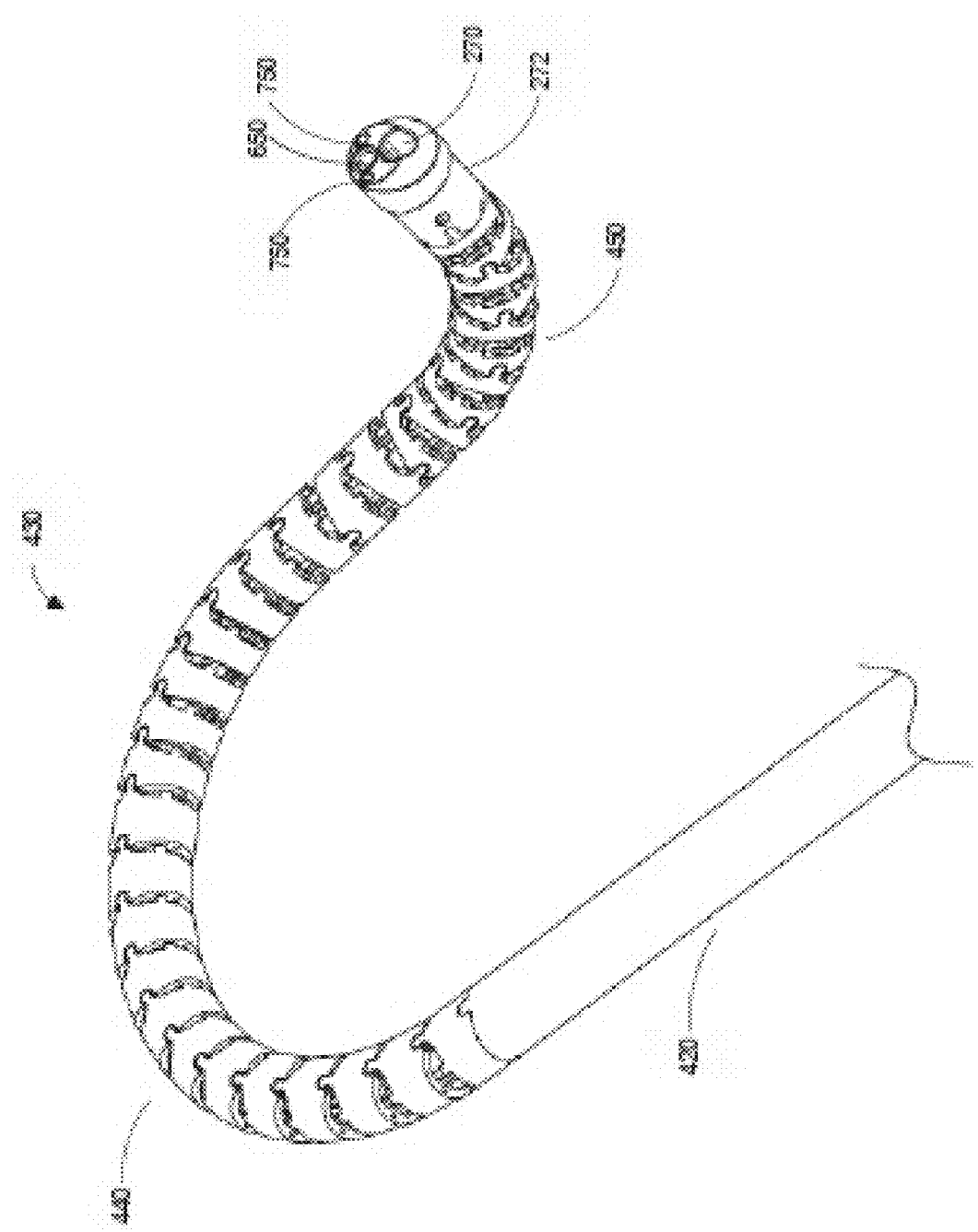
FIG. 26B illustrates the ureteroscope of FIG. 25 and FIG. 26A deflected in two planes.

FIG. 26B illustrates the ureteroscope of FIG. 25 and FIG. 26A articulated within two planes. The first bending section 440 is deflected in a first direction within a first plane. The first bending section 404 can be constrained to bend within a first plane. The second bending section 450 is deflected in a second direction (out of the first plane or in a transverse direction from the first direction) within a second plane (which is orthogonal to the first plane). The second bending section can be bendable along the first plane and out of the first plane.

Figure 27A:
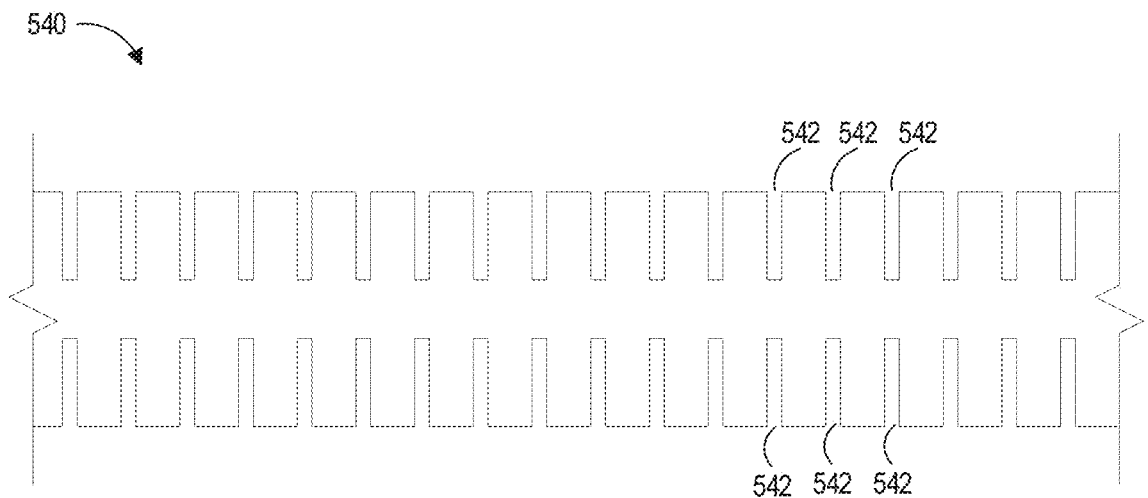
FIG. 27A illustrates an example embodiment of a portion of the ureteroscope deflectable within one plane.

FIG. 27A illustrates another example embodiment of a portion of the ureteroscope deflectable in one plane. This first portion can be the first bending section 540 in a ureteroscope that is deflectable in only one plane. The first bending section 540 can include a deformable flexure having greater bending stiffness in the second plane than in the first plane. The deformable flexure of the first bending section 540 can include a first tube section with a first pattern of voids 542 having second order rotational symmetry about a longitudinal axis thereof. The flexible shaft can be a tube where the first bending section 540 includes a series of cutouts 542 around the tube with 180 degree rotational symmetry. The series of cutouts or voids 542 may be aligned with each other along the length of the first bending section 540, such that the series of cut outs or voids 542 are radially in the same place along the length of the first bending section 540. The series of cutouts or voids 542 may be positioned on opposite sides of the longitudinal axis, such that they are positioned 180 degrees away from each other radially. The series of cutouts or voids 542 allows the first bending section 540 increases the flexibility which allows the first bending section 540 to bend within a first plane.

Figure 27B:
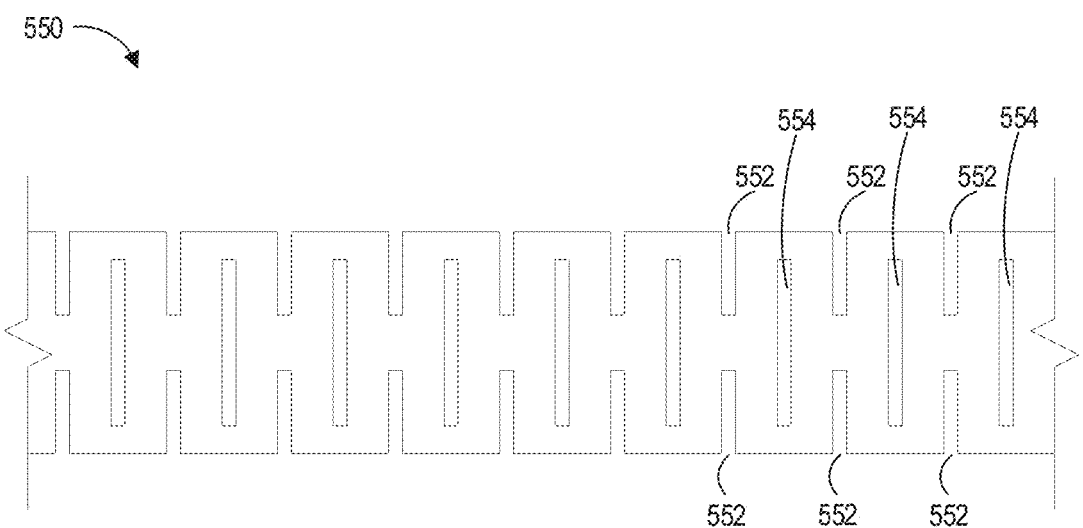
FIG. 27B illustrates an example embodiment of a portion of the ureteroscope deflectable within two planes.

FIG. 27B illustrates an example embodiment of a portion of the ureteroscope deflectable in two planes. This second portion can be the second bending section 550 in a ureteroscope that is deflectable within two planes (e.g., where the first and second planes are orthogonal). The second bending section 550 can include a deformable flexure having a same bending stiffness in the first and second planes. The deformable flexure of the second bending section 550 comprises a second tube section with a first pattern similar to the first bending section 540, where the second tube section has a first pattern of voids 552 to allow the ureteroscope to be deflectable within one plane.

Similar to the first pattern of voids 542 in the first bending section 540, the deformable flexure of the second bending section 550 can include a second tube section with a first pattern of voids 552 having second order rotational symmetry about a longitudinal axis thereof. The deformable flexure of the second bending section 550 may also include a second pattern of voids 554 having n-th order rotational symmetry about a longitudinal axis thereof, n being an integer multiple of four.

Similar to the first series of cut outs 542 in the first bending section 540, the second bending section 550 can be a tube including a series of cutouts 552 around the tube with 180 degree rotational symmetry. The second bending section 550 can additionally have a second series of cutouts 554 positioned radially around the tube with 90 degree rotational symmetry.

The first series of cutouts or voids 552 may be aligned with each other along the length of the second bending section 550, such that the first series of cutouts or voids 552 are radially in the same place along the length of the second bending section 550. Similarly, the second series of cutouts or voids 554 may be aligned with each other along the length of the second bending section 550, such that the second series of cutouts or voids 554 are radially in the same place along the length of the second bending section 550 The first series of cutouts or voids 552 may be positioned on opposite sides of the longitudinal axis, such that they are positioned 180 degrees away from each other radially. Similarly, the second series of cutouts or voids 554 may be positioned on opposite sides of the longitudinal axis, such that they are positioned 180 degrees away from each other radially.

Figure 28A:
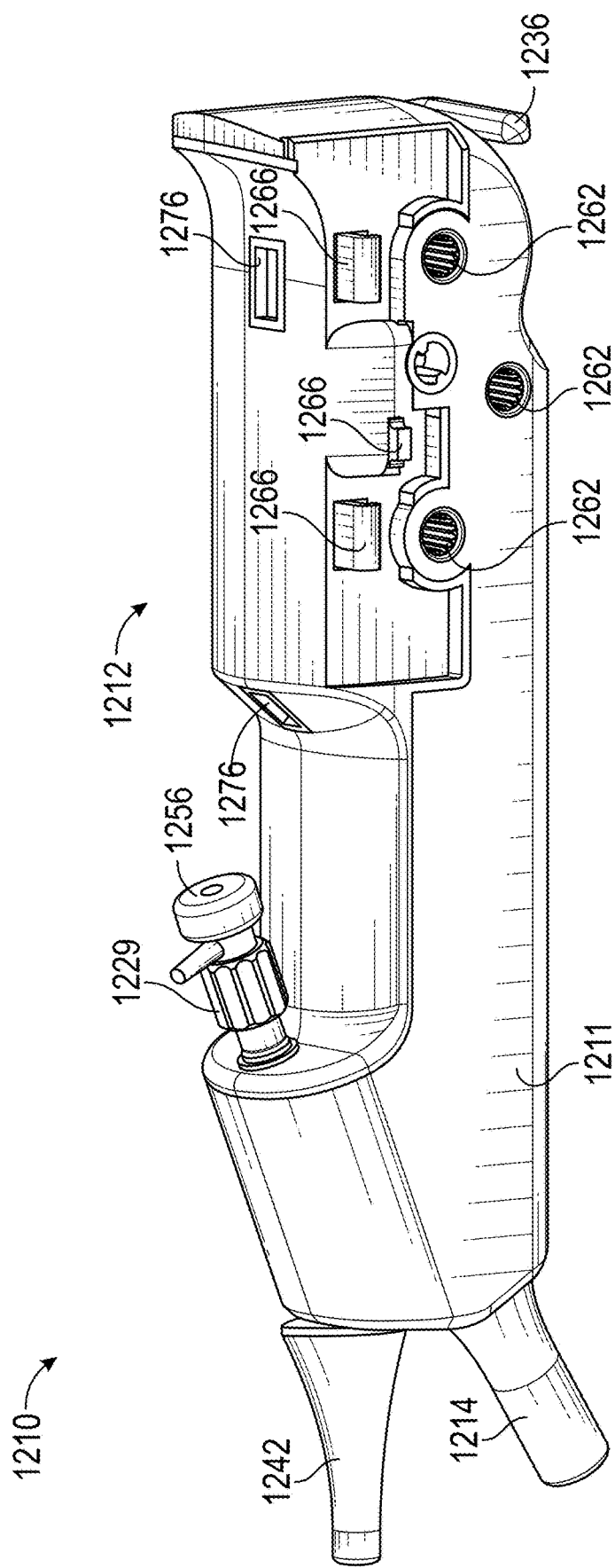
FIG. 28A illustrates an example endoscope.

FIG. 28A illustrates a bottom view of a portion of an example endoscope 1210 according to one configuration, which can be coupled to and used with an instrument, such as instrument 200 similar to the embodiments described above with reference to FIGS. 21 and 22A-22B. As illustrated, the endoscope 1210 includes an endoscope base 1211 (or endoscope handle) and an elongated shaft (not shown). The elongate shaft (such as elongate shaft 220 as shown in FIGS. 21 and 22A-22B) may extend distally from an endoscope outlet 1242. The elongate shaft is configured to be inserted into a patient during a medical procedure. The elongate shaft can be configured to be articulable and controllable, such that the elongate shaft can be navigated and steered through the patient's anatomy. For example, in some embodiments, the elongate shaft comprises a thin, flexible body configured to be inserted into and guided through patient lumens, such as the urethra, ureter, gastrointestinal tract, esophagus, airways of the lungs, etc. As described above, pull wires (such as pull wires 260, 262, 264, 266) can be included in or on the elongate shaft to control articulation of the elongate shaft. The elongate shaft can extend between a distal end and a proximal end. The distal end can be configured to be inserted into the patient. The proximal end can be attached to the endoscope base 211 via the endoscope outlet 1242. The elongate shaft can include a working channel (not illustrated) through which additional instruments or tools can pass for delivery to the distal end. The endoscope 1210 can include a working channel entry port (not illustrated) configured to allow access to the working channel. An instrument shaft inlet 1256 can allow coupling of an instrument shaft (described below) to be inserted therein and to be coupled into the working channel entry port and into the working channel.

The endoscope base 1211 is configured to allow both manual control and robotic control of the endoscope 1210. For example, the endoscope base 1211 is configured to be physically held and manually manipulated to provide manual control, and to couple to an instrument drive mechanism to provide robotic control. In some embodiments, a sterile adapter can be positioned between the endoscope base 1211 and the instrument drive mechanism to maintain a sterile field during a medical procedure.

As illustrated, the endoscope base 1211 includes a housing 1212. As illustrated, the housing 1212 can also be shaped to include an instrument coupled thereto. The endoscope base 1211 includes one or more endoscope receiving elements 1276. The endoscope receiving elements 1276 are configured to couple with corresponding elements of another instrument (e.g., the instrument 200 described above). For example, the endoscope receiving elements 1276 can couple with corresponding elements (not shown) of an instrument base or handle 210, such as shown in FIG. 21. The housing 1212 of the endoscope base 1211 can be shaped to provide an ergonomic fit for the instrument handle in a practitioner's hand and/or for coupling of another instrument. For example, the housing 1212 shape can allow the endoscope base 1211 to be more easily or comfortably held during manual control. Alternatively or additionally, the housing 1212 shape can provide (or not block) access to one or more unused robotic drive outputs on the instrument drive mechanism as will be described below. The endoscope base 1211 can include a power access 1214 for connecting to a power unit to power the one or more instruments of a medical instrument system. The power access 1214 can be configured to provide electrical and/or visual connections to the endoscope 1210. In the illustrated embodiment, the power access 1214 is illustrated as a strain relief for an umbilical cable that leads to a connector at a tower.

The endoscope base 1211 can include an instrument shaft inlet 1256 that allows insertion of an instrument (e.g., the instrument 200 described above) therein. The instrument inlet may include an instrument inlet actuator 1229. The instrument inlet actuator 1229 can allow manual control of the shaft of the instrument. In some embodiments, the instrument inlet actuator 1229 can be tightened to improve a connection between the instrument shaft and the endoscope 1210. The instrument inlet actuator 1229 can include a Luer lock assembly. In some embodiments, the instrument inlet actuator 1229 can prevent inadvertent slipping (e.g., translation, rotation) of the instrument shaft within the instrument shaft inlet 1256. Additionally or alternatively, the instrument inlet actuator 1229 can be configured to allow a practitioner to manually rotate the instrument shaft.

The endoscope base 1211 can include a manual actuator 1236. In the illustrated embodiment, the manual actuator 1236 is configured as a lever, although other mechanical structures such as sliders or wheels are possible. As will be described in greater detail below, the manual actuator 1236 is configured to provide manual two-way deflection control for the endoscope 1210. In the illustrated embodiment, the manual actuator 1236 is configured to be manipulated or rotated back and forth. Moving the manual actuator 1236 in a first direction can cause articulation of the elongate shaft in a first articulation direction within a first plane, and moving the manual actuator 236 in a second direction (opposite the first direction) can cause articulation of the elongate shaft in a third articulation direction (opposite the first articulation direction) within the first plane. The first and third articulation directions can be substantially opposite (e.g., up and down), although this need not be the case in all embodiments.

The endoscope base 1211 can also include a manual roll input controllable by the endoscope outlet 1242. Though not shown, the distal end of the elongate shaft of the endoscope 1210 can be attached to the endoscope outlet 1242. In some embodiments, the elongate shaft extends through the endoscope outlet 1242 and into the housing 1212 of the endoscope 1210. The endoscope outlet 1242 can be configured to allow the elongated shaft to rotate relative to the endoscope base 1211. As illustrated, the endoscope outlet 1242 can be a twister or rotatable handle or grip that can rotate relative to the housing 1212. For example, the endoscope outlet 1242 can rotate in a clockwise and/or counterclockwise motion. In some embodiments, the endoscope outlet 1242 rotates in both the clockwise and counterclockwise directions. The elongate shaft can be rotationally fixed relative to the endoscope outlet 1242 such that rotation of the endoscope outlet 1242 causes rotation of the elongate shaft. Rotation of the elongate shaft can be in the same direction and equal to corresponding motion of the endoscope outlet 1242, although this need not be the case in all embodiments. The elongated shaft may be permitted to rotate (e.g., roll) in both rotational directions of at least 90, at least 100, at least 110, at least 120, at least 130, at least 140, at least 150, at least 160, at least 170, at least 180, at least 190, at least 200, at least 210, at least 220, at least 230, at least 240, at least 250, at least 260, at least 270, at least 280, at least 290, at least 300, at least 310, at least 320, at least 330, at least 340, at least 350, or at least 360 degrees. This roll control is optional and, in certain embodiments, the roll can be controlled manually by, for example, rotating the endoscope 1210.

With continued reference to FIG. 28A, the endoscope 1210 includes a plurality of robotic endoscope drive inputs 1262. In the illustrated embodiment, the endoscope 1210 includes three robotic endoscope drive inputs 1262, although other numbers of robotic endoscope drive inputs 1262 can be used in other embodiments. The robotic endoscope drive inputs 1262 are configured to engage corresponding robotic drive outputs on an instrument drive mechanism when the endoscope base 1211 is attached to the instrument drive mechanism. Example robotic drive outputs and instrument drive mechanisms are shown in FIGS. 15-17 (described above). The robotic drive outputs of the instrument drive mechanism engage and transfer torque to or rotate the robotic endoscope drive inputs 1262. In some embodiments, each of the robotic endoscope drive inputs 1262 are rotatable in both the clockwise and counterclockwise directions. In the illustrated embodiment, the robotic endoscope drive inputs 1262 are configured as grooved or keyed recesses and are configured to engage robotic drive outputs that are configured as protruding splines. The robotic drive outputs can be driven by motors to rotate in clockwise and counterclockwise directions. When the robotic drive outputs are engaged with the robotic endoscope drive inputs 1262, the robotic drive inputs transfer rotational motion to the robotic endoscope drive inputs 1262. In some embodiments, the robotic drive outputs drive the robotic endoscope drive inputs 1262. In some embodiments, this arrangement can be reversed or other types and configurations of robotic drive inputs and outputs can be used.

The illustrated embodiment of the endoscope 1210 is configured at least for robotic four-way deflection control and robotic roll control. In this embodiment, two of the robotic drive inputs 1262 are configured for deflection control, and the other of the robotic drive inputs 1262 is configured for roll control. Each of the two of the robotic drive inputs 1262 configured for deflection control can permit two-way deflection control so that, together, four-way deflection control can be achieved.

As will be described in more detail below, in some embodiments, actuation of a first robotic drive input of one of the robotic endoscope drive inputs 1262 can be configured to cause the same articulation of the elongate shaft as actuation of the manual drive input. For example, both the first robotic drive input and the manual actuator 1236 can be configured to cause articulation of the elongate shaft in up and down directions. This can be because, as will be described below, both the first robotic drive input and the manual actuator 1236 can be connected to the same articulation mechanism (e.g., a corresponding pulley) within the housing 1212 of the endoscope base 1211. In some embodiments, the two-way deflection control provided by the manual actuator 1236 is the same as the two-way deflection control provided by the first robotic drive input.

Figure 28B:
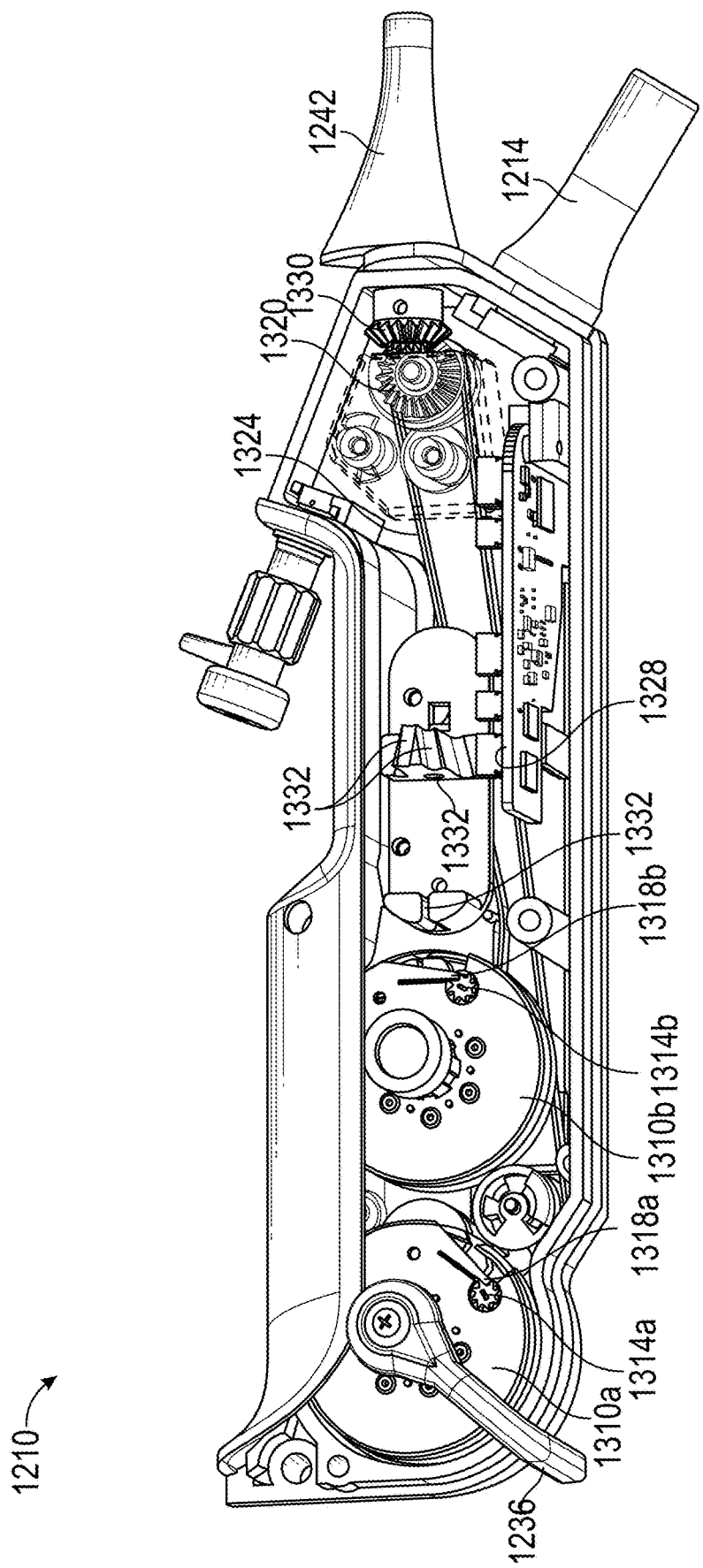
FIG. 28B illustrates some of the internal components of the example endoscope of FIG. 28A.

FIG. 28B illustrates some of the internal components of the endoscope base 211. A first side view of the endoscope base 1211 is shown with a portion of the housing 1212 removed so as to view some of the internal components. As shown, two pulleys (or pulley assemblies), first pulley 1310a and second pulley 1310b, are positioned within the housing 1212. In this embodiment, each of the first pulley 1310a and the second pulley 1310b is associated with two of four articulation directions of the elongated shaft. In some embodiments, each plane of articulation (e.g., up-down or left-right) can be linked to one pulley assembly. For example, up and down articulation of the elongate shaft can be associated with the first pulley 1310a and left and right articulation of the elongate shaft can be associated with the second pulley 1310b.

In the illustrated embodiment, the first pulley 1310a is rotationally coupled to a corresponding first robotic drive input and the second pulley 1310b is rotationally coupled to a corresponding second robotic drive input. Rotation of the first robotic drive input can thus cause corresponding rotation of the first pulley 1310a, and rotation of the second robotic drive input can cause corresponding rotation of the second pulley assembly 1310b. As noted above, rotation of the first pulley 1310a can cause articulation of the elongate shaft within a first plane in the first and third directions (such as in the up and down directions), and rotation of the second pulley 1310b can cause articulation of the elongate shaft within a second plane in the second direction and fourth directions (such as in the left and right directions). Thus, for some embodiments, robotic four-way deflection control can be achieved with the first and second robotic drive inputs and the first and second pulley assemblies 1310a, 1310b. Alternatively, four separate pulleys could be used with four corresponding robotic drive inputs.

As noted above, the manual actuator 1236 can also be rotationally coupled to the first pulley 1310a such that the manual actuator 1236 can be used to rotate the first pulley 1310a. Rotation of the first pulley 1310a can cause articulation of the elongate shaft within the first plane in the first and third directions (such as in the up and down directions). Thus, in the illustrated embodiment, both the manual actuator 1236 and the first robotic drive input are each rotationally coupled to the first pulley 1310a, such that both can cause articulation of the elongate shaft within the first plane in the first and third directions (in, for example, the up and down directions). In the illustrated embodiment, the manual actuator 1236 is configured as a lever that is rigidly attached to the first pulley 1310a. For example, an end of the manual actuator 1236 may be attached to a shaft of the first pulley 1310a. Thus, any motion of the manual actuator 1236 can be directly transferred to the first pulley 1310a. Accordingly, the endoscope 1210 is configured for manual two-way deflection control (with the manual actuator 1236) and four-way deflection control (with the first and second robotic drive inputs).

In the illustrated embodiment, the second pulley 1310b is only articulable with the second robotic drive input. In some embodiments, a second manual actuator (not illustrated) can be rotationally coupled to the second pulley 1310b to further allow manual control of the elongated shaft within a second plane in the second and fourth directions (in, for example, the left and right directions).

In some examples, the manual actuator 1236 can cause articulation of the articulation section 230, including the proximal section 240 and/or the distal section 250. For example, the manual actuator 1236 can cause articulation of both the proximal section 240 and the distal section 250 within a (such as left/right or inferior/posterior), such that the articulation section 230 is controlled in two direction deflection. In some examples, the robotic arm, through the first robotic drive input or the second robotic drive input, can cause articulation of one or more of the sections of the articulation section 230, such as the proximal section 240 and/or the distal section 250. In some examples, the robotic arm can cause articulation within the first plane (such as left/right or inferior/posterior) and within a second plane (such as up/down or anterior/posterior), such that the distal section 250 can be controlled to achieve four direction deflection. In some examples, the proximal section 240 can bend in response to a manual input or interaction from the user, such as through the manual actuator 1236, whereas the distal section 250 can bend in response to control by the robotic arm, such as through the first and second robotic drive inputs. In another example, the distal section 250 can bend in a first plane, based on the manual input or interaction with the user, such as through the manual actuator 1236; then, the distal section 250 can bend out of the first plane and in a second plane, based on control by the robotic arm, such as through the first, second, and/or third robotic drive input(s).

Robotic shaft roll may be achieved by a first bevel gear 1320 and a second bevel gear 1330. The first bevel gear 1320 can be attached to the third robotic drive input, such that rotation of the third robotic drive input can cause rotation of the first bevel gear 1320. The second bevel gear 1330 can be attached to the proximal end of the elongate shaft of the endoscope 1210 such that rotation of the second bevel gear 1330 can cause rotation of the elongate shaft relative to the endoscope base 1211. The first and second bevel gears 1320, 1330 can be engaged to transfer rotational movement of the third robotic drive input to the elongate shaft of the endoscope 1210. For example, as shown, a drive belt 1324 may be used to operatively couple the first bevel gear 1320 to the third robotic drive input (not shown) from a distance. The third drive input may be proximal of the first bevel gear 1320. The third drive input may be disposed between the first and second robotic drive inputs of the endoscope 1210. Other methods and mechanisms for transferring rotational motion of the third robotic drive input to the elongate shaft of the endoscope 1210 are also possible. In some embodiments, as the elongate shaft is rolled, the internal components (such as coil pipes, pull wires, electrical wires, and fiber optics) are allowed to twist as they may be fixed to both the proximal and distal ends of the elongate shaft of the endoscope 1210. Twisting of the internal components can be achieved throughout much of the length of the elongate shaft, minimizing the resultant force/torque applied to the proximal and distal terminations.

The endoscope 1210 can also include an electronic controller 1328. The electronic controller 1328 may be coupled to power via the power access 1214. The electronic controller 1328 can be configured to provide electronic control for one or more elements that is disposed inside the working channel of the elongate channel of the endoscope 1210. For example, the endoscope 1210 may include a camera, a light source, microphone, another sensor, and/or another tool for use during a medical procedure. The electronic controller 1328 can provide power and/or signal for one or more of these tools. Additionally or alternatively, the electronic controller 1328 may receive signal from one or more of these tools and pass that information to a computer (not shown). For example, the electronic controller 1328 may pass video and/or audio signal to a remote display to aid a practitioner during a surgery.

The endoscope 1210 may include one or more guide elements 1332. The guide elements 1332 can be positioned and sized to receive one or more pull wires (such as pull wires 260, 262, 264, 266) therethrough and to promote their passage through the working channel of the elongate shaft of the endoscope 1210. The guide elements 1332 may advantageously reduce damaging effects of friction on the pull wires (such as pull wires 260, 262, 264, 266) as they articulate the elongate shaft. The guide elements 1332 can guide the pull wires (such as pull wires 260, 262, 264, 266) between the first and/or second pulley assemblies 1310a, 1310b and the endoscope outlet 1242. A first level of guide elements 1332 may be configured to guide the pull wires from the first pulley 1310a, and a second level of guide elements 1332 can be configured to guide the pull wires from the second pulley 1310b. The first and second levels may be spaced from each other (e.g., along an axis approximately parallel to an axis of rotation of one or more of the first and/or second pulley assemblies 1310a, 1310b).

One or each of the pulleys 1310a, 1310b can include corresponding pulley ratchets 1314a, 1314b and/or pulley lock mechanisms 1318a, 1318b, such as shown in FIG. 28B. For clarity, reference will be made to the first pulley 1310a, but the same functionality may apply to the second pulley 1310b. The pulley ratchets 1314a, 1314b can be used to provide initial tension to the corresponding pulleys 1310a, 1310b, such as during manufacturing. Thus, once the pull wires (such as pull wires 260, 262, 264, 266) are properly tensioned by rotating the pulley ratchets 1314a, 1314b, the pulley lock mechanisms 1318a, 1318b prevent the pulley ratchets 1314a, 1314b from rotating in the opposite direction.

3. Implementing Systems and Terminology.

Implementations disclosed herein provide systems, methods and apparatus for endoscopy to access, visualize, and treat pathologies in various organs via natural orifices and lumens of various organs.

It should be noted that the terms "couple," "coupling," "coupled" or other variations of the word couple as used herein may indicate either an indirect connection or a direct connection. For example, if a first component is "coupled" to a second component, the first component may be either indirectly connected to the second component via another component or directly connected to the second component.

The control and use of the endoscopic system functions described herein may be stored as one or more instructions on a processor-readable or computer-readable medium. The term "computer-readable medium" refers to any available medium that can be accessed by a computer or processor. By way of example, and not limitation, such a medium may comprise random access memory (RAM), read-only memory (ROM), electrically erasable programmable read-only memory (EEPROM), flash memory, compact disc read-only memory (CD-ROM) or other optical disk storage, magnetic disk storage or other magnetic storage devices, or any other medium that can be used to store desired program code in the form of instructions or data structures and that can be accessed by a computer. It should be noted that a computer-readable medium may be tangible and non-transitory. As used herein, the term "code" may refer to software, instructions, code or data that is/are executable by a computing device or processor.

The methods disclosed herein comprise one or more steps or actions for achieving the described method. The method steps and/or actions may be interchanged with one another without departing from the scope of the claims. In other words, unless a specific order of steps or actions is required for proper operation of the method that is being described, the order and/or use of specific steps and/or actions may be modified without departing from the scope of the claims.

As used herein, the term "plurality" denotes two or more. For example, a plurality of components indicates two or more components. The term "determining" encompasses a wide variety of actions and, therefore, "determining" can include calculating, computing, processing, deriving, investigating, looking up (e.g., looking up in a table, a database or another data structure), ascertaining and the like. Also, "determining" can include receiving (e.g., receiving information), accessing (e.g., accessing data in a memory) and the like. Also, "determining" can include resolving, selecting, choosing, establishing and the like.

The phrase "based on" does not mean "based only on," unless expressly specified otherwise. In other words, the phrase "based on" describes both "based only on" and "based at least on."

The previous description of the disclosed implementations is provided to enable any person skilled in the art to make or use the present invention. Various modifications to these implementations will be readily apparent to those skilled in the art, and the generic principles defined herein may be applied to other implementations without departing from the scope of the invention. For example, it will be appreciated that one of ordinary skill in the art will be able to employ a number corresponding alternative and equivalent structural details, such as equivalent ways of fastening, mounting, coupling, or engaging tool components, equivalent mechanisms for producing particular actuation motions, and equivalent mechanisms for delivering electrical energy. Thus, the present invention is not intended to be limited to the implementations shown herein but is to be accorded the widest scope consistent with the principles and novel features disclosed herein.

What is claimed is:

1. A ureteroscope, comprising:
an elongate shaft configured for insertion into a urinary tract of a patient, the elongate shaft comprising a proximal section, a distal section, and a tip portion;
a first drive input configured to provide robotic control of a first pull wire;
a second drive input configured to provide robotic control of a second pull wire;
a manual actuator; and
a plurality of pull wires extending along the elongate shaft and terminating at the tip portion of the elongate shaft, the plurality of pull wires comprising the first pull wire and the second pull wire, the first pull wire mechanically coupled to (i) the first drive input and (ii) the manual actuator configured to provide manual control of the first pull wire, the second pull wire mechanically coupled to the second drive input and decoupled from any manual actuator,
wherein the proximal section is articulatable in a first direction via operation of the first drive input and articulatable manually in the first direction via operation of the manual actuator;
wherein a motion of the manual actuator is mechanically transferred to the first pull wire;
wherein the distal section is articulatable in a second direction transverse to the first direction via operation of the second drive input;
wherein the first drive input of the ureteroscope is mechanically couplable to a first drive output of a robotic instrument driver;
wherein the second drive input of the ureteroscope is mechanically couplable to a second drive output of the robotic instrument driver; and
wherein the robotic instrument driver is configurable to, when the first drive output is coupled to the first drive input and the second drive output is coupled to the second drive input, use the second drive output to cause the second pull wire to articulate the distal section in the second direction independently of the proximal section while using the first drive output to apply a tension to the first pull wire to maintain articulation of the proximal section in the first direction.

2. The ureteroscope of claim 1, further comprising a camera in the tip portion, wherein the first direction is along a horizontal axis with respect to a frame of reference of the camera, and the second direction is along a vertical axis with respect to the frame of reference of the camera.

3. The ureteroscope of claim 1, further comprising:
an instrument base coupled to the elongate shaft, wherein the elongate shaft defines a longitudinal axis; and
a third drive input;
wherein the third drive input is couplable to a third drive output of the robotic instrument driver, and
wherein the robotic instrument driver is configurable to, when the third drive output is coupled to the third drive input, roll the elongate shaft relative to the instrument base about the longitudinal axis.

4. The ureteroscope of claim 3, wherein the elongate shaft is rollable relative to the instrument base to align the first direction along an inferior-superior axis of the patient and the second direction along an anterior-posterior axis of the patient.

5. The ureteroscope of claim 1, wherein the plurality of pull wires further comprises:
a third pull wire configured to articulate each of the proximal section and the distal section in a third direction opposite the first direction; and a fourth pull wire configured to articulate the distal section in a fourth direction independently of the proximal section, the fourth direction being opposite the second direction, wherein the first direction is orthogonal to the second direction, and wherein the third direction is orthogonal to the fourth direction.

6. The ureteroscope of claim 1, wherein, upon application of a tensile force to the first pull wire, a distal portion of the distal section is configured to bend in the first direction at a smaller bend radius than a proximal portion of the proximal section.

7. The ureteroscope of claim 6, wherein, upon application of the tensile force to the first pull wire, a proximal portion of the distal section is configured to bend in the first direction at a same bend radius as a distal portion of the proximal section.

8. The ureteroscope of claim 1, further comprising:
a working channel extending through the elongate shaft, the working channel permitting at least one of a basket tool or a laser tool to be inserted therethrough to interact with a target in the urinary tract of the patient.

9. The ureteroscope of claim 1, wherein:
the proximal section permits bending thereof in the first direction and resists bending thereof in the second direction; and
the distal section permits bending thereof in the first and second directions.

10. The ureteroscope of claim 1, wherein:
the proximal section comprises a series of links connected via a series of aligned hinges; and
the distal section comprises a series of links connected via a series of staggered hinges.

11. The ureteroscope of claim 10, wherein:
each hinge of the series of aligned hinges of the proximal section rotatably connects a pair of adjacent links about a pivot axis parallel to an adjacent hinge; and
each hinge of the series of staggered hinges of the distal section rotatably connects a pair of adjacent links about a pivot axis perpendicular to an adjacent hinge.

12. The ureteroscope of claim 1, wherein:
the proximal section comprises a deformable flexure having greater bending stiffness in the second direction than in the first direction; and
the distal section comprises a deformable flexure having a same bending stiffness in the first and second directions.

13. A ureteroscope, comprising:
an instrument base configured to couple to an instrument driver, the instrument base comprising a manual actuator configured to provide manual control of a first pull wire and a plurality of drive inputs including a first drive input configured to provide robotic control of the first pull wire and a second drive input configured to provide robotic control of a second pull wire; and
a flexible shaft extending from the instrument base, the flexible shaft comprising first and second articulating sections configured to traverse a ureter of a patient;
wherein the first articulating section is articulatable robotically in a first direction via operation of the first drive input and articulatable manually in the first direction via operation of the manual actuator,
wherein the first drive input and the manual actuator are mechanically coupled to the first pull wire,
wherein a motion of the manual actuator is mechanically transferred via the first pull wire to articulate the first articulating section,
wherein the second articulating section is articulatable robotically in a second direction transverse to the first direction via operation of the second drive input mechanically coupled to the second pull wire, and
wherein the second pull wire is decoupled from any manual actuator.

14. The ureteroscope of claim 13, wherein the first and second articulating sections each comprise a plurality of links in which each link of the first and second articulating sections comprises a first hinge member to connect the link to a proximal link and a second hinge member to connect the link to a distal link.

15. The ureteroscope of claim 14, wherein:
for each of the plurality of links in the first articulating section, the first hinge member and second hinge member are aligned; and
for each of the plurality of links in the second articulating section, the first hinge member and second hinge member are positioned 90 degrees offset from each other.

16. The ureteroscope of claim 13, wherein the first articulating section is longer than the second articulating section.

17. The ureteroscope of claim 13, wherein a ratio of a length of the first articulating section to the second articulation section is between 60:40 and 50:50.

18. The ureteroscope of claim 13, wherein:
the flexible shaft comprises a tube;
the first articulating section comprising a series of cutouts positioned radially around the tube with 180 degree rotational symmetry; and
the second articulating section comprising a series of cutouts positioned radially around the tube with 90 degree rotational symmetry.

19. The ureteroscope of claim 13,
wherein the first and second drive inputs are configured to apply tension to at least one of the first and second pull wires to bend the first and second articulating sections along a first plane, and to bend the second articulating section along the first and second planes.

* * * * *